(12) United States Patent
Desrochers

(10) Patent No.: US 12,135,318 B2
(45) Date of Patent: Nov. 5, 2024

(54) FIELD CALIBRATION FOR A MULTIPOINT AIR SAMPLING SYSTEM

(71) Applicant: Measured Air Performance, LLC, Merrimack, NH (US)

(72) Inventor: Eric Desrochers, Merrimack, NH (US)

(73) Assignee: Measured Air Performance, LLC, Merrimack, NH (US)

(*) Notice: Subject to any disclaimer, the term of this patent is extended or adjusted under 35 U.S.C. 154(b) by 606 days.

(21) Appl. No.: 17/430,123

(22) PCT Filed: Apr. 14, 2020

(86) PCT No.: PCT/US2020/028045
§ 371 (c)(1),
(2) Date: Aug. 11, 2021

(87) PCT Pub. No.: WO2020/214550
PCT Pub. Date: Oct. 22, 2020

(65) Prior Publication Data
US 2022/0099641 A1    Mar. 31, 2022

Related U.S. Application Data

(60) Provisional application No. 62/834,526, filed on Apr. 16, 2019.

(51) Int. Cl.
G01N 33/00         (2006.01)

(52) U.S. Cl.
CPC ..... *G01N 33/0006* (2013.01); *G01N 33/0011* (2013.01); *G01N 33/007* (2013.01); *G01N 33/0072* (2024.05)

(58) Field of Classification Search
None
See application file for complete search history.

(56) References Cited

U.S. PATENT DOCUMENTS 4,399,942 A    8/1983  Chand
5,394,092 A    2/1995  Wentworth et al.
(Continued)

FOREIGN PATENT DOCUMENTS

CN    201080605 Y  *  7/2008
CN    109444340 A     3/2019
(Continued)

OTHER PUBLICATIONS

PCT International Preliminary Report dated Oct. 28, 2021 for International Application No. PCT/US2020/028045; 10 Pages.
(Continued)

*Primary Examiner* — Daniel S Larkin
(74) *Attorney, Agent, or Firm* — DALY, CROWLEY, MOFFORD & DURKEE, LLP

(57) ABSTRACT

A multi-point air sampling system that can use a field reference subsystem to process sensor feedback to efficiently and reliably monitor and improve air quality within a space. The field reference subsystem can interface with multiple types of multi-point air sampling systems to ensure that sensors are operational and producing accurate measurements. Included within the field reference subsystem can be one or more permeation sources for generating test gases used to evaluate the integrity of the sensors, a processor for receiving the results of the test-gas evaluations to recurrently verify the operation level of each sensor, and a reporting system for carrying out actions in response to the recurrent verification of the sensors.

17 Claims, 25 Drawing Sheets

(56) References Cited

U.S. PATENT DOCUMENTS

| | | |
|---|---|---|
| 5,962,774 A | 10/1999 | Mowry et al. |
| 6,125,710 A | 10/2000 | Sharp |
| 6,241,950 B1 | 6/2001 | Veelenturf et al. |
| 6,646,444 B2 | 11/2003 | Dolgov et al. |
| 7,421,911 B2 | 9/2008 | Desrochers et al. |
| 8,147,302 B2 | 4/2012 | Desrochers et al. |
| 8,584,505 B2 | 11/2013 | Penth et al. |
| 9,651,531 B2 | 5/2017 | Desrochers |
| 11,460,203 B2 | 10/2022 | Desrochers |
| 2017/0269044 A1 | 9/2017 | Diekmann |

FOREIGN PATENT DOCUMENTS

| | | | | |
|---|---|---|---|---|
| DE | 102014200310 A * | 8/2014 | ........... | G01N 27/227 |
| WO | WO 2020/214550 A1 | 10/2020 | | |

OTHER PUBLICATIONS

PCT International Search Report and Written Opinion dated Aug. 3, 2020 for International Application No. PCT/US2020/028045; 16 Pages.

Sharp, "Demand-Based Control of Lab Air Change Rates;" Article from ASHRAE Journal; Feb. 2010; 9 Pages.

\* cited by examiner

600B

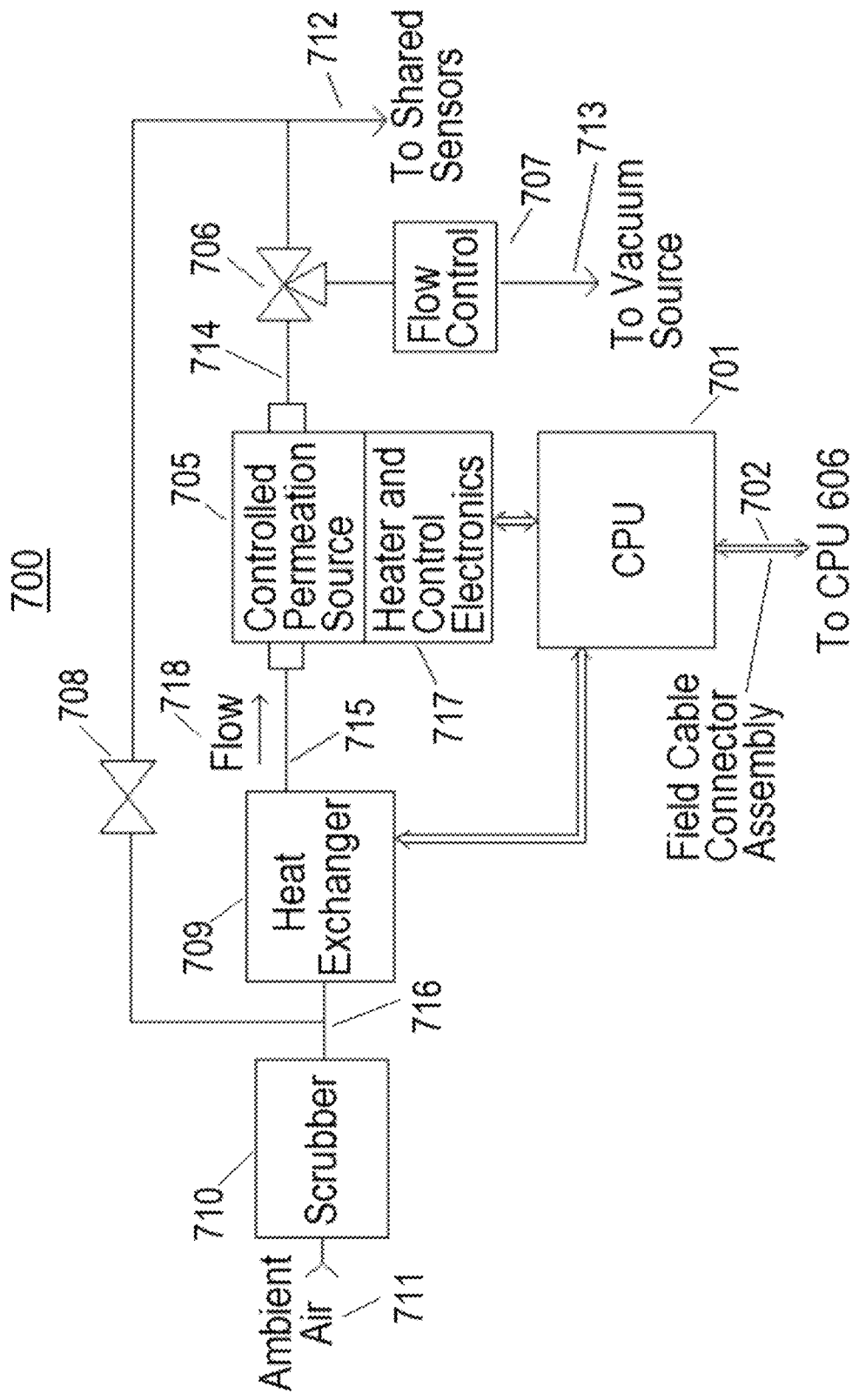

800

Scan for
Calibration Data

FIG. 15
1500

| Date | Time | Reference Serial Number | Reference Gas | Reference Calibrated ppm | Measurement Units | Sensor Serial Number | Sensor Reading ppm | Delta ppm | +/- Tolerance | Pass/Fail | Corrective Action | Reporting Action | SQI |
|---|---|---|---|---|---|---|---|---|---|---|---|---|---|
| 5/19/2019 | 8:00:00 AM | REF1289765 | ISOP* | 1.3 | PPM ISOB.** | PID3459685 | 1.25 | -0.05 | 0.2 | PASS | NO | NORMAL | 1 |
| 5/19/2019 | 8:02:55 AM | REF1289765 | ISOP* | 1.3 | PPM ISOB.** | PID3459685 | 1.29 | -0.01 | 0.2 | PASS | NO | NORMAL | 1 |
| 5/19/2019 | 8:05:49 AM | REF1289765 | ISOP* | 1.3 | PPM ISOB.** | PID3459685 | 1.28 | -0.02 | 0.2 | PASS | NO | NORMAL | 1 |
| 5/19/2019 | 8:08:44 AM | REF1289765 | ISOP* | 1.3 | PPM ISOB.** | PID3459685 | 1.32 | 0.02 | 0.2 | PASS | NO | NORMAL | 1 |
| 5/19/2019 | 8:11:38 AM | REF1289765 | ISOP* | 1.3 | PPM ISOB.** | PID3459685 | 1.33 | 0.03 | 0.2 | PASS | NO | NORMAL | 1 |
| 5/19/2019 | 8:14:33 AM | REF1289765 | ISOP* | 1.3 | PPM ISOB.** | PID3459685 | 1.34 | 0.04 | 0.2 | PASS | NO | NORMAL | 1 |
| 5/19/2019 | 8:17:27 AM | REF1289765 | ISOP* | 1.3 | PPM ISOB.** | PID3459685 | 1.27 | -0.03 | 0.2 | PASS | NO | NORMAL | 1 |
| 5/19/2019 | 8:20:22 AM | REF1289765 | ISOP* | 1.3 | PPM ISOB.** | PID3459685 | 1.26 | -0.04 | 0.2 | PASS | NO | NORMAL | 1 |
| 5/19/2019 | 8:23:16 AM | REF1289765 | ISOP* | 1.3 | PPM ISOB.** | PID3459685 | 1.28 | -0.02 | 0.2 | PASS | NO | NORMAL | 1 |
| 5/19/2019 | 8:26:11 AM | REF1289765 | ISOP* | 1.3 | PPM ISOB.** | PID3459685 | 1.31 | 0.01 | 0.2 | PASS | NO | NORMAL | 1 |
| 5/19/2019 | 8:29:05 AM | REF1289765 | ISOP* | 1.3 | PPM ISOB.** | PID3459685 | 1.32 | 0.02 | 0.2 | PASS | NO | NORMAL | 1 |
| 5/19/2019 | 8:32:00 AM | REF1289765 | ISOP* | 1.3 | PPM ISOB.** | PID3459685 | 1.33 | 0.03 | 0.2 | PASS | NO | NORMAL | 1 |
| 5/19/2019 | 8:34:54 AM | REF1289765 | ISOP* | 1.3 | PPM ISOB.** | PID3459685 | 1.29 | -0.01 | 0.2 | PASS | NO | NORMAL | 1 |
| 5/19/2019 | 8:37:49 AM | REF1289765 | ISOP* | 1.3 | PPM ISOB.** | PID3459685 | 1.32 | 0.02 | 0.2 | PASS | NO | NORMAL | 1 |

*ISOPROPANOL  **PPM AS ISOBUTYLENE

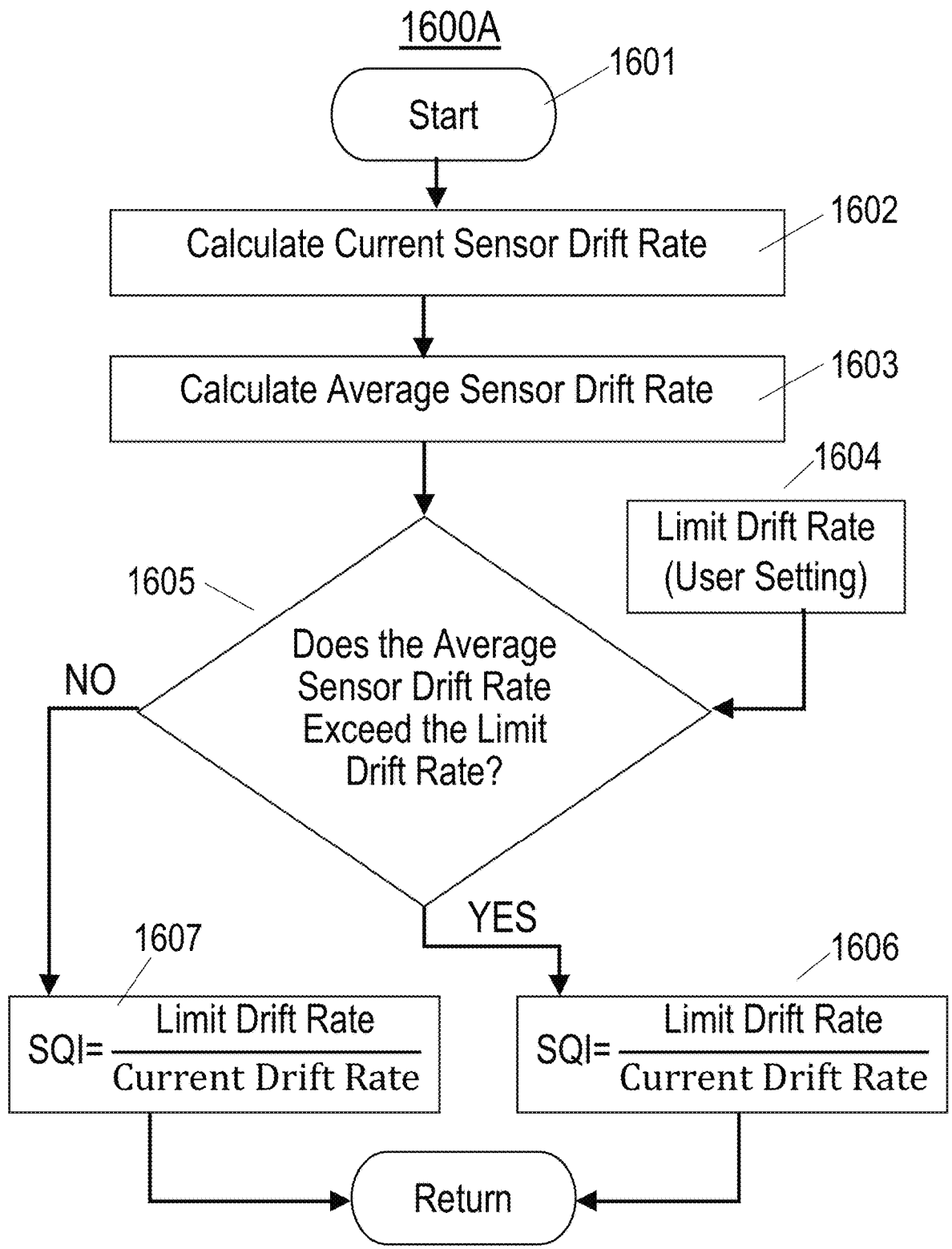

FIG. 16B

SQI Calculated for Severe
Exhaust Environment with PID

Limit Drift Rate (ppm/day) = 0.2
Sensor Tolerance (ppm) = 0.4

| Recalibration Events | Day # | Days Between Calibrations | Current Drift Rate (ppm/day) | Average Drift Rate (ppm/day) | Clamped Average Drift Rate (ppm/day) | Sensor Quality Indicator |
|---|---|---|---|---|---|---|
| 1 | 6.2 | 6.2 | 0.065 | 0.065 | 0.065 | 1.00 |
| 2 | 12.5 | 6.3 | 0.063 | 0.064 | 0.064 | 1.01 |
| 3 | 18.6 | 6.1 | 0.066 | 0.065 | 0.065 | 0.98 |
| 4 | 24.3 | 5.7 | 0.070 | 0.066 | 0.066 | 0.95 |
| 5 | 29.8 | 5.5 | 0.073 | 0.069 | 0.069 | 0.96 |
| 6 | 33.7 | 3.9 | 0.103 | 0.082 | 0.082 | 0.80 |
| 7 | 36.5 | 2.8 | 0.143 | 0.106 | 0.106 | 0.74 |
| 8 | 38.4 | 1.9 | 0.211 | 0.152 | 0.152 | 0.72 |
| 9 | 39.6 | 1.2 | 0.333 | 0.229 | 0.200 | 0.60 |
| 10 | 40.0 | 0.35 | 1.143 | 0.562 | 0.200 | 0.18 |
| 11 | 40.4 | 0.45 | 0.889 | 0.788 | 0.200 | 0.22 |
| 12 | 40.6 | 0.2 | 2.000 | 1.344 | 0.200 | 0.10 |
| 13 | 40.9 | 0.3 | 1.333 | 1.407 | 0.200 | 0.15 |
| 14 | 41.1 | 0.2 | 2.000 | 1.778 | 0.200 | 0.10 |
| 15 | 41.3 | 0.2 | 2.000 | 1.778 | 0.200 | 0.10 |

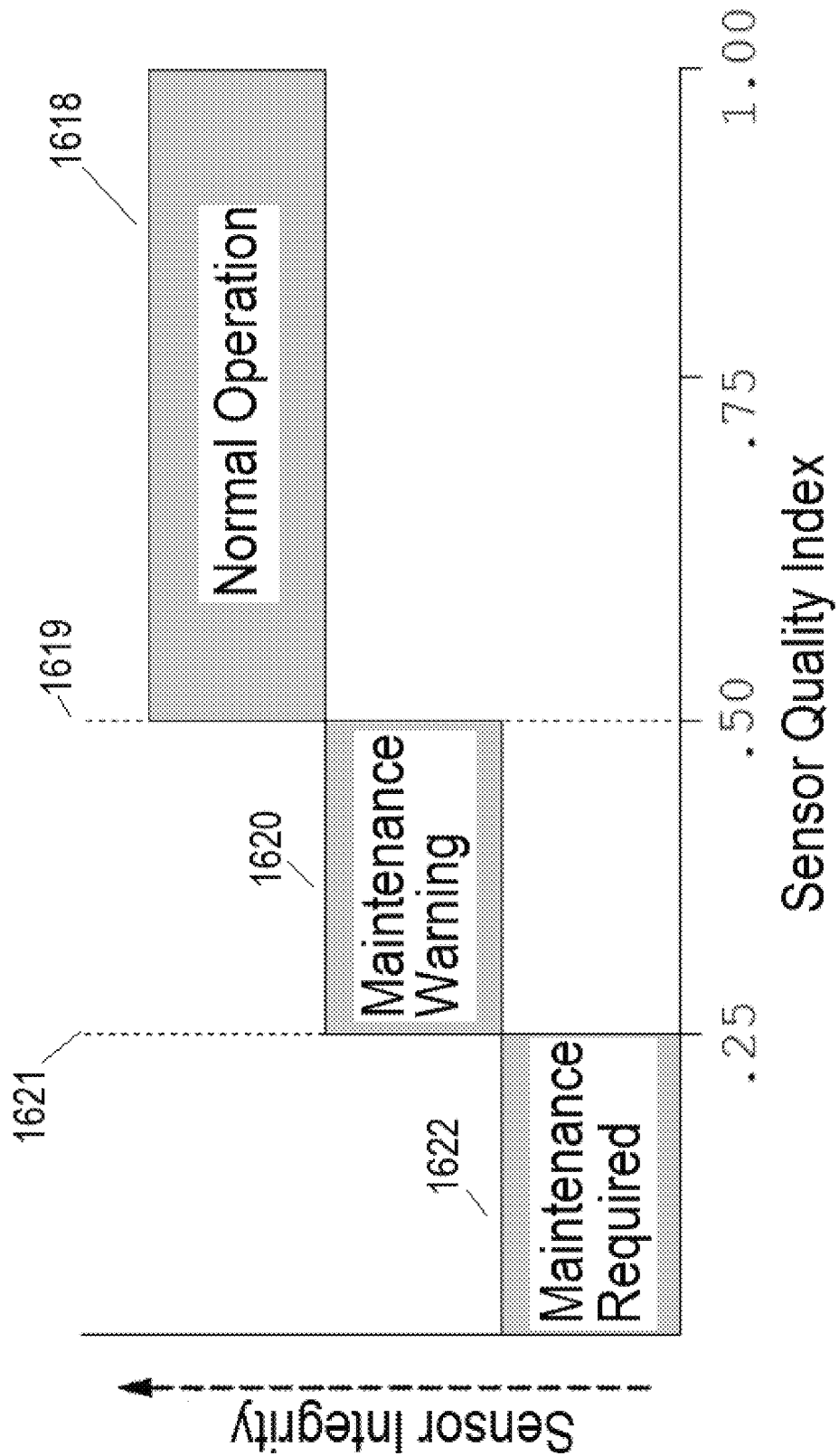

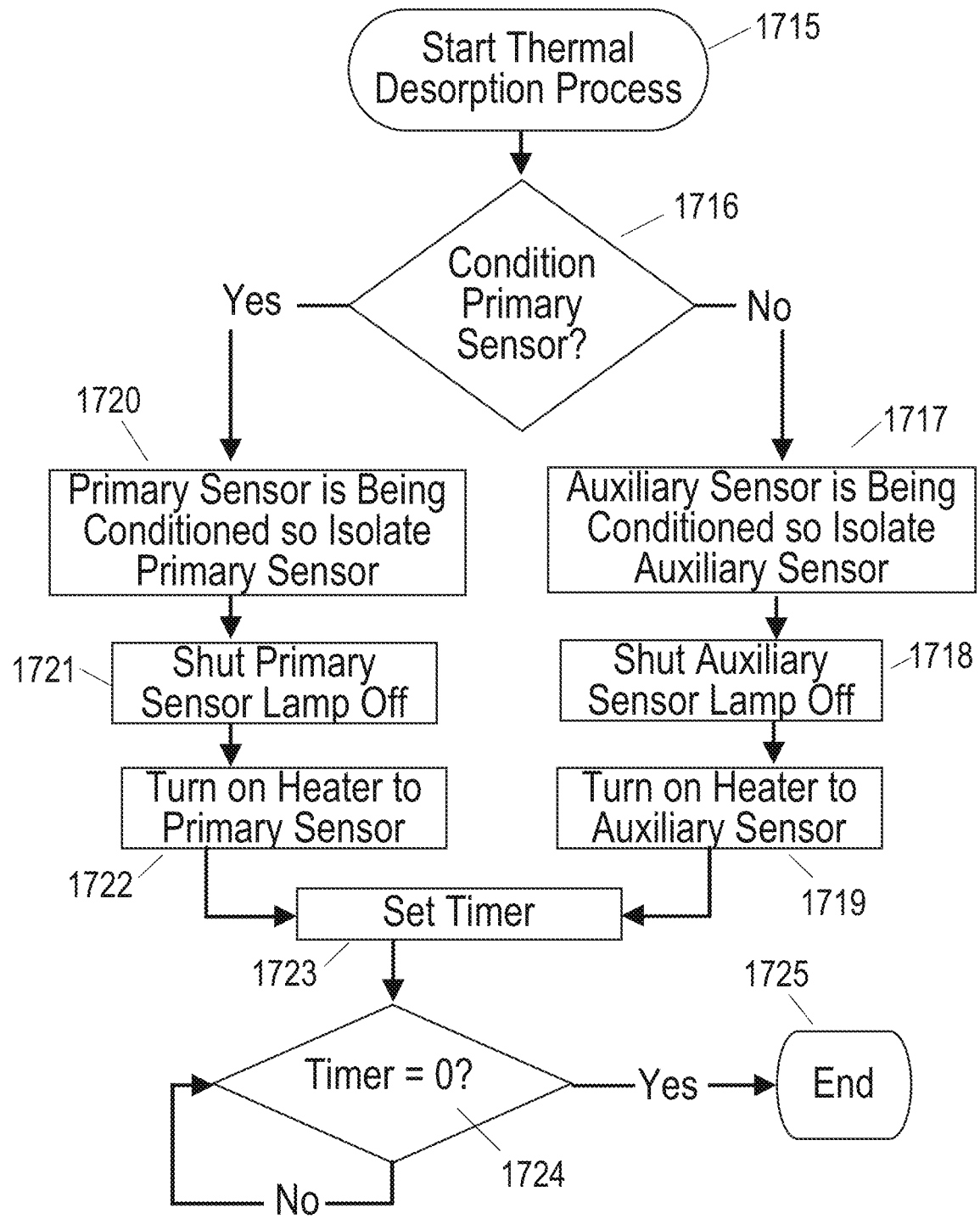

FIELD CALIBRATION FOR A MULTIPOINT AIR SAMPLING SYSTEM

CROSS REFERENCE TO RELATED APPLICATIONS

This application is a U.S. National Stage Application of International Application No. PCT/US2020/028045 filed in the English language on Apr. 14, 2020 and entitled "FIELD CALIBRATION FOR A MULTIPOINT AIR SAMPLING SYSTEM", which claims the benefit under 35 USC § 119 of U.S. Provisional Application No. 62/834,526 filed on Apr. 16, 2019, the disclosures of which are hereby incorporated by reference in their entirety.

FIELD OF THE INVENTION

The present invention relates generally to the energy efficient and safe operation of lab ventilation systems. More particularly, the invention relates to systems and methods for servicing and calibrating equipment used to monitor the presence of contaminants in exhaust air. Various aspects of the described systems and methods may be used within exhaust demand control applications.

BACKGROUND

Many facilities such as laboratories or critical areas requiring strict environmental monitoring and control, incorporate ventilation systems that are designed to safely support the use of chemical or biological compounds that have exposure limits. These limits can specify a range, threshold, or quantity of a compound such that, when the threshold, range or quantity is exceeded within an area, the health, comfort, and productivity of people within that area can be adversely affected. Examples of critical areas requiring this type of environmental control can include, but is not limited to facilities designed for research, education, experimentation, production operations, testing, health care, animal and pharmaceutical research, and other applications. In lab facilities, it has become increasingly common to apply environmental monitoring to measure contaminant levels in order to regulate aspects of the ventilation system's energy use while ensuring good indoor environmental quality ("IEQ"). Such environmental monitoring may include sensing a wide range of IEQ parameters, including but not limited to: airborne particulate matter, carbon dioxide ($CO_2$), carbon monoxide (CO), humidity levels, some acids and non-organic compounds, and a broad range of volatile organic compounds ("VOCs").

Exposure limits for most compounds used in labs have been established by various regulating and reporting agencies including the Occupational Safety and Health Administration ("OSHA"), the National Institute for Occupational Safety and Health ("NIOSH"), and the American Conference of Governmental Industrial Hygienists ("ACGIH"). ACGIH for example lists exposure limits for a wide range of compounds based on units of parts per million by volume ("ppmv"), but interchangeably as parts per million ("ppm"). Exposure limits listed by OSHA are often expressed as permissible exposure limits or PELs. ACGIH exposure limit values are often listed as guidelines, while OSHA exposure limit values are typically considered regulatory standard exposure limits.

The sensing of VOCs is especially important in lab applications, because many of the compounds which can become airborne at concentrations which can affect occupant health and comfort are higher vapor pressure compounds such as VOCs. When assessing the risk associated with using a specific compound (including VOCs and other compounds) in a lab setting, several factors are considered, including: the quantity of the substance that could be spilled; the surface area of a possible spill; the substance's vapor pressure; and the exposure limit or odor threshold of the substance. During a spill condition or accident, assuming the substance is in liquid form, the amount of surface area that said substance is spilled over may directly affect the quantity of the compound that becomes airborne due to evaporation. Therefore, when managing very toxic or odiferous compounds, quantity limitations may be set in order to limit the size of a spill's surface area. Compounds presenting the highest exposure risk are those which have the lowest exposure limit values while also having high vapor pressures. Most of these high exposure risk compounds are VOCs, however they may also include a few acids and other non-organic compounds which present high airborne exposure risks when spilled. For example, pure ammonia (a non-organic compound) has both a very low odor threshold of 5 ppm and, in its pure form, is a gas at room temperature. Even slight spills or leaks of ammonia would present an IEQ issue. Arsine is another non-organic compound that is a gas at room temperature and has one of the lowest exposure limits of all contaminants that may become airborne (i.e., 0.01 ppm).

When controlling an indoor environment, there is a conflicting relationship between energy use and good IEQ because improving IEQ generally requires more ventilation, which uses energy. Reduced ventilation and therefore energy use can result in poor IEQ, unless IEQ parameters in the controlled environment are properly sensed. Without reliable environmental monitoring or sensing, there can be a tendency to reduce energy use at the cost of poor IEQ. There are therefore notable risks associated with implementing environmental monitoring when sensing capabilities are not reliable. Furthermore, poor IEQ can have serious consequences to the health, comfort, and productivity of lab and building occupants.

A figure of merit that is sometimes used to describe ventilation levels in a room or area is the "air change rate", which is often measured as air changes per hour or ACH. This value is a measure of the number of times per hour the air in a room is fully replaced or exchanged with fresh new air.

Within the ventilation controls industry, the application of environmental monitoring (IEQ sensing) to control IEQ parameters is often referred to as active IEQ sensing (herein referred to as "active sensing"). IEQ sensing can be accomplished by installing discrete sensors installed within a building or location, or using centralized monitoring which includes confining activities to a single enclosure or common suite (i.e. the "main site") that contains one or more sensors that detect the compounds or parameters of interest. In the centralized monitoring approach, the sensors of the main site sense compounds or parameters in other locations that are remotely located from the main site using tubing and valves that communicatively connect the remote sites to the main site. Said tubing and valves may be sequenced in order to draw air samples from each remote location to form what is generally referred to as a multipoint air sampling system. Several of the advantages of using a multipoint air sampling system over a discrete sensor approach include but are not limited to superior measurement accuracy, ease of implementation, ease of sensor maintenance and lower initial sensor cost. Multipoint air sampling systems can be used to sense airborne IEQ parameters at many locations throughout a building, including rooms, corridors, lobbies, interstitial spaces, mechanical spaces, and some locations within ductwork and plenums.

There are two general types of multipoint air sampling system configurations, star-configured systems and distributed configuration systems. With the star-configured multipoint air sampling system, multiple tubes may be used to convey air samples from multiple locations to a centralized enclosure which contains the sampling valves, control electronics and software and the sensors used to sense airborne parameters. With distributed multipoint air sampling systems, the components of the multipoint air sampling system (especially the sampling valves) are distributed over a communication network, allowing for increased monitoring capacity as well as several other benefits.

FIG. 1 illustrates a prior art star-configured multipoint air sampling system. While the system of FIG. 1 shows a star-configured multipoint air sampling system that can sense up to four locations 103A, 103B, 103C, 103D, other star-configured multipoint air sampling systems may sense any number of locations, within a practical limit that is determined by the number of air sampling valves 104 that can fit within a single enclosure 101. The enclosure 101 contains sampling valves 104 which are sequenced using valve logic executed by a CPU 106 via an electronic interface 104E which provides discrete electrical connections to open and close each valve 104A, 104B, 104C, and 104D based on a desired air sampling sequence. One side of each solenoid valve 104A, 104B, 104C, and 104D is connected to an internal tubing backbone 109 which is used to convey each air sample from each monitored location through optional valving 105 so that airborne parameters in the air samples may be sensed by shared sensors 112. In some instances, for a given internal backbone 109, the air sampling sequence may involve one air sample per monitored location 103 at a given time. For example, as an air sample is taken from location 103A by opening valve 104A, valves 104B, 104C, 104D may remain closed. The star-configured multipoint air sampling system can contain more than one isolated backbone 109 to enable a faster overall sampling sequence by allowing the transport of a sample from a location other than 103A, 103B, 103C, 103D to be conveyed or setup while the shared sensor 112 senses a sample from one of the locations 103A, 103B, 103C or 103D. This approach or method can be referred to as an "alternating backbone" or "alternating limb" sampling technique.

In some star-configured multipoint air sampling systems, the process of obtaining an air sample from each location 103A, 103B, 103C, 103D involves two steps. First, an air sample from a desired location is transported at a higher flow rate than could be supported by the shared sensors 112, then the air sample flow rate is reduced to a lower flow rate that is more suitable for the shared sensors 112. The higher flow rate associated with the first step of the process is often referred to as the purge flow rate while the lower flow rate associated with the second step is often referred to as the sample flow rate. The purge flow rate is often a value of 10 times or more than the low flow rate. For example, an air sample may first be conveyed at a purge flow rate of 20 liters per minute from the monitored location and it may then be sensed at a flow rate of 2 liters per minute. Optional valving 105 is used to facilitate the switching between said purge and sample flow rates and is controlled by CPU/Valve Logic 106 in conjunction with flow control 114 which is responsible for regulating the air flow rates.

An example of a star-configured multipoint air sampling system is described in U.S. Pat. No. 6,241,950, which is incorporated herein by reference. Other types of systems known in the art of environmental monitoring include those that are designed to sense refrigerant gases and other related toxic gases. For example, the Bacharach® Multi-Zone Gas Monitor, which is a refrigerant monitoring system manufactured by Bacharach Inc., can be configured to sense halogens, ammonia, carbon dioxide and many other compounds, and is a star-configured multipoint air sampling system that can be applied to monitor up to 16 different locations. The MultiGard™ 5000, which is manufactured by MSA Safety Incorporated, can be configured to sense a broad range of refrigerant gases, carbon monoxide and other compounds, and is a star-configured multipoint air sampling system that can be applied to monitor up to 32 locations. Several of MSA Safety Inc. products incorporate photoacoustic infrared sensing for specialized sensing of refrigerant gases, including ammonia.

FIG. 2 illustrates a prior art depiction of a distributed configuration multipoint air sampling system. As can be seen from FIG. 2, the distributed configuration has all the elements of a star-configured multipoint air sampling system, but these elements such as valves 204A, 204B, 204C, 204D reside in a separate enclosure and valve assembly 217 that may be located separately from enclosure 201 which houses the shared sensors 212 and flow and valve logic. Enclosure 217 may incorporate one or more valves, and each enclosure 217 on the network connection 216 may have a different number of valves. One characteristic feature of a distributed configuration multipoint air sampling system is the use of an external common backbone 209 which may be used to connect to a number of air sampling valves both including and in addition to valves 204A, 204B, 204C, 204D. By locating valve assemblies like 217 using a common backbone 209, the amount of tubing 102A, 102B, 102C, 102D needed to span the distance between shared sensors 212 and the monitored locations 103A, 103B, 103C, 103D can be dramatically reduced, as compared to other systems that use a star-configuration multipoint air sampling system.

Another key feature of the system depicted in FIG. 2 is the network connection 216, which is used by the CPU/Valve logic 206 to communicate with the CPU 218 in order to remotely command valves 204A, 204B, 204C, 204D to move to their required state. To increase the overall number of locations which can be monitored by the system described in FIG. 2, more valve assemblies like 217 can be installed within the facility and connected to the network 216 and backbone 209. Because of the network 216, the distributed configuration multipoint air sampling system 200 is also referred to as a networked air sampling system. Another variation of a distributed configuration multipoint air sampling system involves using an information management server 220 to provide the sequencing logic to CPU 206, rather than maintaining such a program within the CPU/Valve Logic 206. The information management server 220 communicates with the CPU 206 via a network 219 that can be separate from network 216. In practice, networks 219 and 216 are implemented on what is known in the art as a RS485 physical layer, which is a robust digital communications protocol design for reliable operation over long distances within buildings. Network 219 can also be designed to support connections to other CPUs within other systems, thereby enabling the information management server 220 to remotely control a plurality of multipoint air sampling systems within a building.

An example of a distributed configuration multipoint air sampling system is described in U.S. Pat. No. 6,125,710, which is incorporated herein by reference. One example of a commercially available system that is a distributed configuration multipoint air sampling system is known as the Aircuity® system or OptiNet® system, made by Aircuity Inc. The Aircuity® system incorporates an Air Data Router which is similar to the components in the enclosure 217 described in FIG. 2, a sensor suite or SST product which is similar to the components within 201, and an information server or IMS, similar to the one illustrated in FIG. 2.

As shown in FIG. 2, tubing 102A, 102B, 102C, 102D can be connected to each location 103A, 103B, 103C, 103D by way of a duct probe element if the air sample is being taken from ductwork, or by way of a wall or ceiling mounted probe or aspiration device, if the air sample is being acquired from a room location. U.S. Pat. No. 7,421,911 B2, which is incorporated by reference herein, describes one such suitable duct probe for use with a multipoint air sampling system. Once an air sampling interval has been completed for location 103A, the system can then cycle again to obtain an air sample from the next designated location (location 103B for example). This air sampling sequence can continue until all locations 103A, 103B, 103C and 103D have been sampled.

Shared sensors 112 and 212 within FIGS. 1 and 2 may include one or a plurality of sensors. In some instances, these one or more sensors are "shared" because they are installed in one or more locations monitored and controlled by the multipoint air sampling system. This shared sensor approach provides great advantages over the use of discrete sensors installed within each location. A cost benefit of a shared sensor approach is that it reduces the number of sensors required to be purchased for each location. An additional benefit is the accuracy provided by a shared sensor approach and, in particular, to the fact that a shared sensor approach requires fewer sensors than a discrete sensor approach which facilitates the maintenance and calibration of the sensors. The maintenance benefit of a shared sensor approach includes reducing the number of sensors which need to be maintained which translates into a lower or reduced cost and labor associated with the maintenance. Sensor maintenance is a critical requirement for any sensor technology designed for IEQ monitoring because most sensors should be serviced and recalibrated every 6-12 months, even when monitoring relatively clean indoor environments. Another benefit that may be realized using a shared sensor approach, is that when a system provides IEQ sensing to multiple locations using discrete sensors in each location, the finite calibration related errors from each discrete sensor compound or stack together as each sensed value is compared to sensed values in a different location. This tolerance stacking is virtually eliminated with the shared sensor approach.

Multipoint air sampling systems, such as those described in FIGS. 1 and 2, are used for IEQ monitoring and active sensing in both lab and non-lab environments. Within the non-lab environment, such as for example office environments, a system 100 or 200 may incorporate any number of sensing options for shared sensors 112, 212 including but not limited to sensors for: airborne particulates; CO, $CO_2$; moisture; and TVOCs. Office environments have generally been viewed by engineers of ventilation systems as being less critical environments as compared to labs, in terms of the compound exposure risks to occupants and especially in terms of the energy savings benefits associated with active sensing, so sensing or active sensing applications which would involve the same breadth of sensing more commonly applied in labs is a less common application in non-lab settings. "Multi-parameter" demand control ventilation has nevertheless been used in non-lab spaces to regulate ventilation levels in order to achieve a healthier environment for occupants. Most non-lab environments are clean in terms of contaminant levels. Given the high level of air cleanliness seen in non-lab spaces, as a PID sensor is applied to multi-parameter demand control ventilation applications as one of shared sensors 112, 212 the PID can reliably detect many compounds or species at concentrations of a few tens of parts per billion and perform this function reliably over a period of many months.

One lab ventilation application where active sensing is applied using a multipoint air sampling system 100, 200 involves lab room or area-based demand control ventilation ("DCV"), or as referred to herein as Lab DCV. In Lab DCV applications, a multipoint air sampling system 100, 200 can be used to measure IEQ parameters within a lab space in order to control the air change rate of the lab space, based on the level of contaminants that are present within the lab. The measured IEQ parameters in Lab DCV applications can be sampled by system 100 or 200 at locations in the lab space that can be representative of the air that lab occupants are exposed to. These locations are referred to herein as "occupant breathing zones" and may be sampled by a system 100 or 200 from wall mounted probes or a duct probe which can be connected to the general exhaust exiting the lab space. General exhaust from a lab can be substantially representative of occupant breathing zone conditions, as the exhaust usually may not contain exhaust from fume hoods and other pollutant sources but may mostly comprise the air that is in the lab space itself or the occupant breathing zone's air. The sensing used in Lab DCV applications can include at least some form of volatile organic compound (VOC) sensing, but also may include sensing for a variety of other parameters, including but not limited to airborne particulate levels, carbon monoxide (CO), carbon dioxide ($CO_2$), and acid gas sensing. One of the sensor technologies commonly used to sense contaminants within a lab environment and used in many Lab DCV implementations is known in the art as the photoionization detector or PID.

The photoionization detector or PID is a commonly used sensor for lab IEQ monitoring because PIDs are highly sensitive and able to detect a very broad range of compounds that are often used in the lab environment. Although a PID cannot speciate or discern one gas compound from another, PIDs are often used in a variety of environmental health and safety applications because of their ability to detect hundreds of different compounds, especially VOCs. A PID can also detect a limited number of inorganic compounds including, for example, some of the higher risk non-organic compounds such as ammonia and arsine. U.S. Pat. No. 6,646,444, which is incorporated herein by reference, describes an exemplary PID used as one of the shared sensors 112 and 212 within systems such as system 100 or 200, respectively, as described in FIGS. 1 and 2.

One characteristic of a photoionization detector is that it can provide a signal that is substantially simultaneously responsive to multiple compounds. This simultaneous responsiveness is sometimes referred to as a "broadband" sensing characteristic. Other types of broadband sensors include but are not limited to metal oxide semiconductor (MOS) sensors, flame ionization detectors, and total organic compound (TOC) infrared sensors. With a PID, the photoionization can occur as a molecule absorbs a photon of energy at a sufficient level to release an electron to create a positive ion. This takes place when the ionization potential of the molecule in electron volts (eV) is less than the energy of the photon. A PID uses a specialized ultraviolet lamp as its photonic source, thus PIDs are sometimes used with lamps which operate at 10.6 eV because these lamps tend to be capable of detecting compounds in most occupant environments while also providing a broad detection range. As a compound is ionized by the lamp, electron flow is measured by a detector electrode, and this measured current is proportional to the concentration of the gas that has been ionized. Different compounds can be ionized at a given time thereby allowing a PID to be responsive to concentrations of multiple compounds. PIDs can be highly sensitive such that, when used in substantially clean environments, a PID can reliably detect many compounds at concentrations of a few tens of parts per billion and perform said detection with a high degree of reliability for a period of time lasting many months.

A PID can have different sensitivities to different compounds. This is known in the art as a response factor or "RF". Often a PID may be calibrated on a specific gas, such as isobutylene and the response factor of the PID to a particular compound may be referenced to its response to isobutylene. Response factors may vary slightly from one PID design to another. For example, a particular PID response factor for acetic acid is 11, which means that that particular PID's response to 1 part per million (ppm) of isobutylene is 11 times that of its response to 1 ppm of acetic acid. When this particular PID is exposed to 1 ppm of acetic acid, it may read 0.09 ppm in units of isobutylene. This is often described as a reading of "0.09 ppm as isobutylene". A response factor influences the sensor's ability to detect a compound at a given threshold. Detection can be limited for compounds that have a combination of very low TLV or odor thresholds and very high response factors. In the case of acetic acid, which has an odor threshold of 0.016 ppm, it would not likely be detected by the PID at its odor threshold because a reading would likely be 0.016 ppm divided by 11, or 0.0014 ppm as isobutylene, which is beyond the resolution of most PIDs.

The Lab DCV application can vary the air change rate of a lab room in direct proportion to the level of a sensed IEQ parameter that is present within said lab room. In some instances, it is common to operate the lab space at a minimum occupied air change rate of 4 air changes per hour ("ACH") when the lab is relatively free of IEQ contaminants, while in other instances, the DCV application can operate up to 10 ACH or even higher depending on the IEQ contaminant levels in the lab space and whether they reach a pre-determined threshold. During periods of time while the lab is unoccupied, the lab ACH value can be reduced to a minimum of 2 ACH via the above methods. Without active control provided via Lab DCV, lab minimum ACH values are often fixed to a value of 6 to 8 ACH, depending on the lab ventilation design. U.S. Pat. No. 8,147,302 B2, which is incorporated by reference herein, describes exemplary Lab DCV systems and methods, including those that use a differential IEQ measurement. Because most lab spaces are relatively free from contaminant levels, Lab DCV can enable reductions in fan energy and heating and cooling energy usage, as a result of reduced ventilation levels. It is well known in the art that labs are relatively free from contaminants more than 99% of the time. This fact is discussed in an ASHRAE Journal article "Demand-Based Control of Lab Air Change Rates" [Sharp, ASHRAE Journal, February 2010]. Given the high level of air cleanliness seen in labs, when a PID sensor is used in Lab DCV applications as one of shared sensors 112, 212 the PID can reliably detect many compounds at concentrations of a few tens of parts per billion and, in some instances, perform this function reliably over a period of many months. However, should the PID malfunction due to component failure or calibration drift, the Lab DCV application may deliver too much or too little ventilation, resulting in either energy waste or a potential IEQ problem.

Described in FIG. 3 is another prior art, lab-related, active sensing application known as exhaust demand control uses a multipoint air sampling system to monitor contaminant levels within duct risers connecting to the lab exhaust fan system in order to vary exhaust fan exit velocity based on whether lab exhaust air is contaminated or relatively clean. This multipoint air sampling system can provide an exhaust contaminant concentration signal that can be used to control the exhaust fans. Such an application can provide tremendous energy savings to exhaust fan systems by reducing the amount of bypass air used by the fan system when the lab exhaust is relatively clean. The exhaust demand control function can comprise CPU/Valve Logic 106 that provides a "setback" signal through the communication path 331 between the Fan Controls or BAS 332 and the CPU/Valve Logic 106 to the Fan Controls or BAS 332. This setback signal can be used to determine whether to reduce (or set back) the fan exit velocity of 328 by decreasing bypass air 325 when air streams 322A, 322B, 322C, 322D are relatively free of contaminants. Described in FIG. 3 are four exhaust risers 303A, 303B, 303C, 303D which connect to a common exhaust plenum 324. In this application, the exhaust fan systems may incorporate any number of risers, and the risers 303A, 303B, 303C, 303D can connect the air exhausts from any number of labs. Such risers 303A, 303B, 303C, 303D convey airflows 322A, 322B, 322C, 322D which may contain any combination of lab general exhaust, lab fume hood exhaust, and even exhaust from non-lab space. Exhaust fans 326A, 326B, 326C can be any type of exhaust fan however, FIG. 3 depicts a style of exhaust fan that is sometimes referred to as a high plume fan. As is known to those who have expertise with the application of lab exhaust fan systems, high plume fans are known for their ability to produce high effective plume heights while maintaining a relatively short physical profile. This is esthetically beneficial because the relatively short physical fan profile enables these fans, which sit on a roof 329 to not be as visible when compared to other larger exhaust stack alternatives. One characteristic shown in FIG. 3 that can be common to many exhaust fan systems is the presence of bypass air 325. In many lab exhaust systems, the exhaust airflows 322A, 322B, 322C, 322D may vary considerably over the course of a day for many reasons related to lab usage. This includes fume hood usage, temperature control functions and other factors which cause air change rate and therefore exhaust flows to vary in labs over time. One of the functions however performed by exhaust fans 326A, 326B, 326C is to ensure a minimum exit velocity of the flow rates 328 exiting each fan 326A, 326B, 326C. Typically, for example, without the application of exhaust demand control a target minimum exit velocity of 3000 feet per minute is desired for each fan 326A, 326B, 326C. As is known to those skilled in the art of lab ventilation, an exit velocity of 3000 feet per minute (fpm) is often specified based on guidance from ANSI Z9.5-2012. As lab flows 322A, 322B, 322C, 322D vary fan controls 332 may vary bypass air 325 in order to maintain this minimum exit velocity of 3000 feet per minute. Using active sensing to implement exhaust demand control, the bypass air 325 can be eliminated or reduced when contaminant levels in lab flows 322A, 322B, 322C, 322D are below a predetermined threshold, as determined by the sensing capabilities of shared sensors 112. In exhaust demand control applications, shared sensors 112 or 212 may include a PID sensor. Note that, although a star-configured multipoint air sampling system is depicted in FIG. 3, exhaust demand control can also be implemented using a distributed configuration, such as is described in FIG. 2. As shown in FIG. 3, interface 331 supports the communication between multipoint air sampling system 100 or 200 and the system 332 which is controlling the exhaust fan. Often, the interface 331 can be a simple relay contact that triggers at a point in time when the exhaust fans 326A, 326B, 326C and associated bypass air 325 may be reduced. In other applications, interface 331 may be a digital communications network such as for example a BACnet communications network.

As shown in FIG. 3, in the application of exhaust demand control the multipoint air sampling system can obtain air samples from each riser 303A, 303B, 303C, 303D via duct probes 330A, 330B, 330C, 330D and the air samples are processed based on the description of FIG. 1 and FIG. 2. Vacuum connection 115 shown in FIG. 3 can be a vacuum pump and, because of the potential contaminants present in the lab exhaust, the discharge of the vacuum pump associated with the vacuum connection 115 can be returned to one of the exhaust risers 303A, 303B, 303C, 303D via a dedicated tube and duct probe to prevent occupants from being exposed to the lab exhaust.

One characteristic of the lab exhaust air streams 322A, 322B, 322C, 322D (and lab exhaust in general) is that lab exhaust can create a harsh environment that can contain high concentrations of contaminants including various chemical compounds. The concentrations of the various chemical compounds in air streams 322A, 322B, 322C, 322D may amount to a value of up to 10,000 times the concentrations of similar chemical compounds found within the occupant breathing zone of a lab, and therefore may be up to 10,000 times higher in concentration than would be sensed by Lab DCV applications. Such chemical compounds may include inorganic compounds such as many acids, carbonates, cyanides, cyanates, pnictogen hydrides, and a broad array of organic compounds including but not limited to solvents, aromatics, ketones and aldehydes, amines and amides, chlorinated hydrocarbons, sulfur compounds unsaturated hydrocarbons and alcohols. Contaminant concentrations may periodically be high in lab exhaust when at least a portion of lab exhaust air streams 322A, 322B, 322C, 322D contain fume hood exhaust or exhaust from other types of potentially high contaminant sources including but not limited to: canopy hoods, biosafety cabinets, animal holding rooms, necropsy areas, animal cage racks, ventilated chemical cabinets, acid digestion stations or Kjeldahl equipment, and outputs from equipment such as gas chromatographs.

Because of the very high contaminant levels seen in exhaust demand control applications, the chemical exposure realized by shared sensors can be severe as compared to Lab DCV applications. This chemical exposure can lead to drift and calibration issues with the shared sensors caused by sensor fouling and degradation. One of the sensors that is often used as a shared sensor in exhaust demand control applications is a PID and one mode of PID drift that is common with overexposure to contaminant levels is that of a decrease in the PID sensor's sensitivity over time. When a PID has drifted sufficiently in this manner, the associated systems using the PID may not be sufficiently responsive so as to ensure that the necessary exit velocity of exhaust from fans 326A, 326B, 326C may be achieved when air streams 322A, 322B, 322C, 322D are contaminated. Failure to deliver the necessary exit velocity can cause issues with the exhaust plume height and the resultant dispersion performance of the fan system. As a result, lab contaminants may not be properly dispersed from exhaust fan system 300 which could result in contaminants becoming entrained into outside air intakes and other receptor points around the lab building or around buildings which are adjacent to the lab building associated with fans 326A, 326B, 326C. This entrainment of contaminants can create serious issues with building occupant health, comfort, and productivity.

U.S. application Ser. No. 16/141,109, which is incorporated herein by reference, describes a prior art, improved multipoint air sampling system and methods for implementing exhaust demand control. This improved multipoint air sampling system significantly reduces sensor calibration drift or degradation by implementing a "sensor protective mode" which can isolate shared sensors when measured contaminant levels exceed a predetermined threshold. This type of system makes it possible to operate shared sensors while monitoring harsh lab exhaust environments such as air streams 322A, 322B, 322C, 322D for many months of operation without having to provide maintenance or calibration to the shared sensors. Despite the advantages of this system, sensor fouling and drift are still possible in situations where contaminant levels in air streams 322A, 322B, 322C, 322D are pronounced.

Also, and as is especially the case with PID sensors, there is some probability of sensor drift or even a transition to a state where the sensor is no longer responsive that can occur even when the sensor is used in relatively contaminant free air. As those skilled in the art of electronics may recognize, there is some probability of failure with electronic components, both including and beyond what's known in the art of electronics as infant mortality, such that every device has a probability of failure during its normal operating life. For devices like PID sensors, however, the mean time to failure is a relatively short as compared to other electronic components. The MTTF of a PID sensor may be eight months, because of the reliability and drift stability of the sensor elements themselves. By comparison, the MTTF for common electronic parts such as capacitors may be 20 to 30 years. It is therefore desirable to minimize the impact that sensor failures may have on the overall system, especially by mitigating the impact on occupant safety and energy use.

A condition that can arise with exhaust demand control applications relates to behavioral aspects of lab occupants and facility and health and safety managers in the event of a large chemical spill leading to perceived malfunctions with a multipoint air sampling system such as the system described in FIG. 3. Many labs have a chemical inventory of compounds which are so toxic or odiferous that a quantity limitation protocol must be applied to the use of the compounds to ensure that the exhaust fans can provide enough dilution in the event of a spill of each compound. The most common scenario which may lead to facility staff questioning the integrity of a multipoint air sampling system can be a spill condition involving highly odiferous compounds, because this type of event can lead to odors that are re-entrained into the building's ventilation system such that occupants are repeatedly exposed to the odors. For example, ethyl mercaptan, a compound found in many lab inventories, has an extremely low odor threshold on the order of 0.001 ppm, and has a very unpleasant "rotten eggs" smell. By comparison, many less odiferous and less toxic compounds (such as hexene for example) can be used in lab spaces in 1-liter quantities, while ethyl mercaptan is normally limited to approximately 5 to 10 milliliters. However, this requirement may pose an inconvenience to lab researchers who may disagree with the low quantity protocol, which can be hard to enforce. As a result, researchers may break from the usage protocol and use more of the compound than a fan system 300 can handle when there is a spill of the compound. When an eventual spill occurs, the lab building and its surroundings may be impacted by unpleasant smells thereby leading to questions about the integrity of the multipoint sampling system that is providing exhaust demand control.

It has been common practice for manufacturers of environmental monitoring systems such as multipoint air sampling systems to provide methods of remotely monitoring the general status of the operation of these systems. This may be accomplished for example using an interface to the building automation system (BAS) such as the interface 331 described in FIGS. 3, which may use any number of digital communications methods such as for example BACnet, Lon Works, or some other building automation protocol. Remote monitoring may also be accomplished using an internet connection 321 to a remote data center or cloud-based application. These methods of remote monitoring can verify the general operation of a shared sensor by observing actual sensor data over time. This sensor data may include the logged sensor measurements (of air streams 322A, 322B, 322C, 322D, for example) over periods of time in order to look for data patterns which may be indications of calibration drift or other possible sensor failures. Using this technique (which is also known as "Proactive Monitoring") can be valuable, however, it often does not provide definitive proof that sensors are working properly. For example, when observing VOC sensor data (such as data from a PID sensor) associated with lab environments that experience long periods of time where the lab air (including that of air streams 322A, 322B, 322C, 322D) may be relatively free of contaminants; a VOC sensor reading may be zero. During these periods of time, which may be several days in duration, one may not be able to conclude that the one or more VOC sensors are malfunctioning just because they are reading zero. If Proactive Monitoring were used, it may be possible to apply logic which can signal an alarm should no finite readings above zero from the sensors be observed over extended periods of time. While Proactive Monitoring may be beneficial for these sensors, in other cases, especially in critical applications such as exhaust demand control, a recognition lag of several days to identify a sensor failure is generally unacceptable.

Typically, the sensors used in Lab DCV or exhaust demand control applications are maintained via a field replacement service often provided by the manufacturer of the multipoint air sampling system. An objective of the sensor replacement service is to replace the sensors before their calibration has expired. Such service is typically scheduled to occur on 6-month intervals. When sensors are replaced, the sensors which have been removed are shipped back to the manufacturer's facility for service and calibration. The field work of swapping out these sensors is performed by a factory trained technician that either works directly for the manufacturer or is a technician who works for the manufacturer's representative. These technicians are usually also the individuals who must travel to the lab building location to address other types of maintenance and service for systems such as those described in FIGS. 1, 2 and 3. Because of demand for these factory trained technicians and the sometimes-large territories that the manufacturer's reps must cover, it is not uncommon for the sensor replacement service to not occur on time. This is a serious issue for critical applications such as exhaust demand control, where a lack of on-time sensor maintenance can result in system malfunctions due to sensor drift or failure.

Some refrigerant monitor type multipoint air sampling systems provide a method of enabling technicians to field calibrate the system's sensors using a calibration gas, or gas standard. For example, the Chillgard® 5000, by MSA Safety Incorporated is a refrigerant monitor that integrates the calibration process within a touchscreen menu, enabling the system to run a span calibration, using cylinder gas as a span calibration source. Because the purpose of the Chillgard® 5000 is to detect refrigerant gases, as a calibration gas it uses Tetrafluoroethane, which those who are experienced in the art of refrigeration may recognize as a common refrigerant gas (sometimes referred to as synthetic R-134).

The application of cylinder gas (gas stored under high pressure in a metal bottle) to field calibrate a PID used as sensors to sense harsh environments can be problematic. When monitoring lab exhaust with a PID, the PID may become fouled over time due to the sensor's exposure to the many possible highly adsorptive compounds common in the lab exhaust 322A, 322B, 322C, 322D. The effects on sensor accuracy due to this fouling may not be apparent as a cylinder gas is applied to verify the calibration of the PID because of the lack of moisture in the cylinder gas. Most cylinder gases are devoid of any moisture, both to protect the cylinder vessel from corrosion and to ensure the purity and mixability of the calibration gas, so that it may be used as a standard. However, when a PID sensor has been heavily fouled with certain adsorptive compounds, its response may be enhanced or reduced by gas phase moisture, depending on the type of compound which has fouled the sensor. For example, PIDs can become fouled when overexposed to ammonia and usually this results in the PIDs' reading being enhanced when in the presence of moisture. FIG. 4 is a prior art illustration of the basic components of a typical PID sensor, which includes a high-intensity ultraviolet lamp 402, that can be energized by a high frequency source. Such lamp 402 emits UV energy 410 at a specific energy level in order to ionize molecules 404 of the analyzed gas. Such ionization may occur if the molecule 404 has an ionization potential that is less than the ionization energy 410 of the lamp 402. As a molecule 404 becomes ionized it becomes charge imbalanced, which causes it to become attracted to collector electrode 405, due to the electric field that is set up between high voltage grid 403 and collector 405. As ionized molecules 404 are attracted to electrode 405, a small current may flow that is detected by amplifier 406, which provides an output 407 in direct relation to this current and therefore the concentration of the molecules 404. In order to provide good sensitivity, the high voltage grid 403 and collector electrode 405 can be extended through an electrode stack which includes alternating layers 408 of high voltage grid 403 and alternating layers 409 of collector electrode 405. These layers may be built up on a porous multilayer circuit board resulting in gap distances between 409 and 408 that are only fractions of a millimeter. Under controlled conditions, the PID 400 can be calibrated using an inert gas such as isobutylene. When calibrated on isobutylene, the sensor's reading is often referenced to units of ppm "as isobutylene".

When a PID is overexposed by adsorptive gases, such as those compounds which are highly polar and may tend to more readily attract and stick to surfaces of materials due to Van der Waals forces and hydrogen bonding, the adsorptive compound may adhere to electrode stack 408, 409 in such a way that it creates a uniform coating which connects between the electrode stack. Such a coating from the adsorptive substance may have no effect on an output signal 407 of the PID when humidity levels are sufficiently low (such as when exposed to cylinder gas). However, some compounds, when absorbed and bridging between the electrode stack, may exhibit an electrical impedance that may vary with humidity. For example, when a PID has been overexposed by ammonia, the PID sensor output 407 may read high in the presence of high humidity levels and, in this case, the PID sensor 400 can overestimate the actual levels of contaminants present in for example air streams 322A, 322B, 322C, 322D. Under such circumstances, the PID 400 may exhibit a reading of several ppm as isobutylene (a large percentage of the full calibration span of the sensor) even though no contaminants are present. This same sensor 400, when checked in the field by administering cylinder gas, such as isobutylene, may nevertheless appear to be in calibration even though it is not performing properly. Alternatively, as sensor 400 is returned to the manufacturer as a part of the field replacement service previously discussed, said service would typically include cleaning or replacing the electrodes 408, 409 before recalibrating the sensor 400.

Other practical issues with using cylinder gases in the field include restrictions on air freight shipment and delays that can arise when attempting to provide in-field service using a calibration gas that is in a cylinder. Compressed gas cylinders must be shipped via ground shipping which can pose serious logistics issues, such as a field technician that must travel by air not being allowed to take the calibration gas with them to the field site as they fly to that location. Rather, the field technician has to ship the cylinder gas by way of ground shipping to the site, which can often take one or more weeks.

Another issue with cylinder gas is that it is relatively expensive. For example, a standard 17-liter disposable steel cylinder of NIST traceable isobutylene costs about $50 U.S. dollars. A cylinder such as this is adequate for calibrating only 2 or 3 sensors in the field, so it is likely that several cylinders are required per field visit to calibrate all the sensors in a system. Refillable gas cylinders can be used; however, such cylinders are heavy and not suited for field service work. Using disposable gas cylinders is not an environmentally friendly solution because it creates waste.

In labs a common source of high concentrations of ammonia is from animal holding areas or vivarium suites in which animals such as mice, rats, non-human primates, and many other types of animals are kept. Where animals are held, ammonia is generated constantly and exists at varying concentrations as a result of microbial decomposition of animal waste. Ammonia levels are generally lowest right after caging an animal or after an animal holding space has been cleaned after which concentrations will grow until the space is cleaned once again. Ammonia levels are difficult to sense over time because of sensor drift. A PID sensor is responsive to ammonia but may foul and drift with as little as a couple weeks of exposure to a typical animal holding facility. U.S. Pat. No. 9,651,531 B2, which is incorporated herein by reference, describes a method of using two PID sensors with UV lamps of different ionization energies combined with an enhanced response factor to discriminate ammonia from other compounds. This technique can be effective for measuring ammonia concentrations within animal spaces if the calibration of each PID is maintained. The method is not effective in detecting ammonia in spaces having high concentrations of compounds with high ionization potentials. Using this technique, these high ionization potential compounds may be incorrectly identified as ammonia because the comparative PID approach does not sufficiently speciate against interfering compounds with high ionization potentials.

Sensors which are highly selective and primarily responsive to a specific compound are sometimes referred to as "speciating sensors" because they are primarily responsive to one particular species or compound. Many speciating sensor technologies, such as electrochemical sensor technologies, also may respond to some interfering compounds which may not affect the sensor's intended purpose. Some speciating sensors are capable of simultaneously sensing multiple compounds at once. These types of speciating sensors, such as gas chromatographs for example, tend to be quite sophisticated and are generally not used in multipoint air sampling systems because of the cost and because of the environmental conditions required to operate such sensors.

One speciating sensor involves ammonia sensing using electrochemical sensor technology. Such a speciating sensor can be effective at detecting ammonia because electrochemical detectors are highly specific to what they respond to, however, the field life of an electrochemical sensor can be somewhat limited when ammonia concentrations are high on an average basis. Electrochemical sensors often have a field life that's proportional to a predetermined ppm-hours rating. For example, a typical electrochemical sensor may have a field life of 6000 hours at 1 ppm (6000 ppm hours). In a typical vivarium or animal holding facility average ammonia levels in the exhaust, such as the air streams 322A, 322B, 322C, 322D may reach peak values of 10 ppm or more. If the average ppm reading in exhaust air streams were 10 ppm, an electrochemical ammonia sensor used for this purpose may be expected to have a field life of 600 hours (10 ppm*600 hours, or 6000 ppm hours), or only 25 days. However, average values of ammonia in exhaust an air streams are usually lower than 10 ppm, due to the cyclic nature of ammonia concentrations in animal facilities that corresponds to the cleaning cycles of cages and bedding areas, a cycle which is often a week in duration. Ammonia levels may be near zero ppm immediately following cage cleaning, but then gradually rise as the cages become soiled.

The exhaust demand control system usually incorporates a PID sensor because of its broad detection capabilities including the detection of a wide range of compounds (herein "high dilution compounds") that may require the full dilution capability of the fans when a spill occurs, but also includes a wide range of compounds (herein "low dilution compounds") which may be equivalently detected by sensors but which do not require much dilution from exhaust fans because the low dilution compounds are not very odiferous or toxic. Again, the PID often cannot discern or speciate one compound from another. For example, when a system is used to provide exhaust demand control to labs that include animal holding rooms, cages or in general vivarium spaces, even high levels of ammonia from vivariums can easily be diluted by exhaust fans because the odor threshold and toxic limit value of ammonia are relatively high. The PID of the system, however, is responsive to ammonia and this may result in the CPU/Valve Logic 106, 206 commanding Fan Controls or a BAS to set back the fans even though only ammonia is present in the airstreams. For example, ammonia levels may on average be 10 ppm in airstreams and to remove odors, such concentrations of ammonia would only have to be diluted by a factor of 10 by exhaust fans. Such dilution by a factor of 10 can be accomplished at practically any exit velocity assuming that the fans can provide no less than several hundred to one dilution, even at minimum exit velocities. The presence of ammonia in an airstream can result in a scenario in which the fans may not set back, thereby resulting in energy waste.

Another type of calibration gas source or standard involves a permeation source or gas permeation device. Gas permeation devices have been used for decades as calibration standards for specialized gas sensor instruments generally intended for sensing trace levels of gases (e.g. concentrations in the range of parts per billion—ppb—or parts per trillion—ppt—) or gases which are too toxic or too reactive to store in a gas cylinder. For example, gas permeation devices are often used to calibrate gas chromatographs and other types of sensitive gas analyzers. One common type of permeation device is a permeation tube, which is illustrated in FIG. 5A, and is intended to operate within what's known in the art as a "permeation oven". A permeation tube assembly 500A is a simple device that's composed of a hollow tube 501 that is filled with a liquid 506 of interest to generate a gas 503 at a known temperature. The gas 503 is a single compound or species of gas. The permeation tube is usually made of a fluoropolymer such as polytetrafluoroethylene (PTFE) or it is made of fluorinated ethylene propylene (FEP). Endcaps 502 are used to seal the tube 501 and they are usually made of PTFE or FEP as well. PTFE or FEP are frequently used in assembly 500A because of their chemical resistance, given the types of compounds 506 that would normally require a permeation method, as opposed to a gas standard in a pressurized cylinder for example. PTFE and FEP are also known to support the gas phase permeation of many compounds. Gas permeation is the process where the vapors from a permeate can penetrate a solid due to the presence of a concentration gradient of the permeate between one side of the solid and the other. This concentration gradient is a function of the partial pressure of the gas (the vapor pressure) that is created about the liquid, which is a function of the temperature of the liquid. Every compound has different vapor pressure properties and again, these vapor pressure values vary with temperature. However, if the temperature of liquid 506 is maintained in a precise manner, then the rate at which gas 503 permeates may be relatively constant. The permeation rate of 503 can vary considerably with the temperature of liquid 506 and for different compounds used as 506 but, generally, permeation rates are relatively low (on the order of nanograms per minute or even picograms per minute). For a given permeation rate of 503, the ppm concentration of the gas 503 that is external from the tube 501 can be a function of the flow rate of the carrier gas 505. The carrier gas 505 can be an inert gas such as nitrogen, however, clean dry air (often called "zero air") may also be used. Such carrier gases are usually delivered from a compressed gas cylinder.

The permeation tube described in FIG. 5A is used in a controlled environment (usually in a metrology laboratory) where it is held within a permeation oven, which serves the functions of maintaining the liquid 506 at a precise temperature and controlling the flow rate of the carrier gas 505 over the tube 501. Depending on the compound, the permeation oven may usually operate at 180 degrees Fahrenheit or more. An example of such a permeation oven is the OVG-4 by Owelstone® Inc. Permeation rates are not only a function of the vapor pressure of the liquid 506 but they are also a function of the properties of tubing 501, including the tube's material (PTFE, FEP, for example), the tubing wall thickness, and the overall inner surface area of the tubing which is in communication with the vapor from the liquid 506. Said inner surface area of tubing which is in communication with the vapor from the liquid can include the portion of the tubing 501 which is in communication with the liquid 506.

Therefore, as the liquid 506 evaporates the permeation rate (nanograms per minute) of gas can be constant if the temperature of the liquid 506 is held constant.

However, in practice each permeation tube assembly can provide a different permeation rate at a given temperature due to subtleties in the wall thickness of the tubing, as well as the length of the tubing and the slight variations in the chemistry of the compound 506. Before a permeation tube can be used, it can be characterized, by operating the tube in an oven for several days or several weeks and measuring the mass of the tube 501 and compound/liquid 506 before and after this process. This process is often referred to as permeation tube calibration, even though it is a characterization process. The mass difference between the start and the end of this characterization process divided by the duration of the process determines the permeation rate, or calibration, of the tubing assembly at a specified temperature.

The gas permeation approach described with respect to FIG. 5A may be used with hundreds of possible compounds, however this approach is often reserved for laboratory applications or applications where a gas analyzer that is designed to measure hazardous or reactive compounds must be calibrated. The reason for this is that calibration of a permeation tube is time consuming and the setup including a permeation oven is expensive.

Described in FIG. 5B is another type of prior art, gas permeation device known as an immersion tube source, which is intended for providing higher permeation rates than the simple permeation tube assembly described in FIG. 5A. An immersion tube source places the permeate 513 (herein permeation liquid) on the outside of a permeable tube 508 in order to maximize the surface area of the tubing 508 that is in communication with the vapor from the permeation liquid 513 that is held within the vessel 512 that is sealed by cover 511. The cover 511 can provide a gas tight passage for tubing 508 and the carrier gas can then be flowed through the tubing at a substantially precise flow rate, while the permeation liquid 513 can be held at a fixed temperature to establish a fixed concentration of the gas from liquid 513. The immersion tube source 500B can be larger in size than the permeation tube described in FIG. 5A, because of the greater amount of tubing 508 which must be contained within the vessel 512. Depending on the vapor pressure of the permeation liquid 513, an immersion tube source can permeate at a rate of up to a few tenths of a microgram per minute or more, such that it can permeate at rates several orders of magnitude higher than the output of a permeation tube described in FIG. 5A. However, the immersion tube source described in FIG. 5B may still be maintained under precise temperature control to serve as a reliable gas standard and the larger size of the tube assembly described in FIG. 5B makes this act difficult if not hazardous, especially if held at the higher temperatures of 180 degrees Fahrenheit or more, which are temperatures generally required for maintaining such a source. This system can require an elaborate apparatus and setup within a controlled environment.

U.S. Pat. No. 4,399,942, which is incorporated herein by reference, describes a permeation source that is potentially more compact than the immersion tube source described in FIG. 5B. This immersion tube source incorporates a partially gas-phase chamber in addition to a liquid-phase chamber, where the two chambers are separated by a silicone polymeric compound. The presence of even trace amounts of silicone in a calibration gas stream for some types of TVOC sensors, such as metal oxide semiconductor MOS sensors can lead to premature sensor failure due to the incompatibility of silicones with the tin and other oxide layers found in MOS sensors. In addition, silicone is highly adsorptive, which can make controlling the gas output of such a permeation source problematic. Much benefit can be derived from using a lower operating temperature for the device.

BRIEF DESCRIPTION OF THE DRAWINGS

The foregoing features may be more fully understood from the following description of the drawings.

FIG. 7 illustrates an embodiment of a field reference subsystem.

FIG. 15 illustrates an embodiment of an evidence log with record content.

FIG. 16A illustrates an embodiment of a process to generate SQI values for sensor(s).

FIG. 16B illustrates an embodiment of a table of SQI calculations.

FIG. 16C illustrates embodiments of rules logic for different reporting levels based on SQI values.

FIG. 17B illustrates an embodiment of a thermal desorption sequence for a sensor.

DETAILED DESCRIPTION

The present invention provides methods and systems which can significantly improve the service, reliability, and validation of a multipoint air sampling system used to sample air, monitor and improve air quality in harsh lab environments. The capabilities incorporated within these methods and systems provide dramatic improvements to the safety, energy savings, and maintainability of this type of air sampling and air quality control application. In some instances, the methods and systems described herein can be used in exhaust demand control applications.

Exemplary embodiments of the described methods and systems provide a multipoint air sampling system that incorporates a field reference subsystem to generate one or more test gasses or species to at least test or validate one or more sensors associated with the multipoint air sampling system. Other embodiments not only test the one or more sensors associated with the multipoint air sampling system, but also provide reporting actions such as but not limited to service and alarm reporting. Other embodiments additionally provide corrective actions such as but not limited to the calibration of said one or more sensors as needed. Further embodiments include service and evidence recording and communication functions. Other embodiments utilize said field reference subsystem to reject certain interfering low dilution compounds from compounds which must be detected. Further embodiments utilize said field reference subsystem to determine situations where the accuracy of the one or more sensors of the multipoint air sampling system is degraded by a fouling condition and, in embodiments, provides methods of enacting field conditioning measures of said one or more sensors in order to return said sensors to a usable state.

Figure 1:
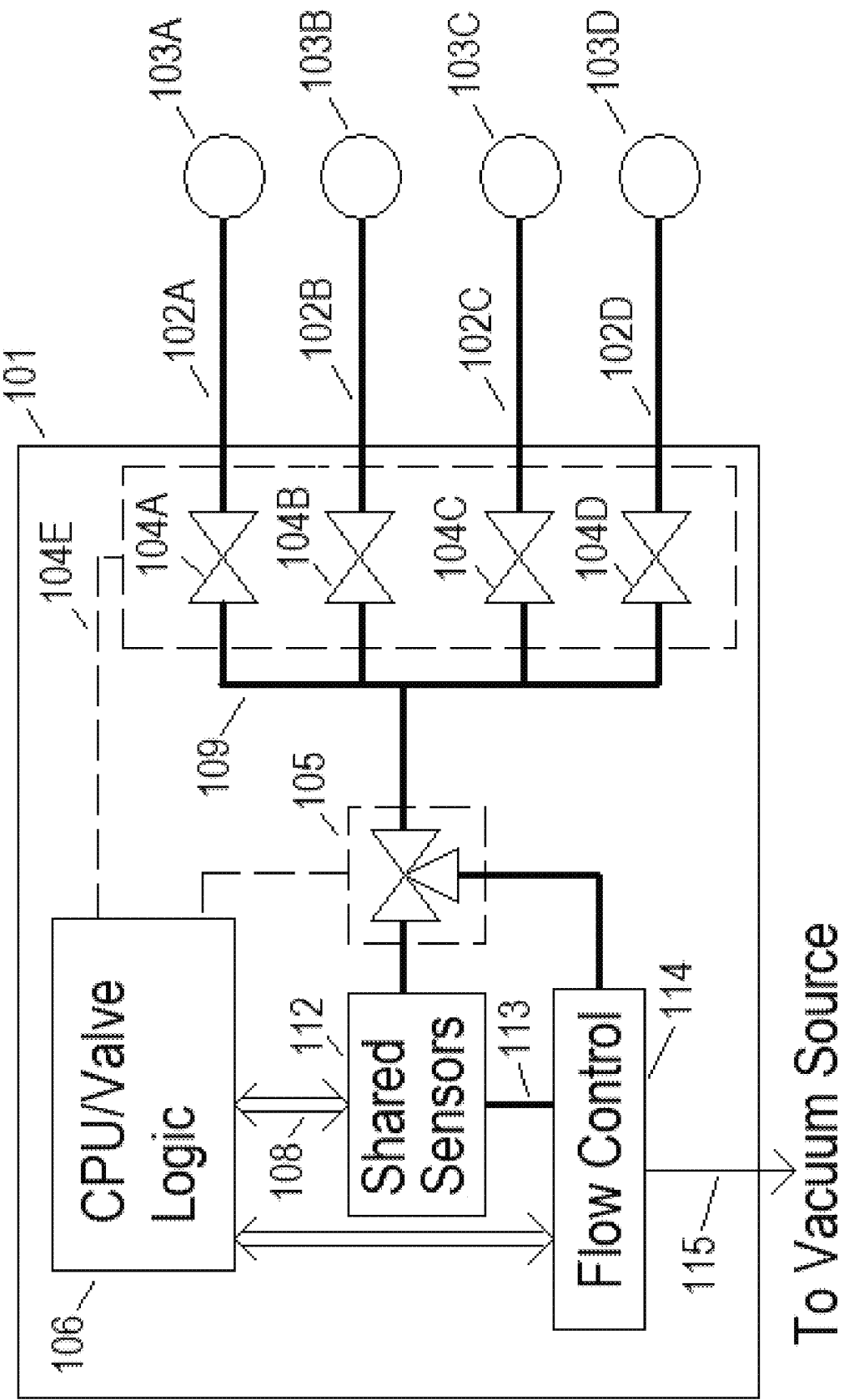
FIG. 1 illustrates an example of a prior art system of a star-configured multipoint air sampling system.
Figure 2:
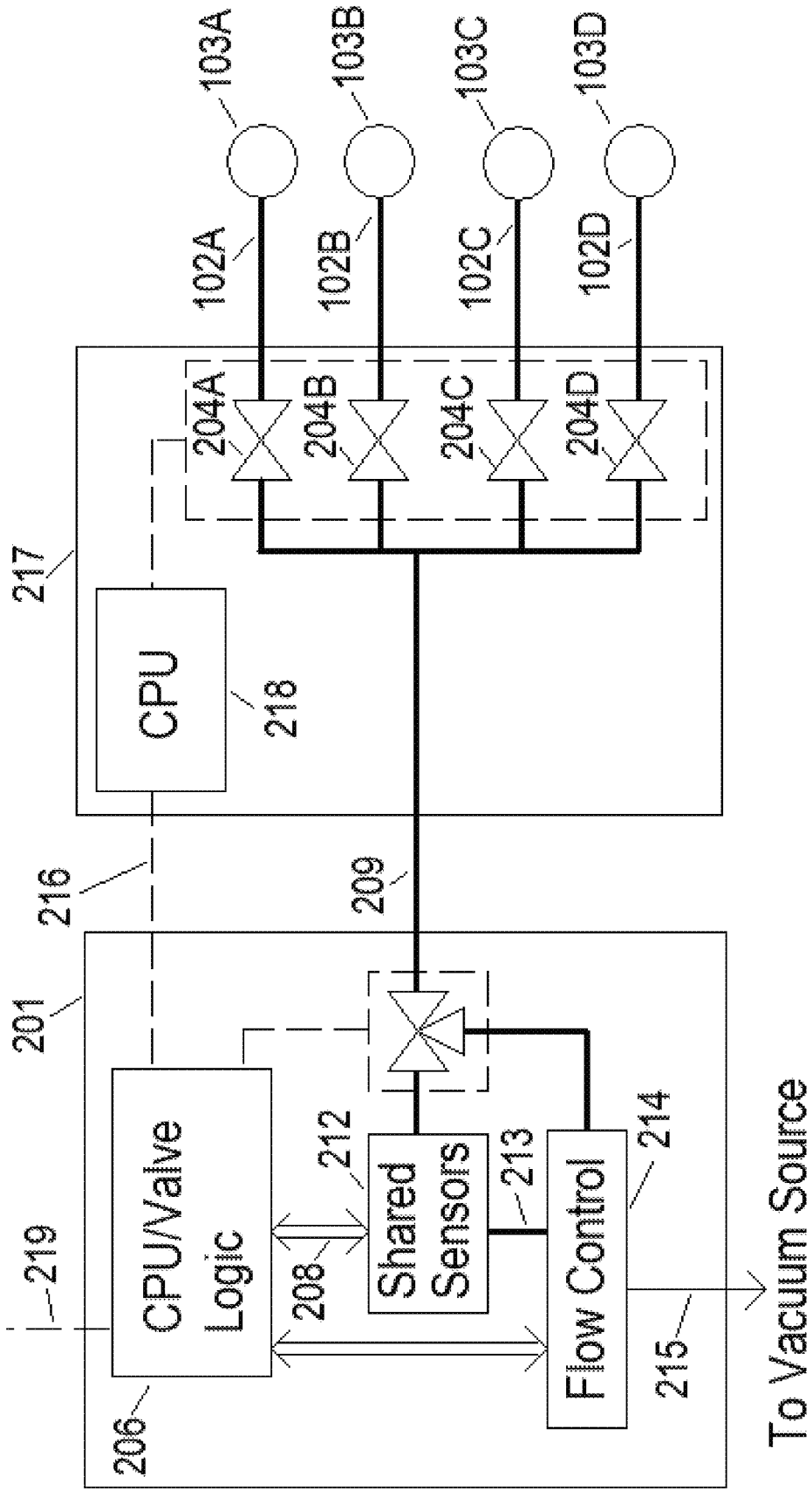
FIG. 2 illustrates an example of prior art system of a distributed configuration multipoint air sampling system.
Figure 3:
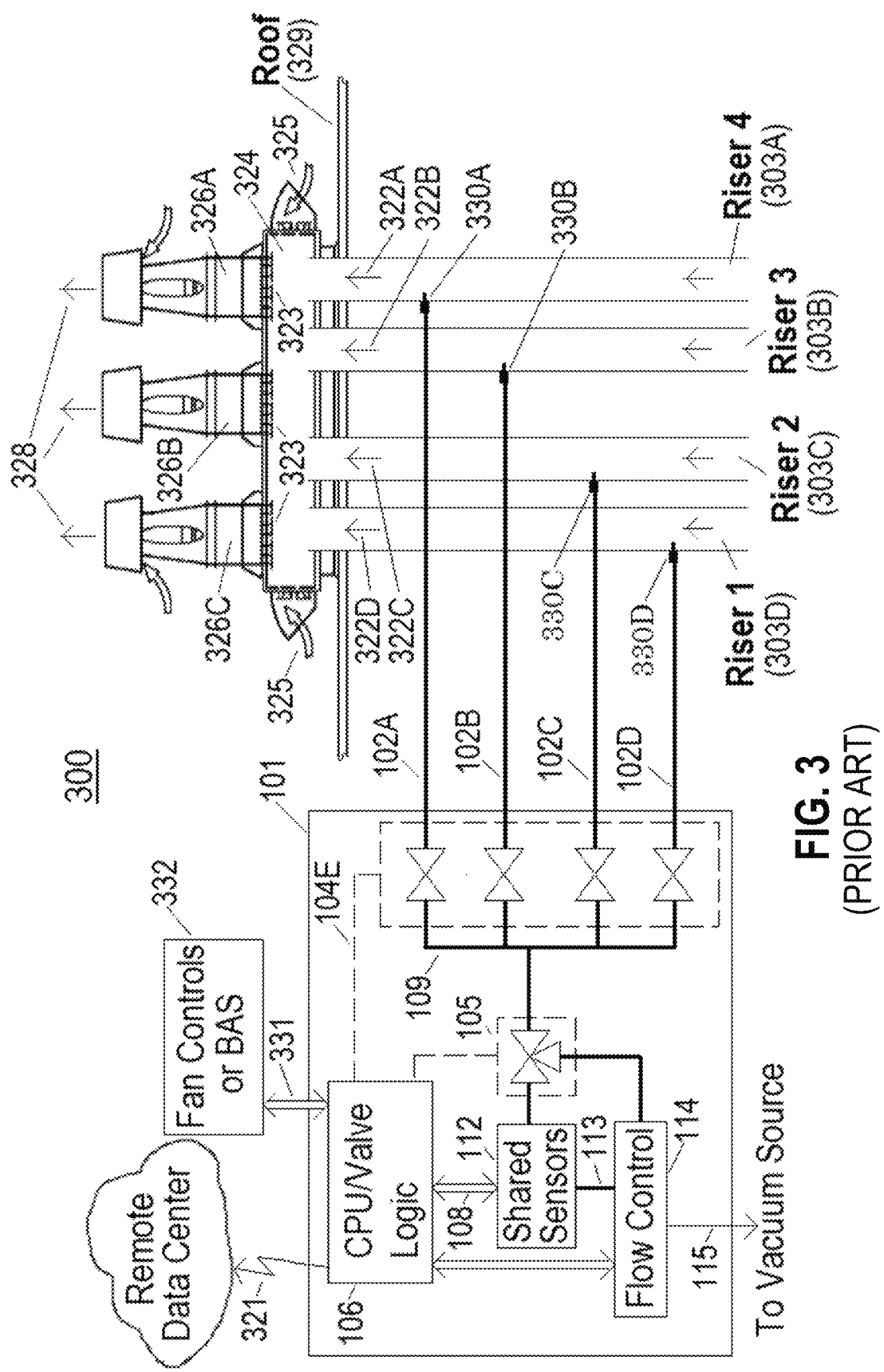
FIG. 3 illustrates an example of a prior art system of multipoint air sampling system used in exhaust demand control.
Figure 4:
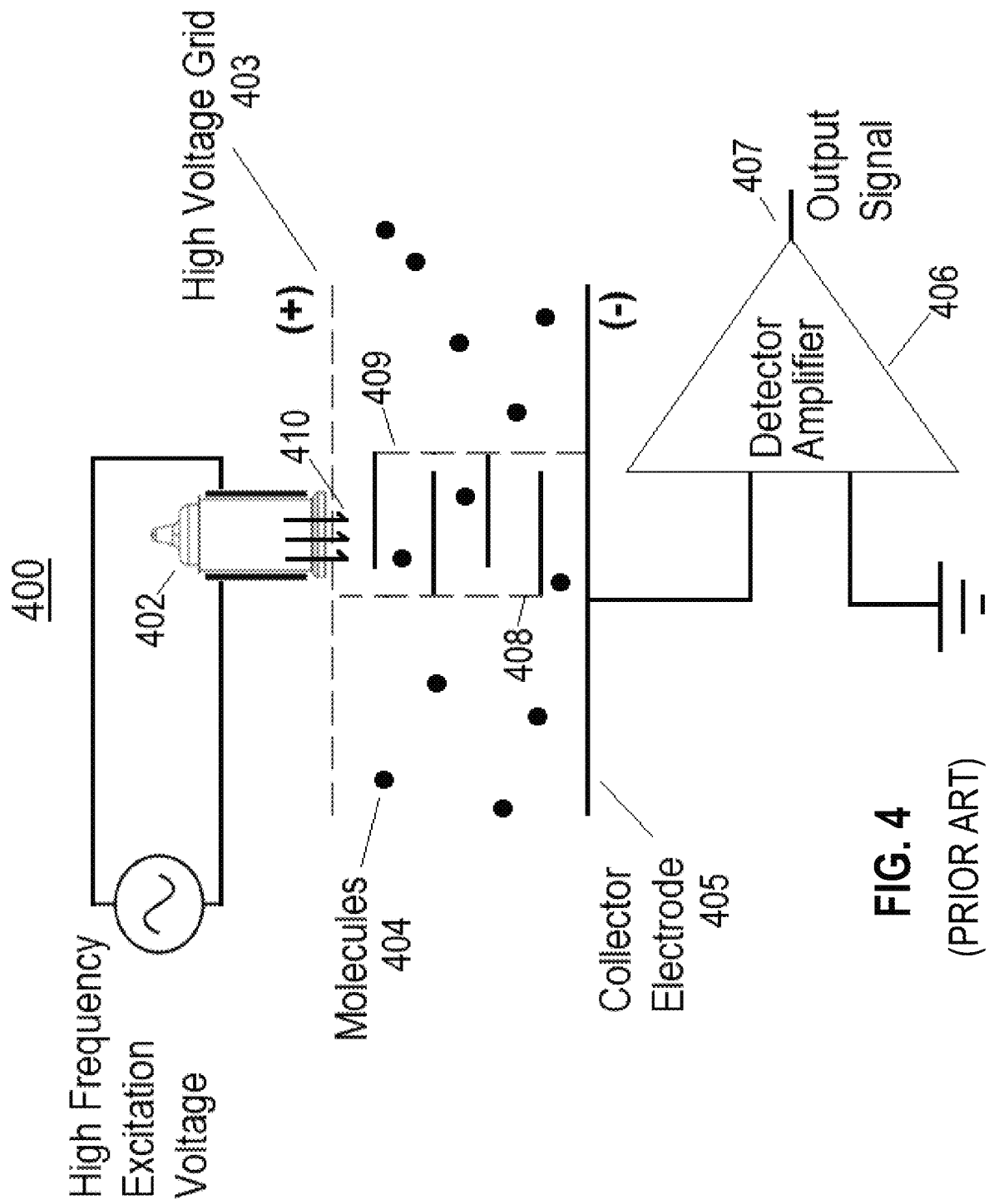
FIG. 4 illustrates an example of a prior art PID sensor.
Figure 5A:
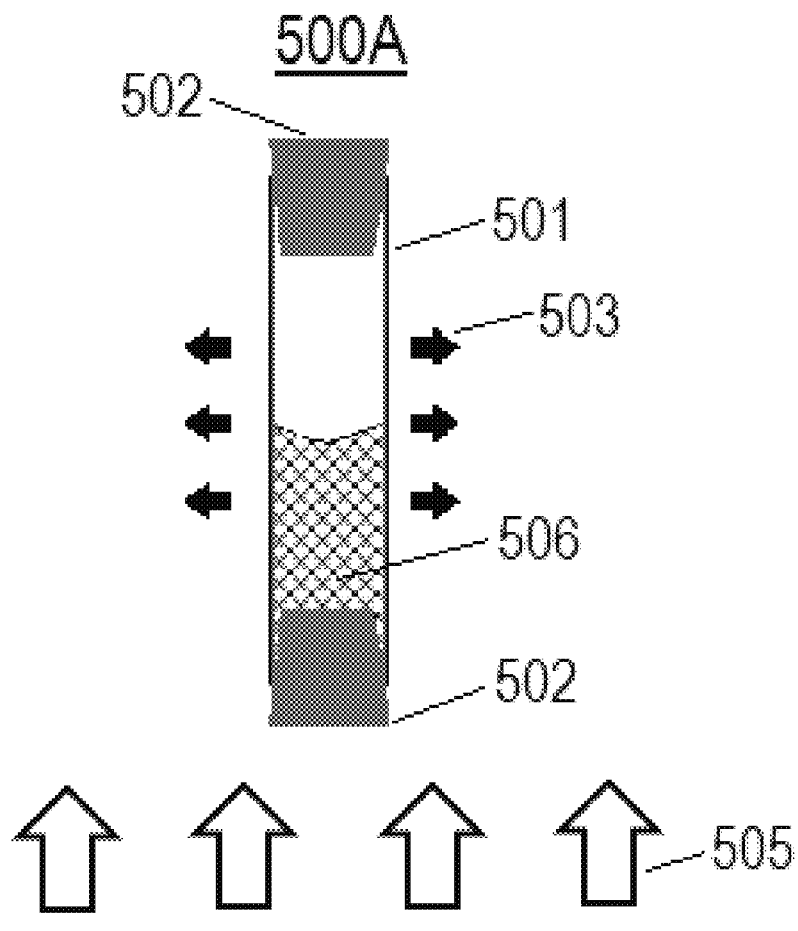
FIG. 5A illustrates an example of a prior art permeation tube.
Figure 5B:
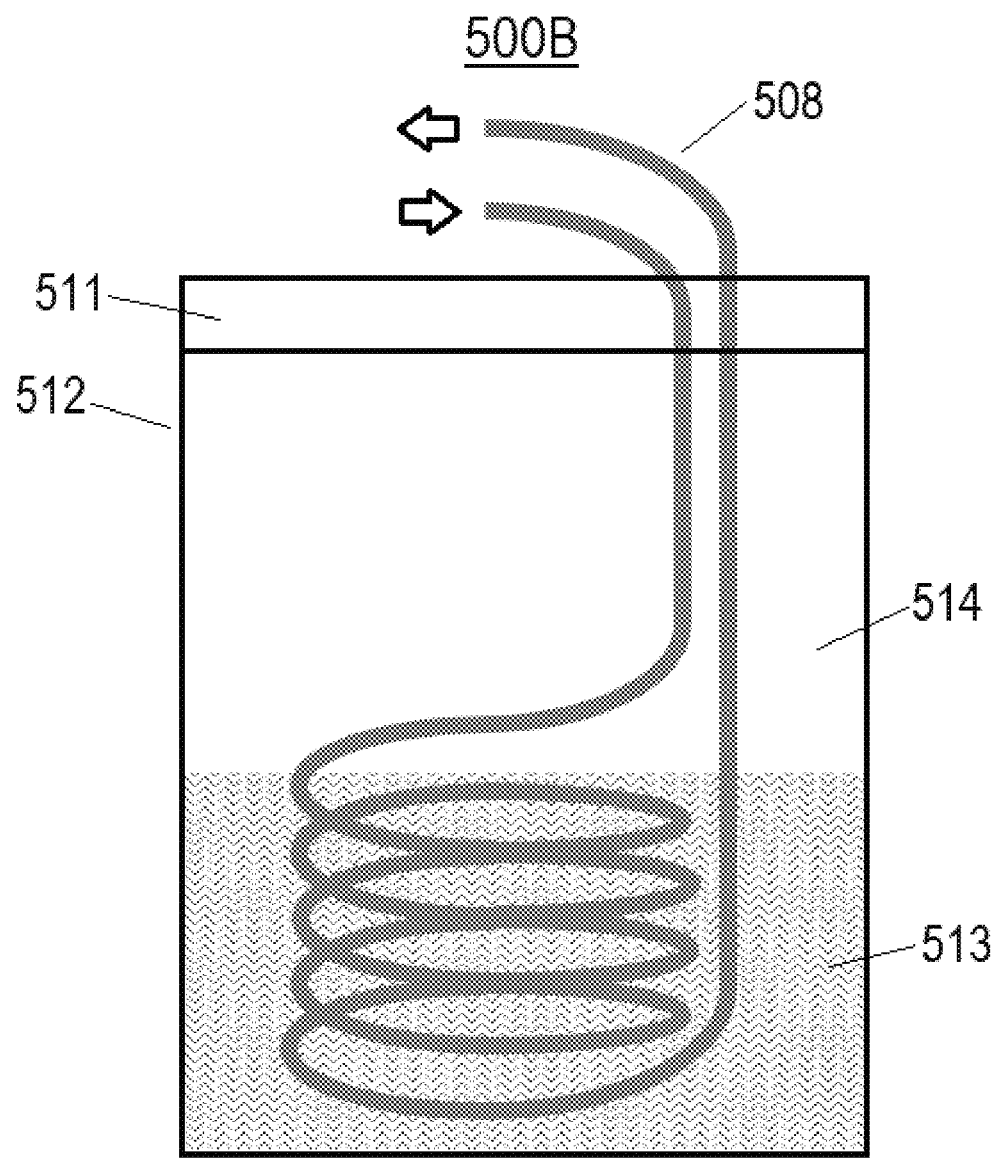
FIG. 5B illustrates an example of a prior art immersion tube source.

It is understood that the methods and systems described herein can apply to any multipoint air sampling system of a suitable configuration including star-configured systems (such as those described in FIG. 1) and distributed configurations (such as those described in FIG. 2) and configurations which include any combination of star or distributed configurations.

Figure 6A:
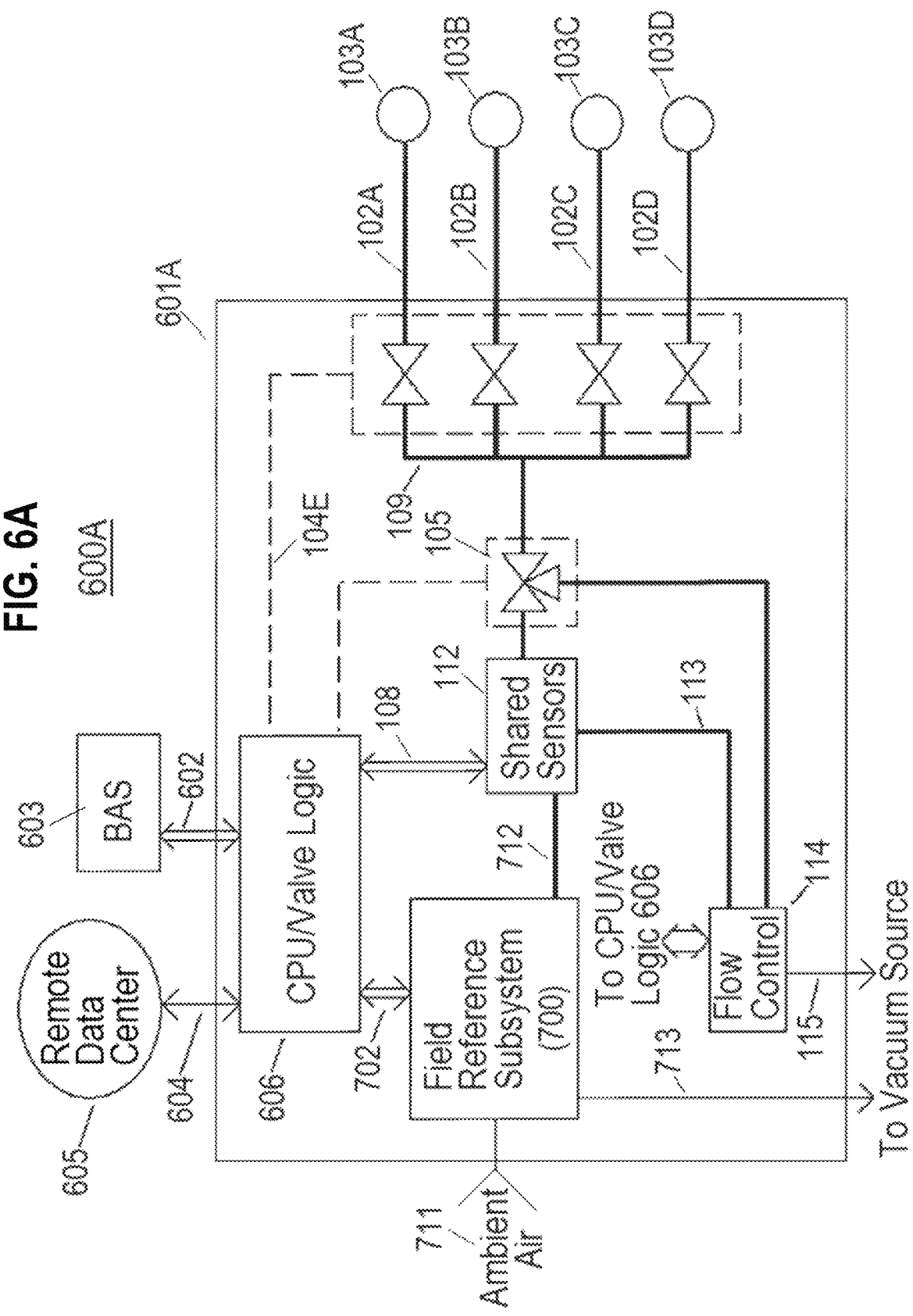
FIG. 6A illustrates an embodiment of a star-configured multipoint air sampling system which incorporates a field reference subsystem.
Figure 6B:
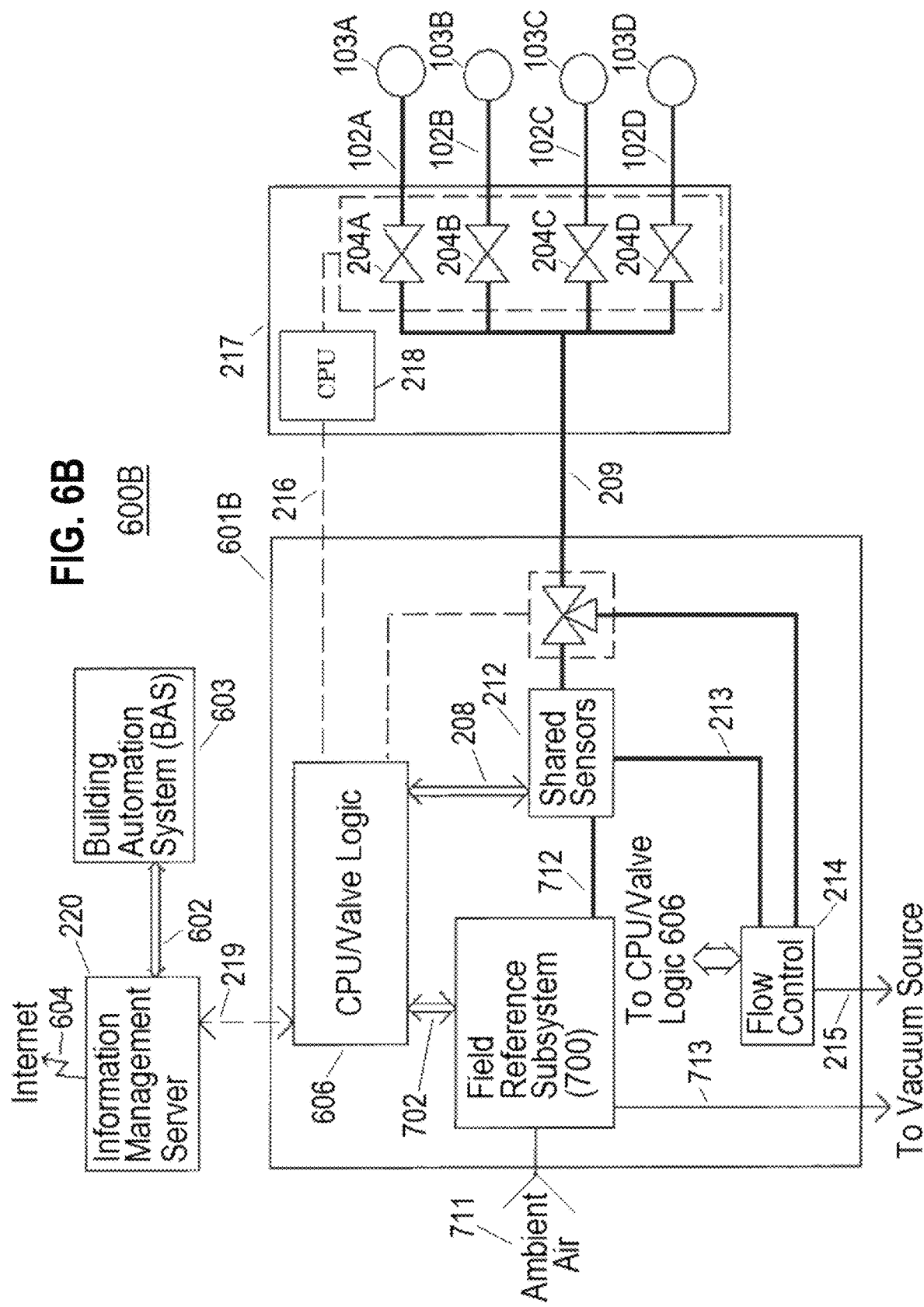
FIG. 6B illustrates an embodiment of a distributed configuration multipoint air sampling system which incorporates a field reference subsystem.

In some instances, the methods and systems described herein can include a modified, star-configured multipoint air sampling system or distributed configuration system with a field reference subsystem 700. FIG. 6A illustrates an embodiment of a star-configured multipoint air sampling system which incorporates a field reference subsystem. FIG. 6B illustrates modifications of a typical distributed configuration multipoint air sampling system with a field reference subsystem 700, as another embodiment of this invention. In both FIGS. 6A and 6B, the field reference subsystem 700 interfaces with CPU/Valve Logic 606, which can provide the same prior art air sampling sequencing functions as the CPU/Valve Logic modules described in FIGS. 1 and 2. However, logic 606 additionally can incorporate functionally to accommodate field reference subsystem 700 and other embodiments of the methods and systems described herein. CPU/Valve Logic 606 also interfaces with shared sensors similarly to how the CPU/Valve Logic modules of FIGS. 1 and 2 interact with the shared sensors disclosed in those figures. This is demonstrated in both FIGS. 6A and 6B to further emphasize that the teachings of this invention apply to any kind of multipoint air sampling system, including a star-configured system such as 600A, a distributed configuration system 600B, and configurations which include any combination of star and distributed configurations. For example, the enhancement 700 embodiment to the star-configuration system 600A can represent enhancements to a star-configured multipoint air sampling system including but not limited to a refrigerant monitoring system or a specific product, such as the SmartStack™ system that is manufactured by Measured Air Performance, LLC. The SmartStack™ system is a product which may be applied to implement exhaust demand control and can support other harsh environment air monitoring and active control applications. In some embodiments, the enhancements can be made to a distributed configuration system such as the Aircuity Inc. multipoint air sampling system.

FIG. 7 illustrates an embodiment of a field reference subsystem 700. At least a portion of the field reference subsystem of FIG. 7 can be portable or easily detached from a larger air sampling and control system to facilitate service as a part of a maintenance program which may coincide with the service and maintenance of shared sensors within the larger air sampling and control system. The field reference subsystem 700 can include a controlled permeation source 705 in order to generate a gas species or test gas to at least evaluate one or more shared sensors. One property of the controlled permeation source 705 is that it can generate a desired reference gas at a desired rate for extremely long durations. For example, the controlled permeation source 705 can continuously deliver a desired reference or test gas over a period of one to several years. A generated species of gas from the permeation source 705 flows from its output through tubing 714 and can be directed through valve 706, which may be selected to direct the output of the permeation source 705 to shared sensors through path 712, or it may direct the output of the permeation source 705 at a specific airflow rate that can be determined by flow control 707 to a vacuum source. The input side of the permeation source 705 may connect through optional elements such as the heat exchanger 709 and scrubber 710, or it may connect directly to ambient air 711. As one embodiment, valve 706 can be an electrical 3-way solenoid valve, which may include but is not limited to a low voltage latching valve or a poppet valve. In one embodiment, the valve 706 can be controlled via CPU 701. In a preferred embodiment, valve 706 can be controlled by CPU Valve Logic 606. In one embodiment, valve 706 may not be a part of the portable aspects of the field reference subsystem 700 but may be integrated as a fixed portion of the valve hardware within 600A, 600B, which act as the larger system.

One unique aspect of the permeation source 705 is that it can have attached to it one or more embedded features integrated within CPU 701. An embedded feature can be any number of CPU's, microcontrollers, microprocessors or memory devices. The memory devices can be nonvolatile memory that can be used to communicate or hold information about the permeation source 705.

In one embodiment of the methods and systems described herein, the controlled permeation source 705 can be electronically temperature controlled via the Heater and Control Electronics 717 and embedded features provided by the CPU 701, to maintain a predetermined operating temperature and therefore a predetermined permeation rate of a desired species from the controlled permeation source 705. One of the embedded features that may be provided by the CPU 701 relating to temperature control, as an embodiment, is that it can both enable and disable the Heater and Control Electronics 717. In some instances, CPU 701 can receive "enable" and "disable" commands through an interface such as the field cable connector assembly 702 to enable or disable the heater control function provided by electronics 717. One characteristic of most permeation sources is that they cannot actually be turned off but may continue to generate a gas at a certain mass flow rate that may vary with temperature. Therefore, as the heater controlled by electronics 717 is disabled, the permeation source may permeate at a lesser rate as it cools to ambient conditions. The actual ppm concentration of the gas that is delivered by the permeation source 705 is a function of a flow rate 718 through the controlled permeation source 705 and the permeation rate. In one embodiment of the methods and systems described herein, the carrier gas which flows at a rate 718 can be derived from ambient air. Another characteristic of permeation sources like the one described in FIG. 7, is that they can take many hours to stabilize or reach equilibrium, as either temperature or flow rate is changed in the device. Also, if the flow 718 were to be interrupted, the concentration of the species generated by the controlled permeation source 705 may grow to a very high value over time. This can be problematic if the flow 718 through the permeation source 705 drops to substantially zero for several hours when the species that is being generated by the permeation source 705 is an adsorptive gas. The reason for this is that the adsorptive gas can adhere to the walls of the tubing 715, 714 when the tubing 715, 714 is no longer flushed by flow 718. The adsorbed gas on the tubing 715, 714 may take several hours to desorb following the resumption of flow 718. This particular situation can result in a very high ppm output of the permeation source 705 for several hours after the flow 718 has resumed, which means that the output of the source 705 may not be as expected (i.e. not usable) for several hours after flow 718 has resumed. As controlled permeation source 705 is applied within subsystem 700 and the larger multipoint air sampling system such as 600A or 600B, it is critical that the source 705's ppm output be predictable. Therefore, as an embodiment, to ensure predictable operation of the output of the permeation source 705, a valve 706 in the subsystem 700 can be used to direct the output of the permeation source 705 through tubing 714 through flow control 707, and to a vacuum source 713 when the gas output of source 705 is not being directed to shared sensors 112, 212. In another embodiment, flow control 707 can be set to a gas 10) flow rate that is substantially the same as the gas flow rate at which the output of the permeation source 705 is delivered to the shared sensors 112, 212. This ensures that the flow rate 718 may be substantially the same as the valve 706 switches. As an exemplary embodiment of 707, what's known in the art of fluid controls as a sonic orifice can be used as flow control 707. A sonic orifice is a compact precision hole in a material through which a fluid flows which causes said fluid to reach the speed of sound. As said fluid reaches the speed of sound its flow rate self regulates based on the size of the aperture or hole.

An objective of the methods and systems described herein is to use a permeation source 705 to validate the accuracy of one or more shared sensors. It is especially desirable to be able to validate critical sensors, including but not limited to PID sensors. As has been discussed, when calibrated on isobutylene, a PID sensor's reading can be often referenced to units of ppm "as isobutylene". A suitable PID sensor can be responsive to gas concentrations in a range of several parts per billion to several ppm as isobutylene. Often these PID sensors may be calibrated with an isobutylene span gas that is on the order of several ppm. Also, another important objective is that the permeation source 705 be sufficiently compact so that it can easily be handled and shipped as a small light weight unit or be carried on a plane by a field technician who is traveling to the job site. As previously discussed, an immersion tube permeation source utilizing PTFE or FEP as the permeation material likely could be large in volume and length in order to generate several ppm of a suitable gas for validating a PID sensor. The limitations of such a source are in part due to the relatively low permeation rates of PTFE or FEP, the vapor pressure of the liquid used in the permeation source, and the practical temperature at which one would operate the permeation source in the field. For example, as has been discussed, permeation ovens often operate at 180 degrees Fahrenheit or higher, yet, such high operating temperatures could pose serious burn risks to field technicians without appropriate packaging considerations. Also, when operating any electrical components at high temperatures (heater elements for example), the electrical components are subject to a higher failure rate or lower MTTF. As an embodiment of the methods and systems described herein, the permeation source 705 can be operated at a temperature which is slightly above a maximum practical ambient temperature where the source 705 may be installed. If for example the heater 717 were set to a temperature that is lower than ambient conditions, then the operating temperature of source 705 can be the ambient temperature and not the specified temperature. This change in operating temperature can cause a degradation in the permeation rate accuracy of the source 705. Many multipoint air sampling systems can be installed within interstitial spaces, mechanical spaces or penthouses. These spaces house many types of electrical and controls equipment; therefore, it would be unusual for such spaces to exceed 90 degrees Fahrenheit. With some buffer, an exemplary operating temperature for a permeation source 705 can be 100 degrees Fahrenheit. However, any possible temperature can be an operating temperature for the source 705. In one embodiment, to achieve a high ppm output low temperature permeation source 705, the permeation source 705 is an immersion tube permeation source which utilizes high density polyethylene (HDPE) as its permeation tubing. HDPE has a permeability that is several orders of magnitude higher than that of PTFE or FEP. Using HDPE, one can design a permeation source 705 that uses less tubing and therefore is compact. HDPE may not be suitable for use with many of the species of compounds found in the permeation source industry because HDPE may not be robust enough to withstand the highly corrosive compounds sometimes used within a permeation source. In some instances, the methods and systems herein may use compounds for a permeation source that are compatible with HDPE and are relatively safe to transport and handle.

Figure 8:
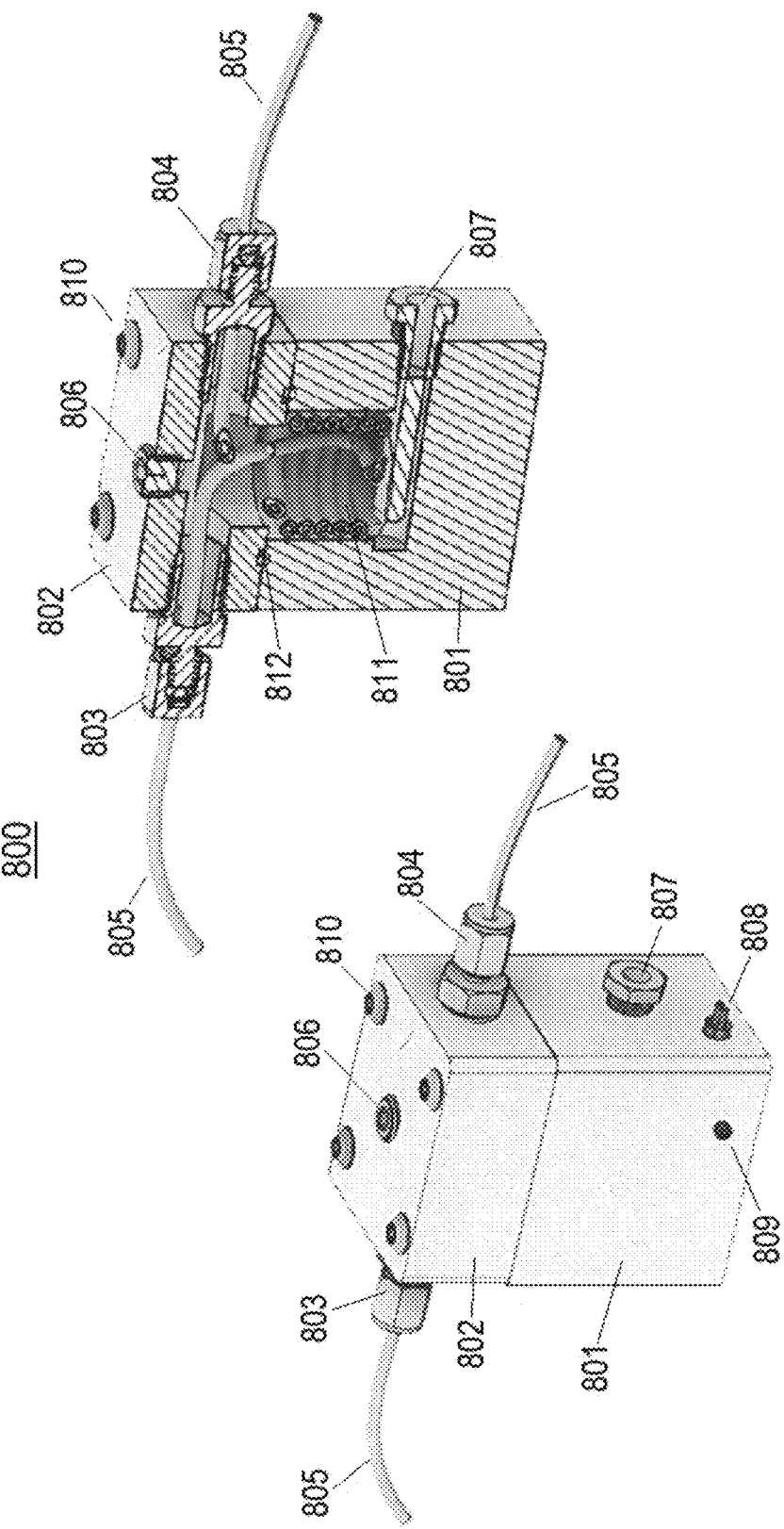
FIG. 8 illustrates an example of a permeation source in accordance with the teachings of this invention.

FIG. 8 illustrates a detailed view of an exemplary permeation source portion of a controlled permeation source 705, according to the teachings of the methods and systems described herein. FIG. 8 shows both a cross-sectional view and a solid view to help illustrate aspects of the construction of the exemplary permeation source. Exemplary permeation source 800 can in some instances be a subset of the controlled permeation source 705. FIG. 8 does not illustrate the thermal insulation material which is placed around the source 800 in order to make it easier to increase the temperature of the source 800 up to a desired temperature setpoint (such as 100 degrees Fahrenheit for example) quickly and maintain said temperature setpoint. Such insulative material may include any practical materials including but not limited to a variety of synthetic and non-synthetic materials. In one embodiment, permeation source 800 is placed in a container that is slightly larger than 800 in volume and the gap between 800 and the container is filled with polystyrene expansion foam. In another embodiment, the insulation which surrounds permeation source 800 is Aerofoam insulation. In yet another embodiment, the insulative material which surrounds 800 is foil-backed melamine. In still another embodiment, the insulative material which surrounds 800 is flexible polyurethane foam. In still another embodiment, the insulative material which surrounds 800 is flexible closed-cell polyethylene foam which can be ½-inch thick.

The side of the permeation source base 801 in which set screw 809 can be inserted can measure 2.25 inches wide by 3 inches tall, including the height of the shroud 802. The depth of the base and shroud can measure approximately 1.9 inches. In comparison to other permeation sources, the source 800 depicted in FIG. 8 is compact and portable. For example, prior art gas cylinders holding 17 liters of a calibration gas can measure approximately 3 inches wide and 11 inches tall, without the necessary gas regulator. Such a 17-liter cylinder would be capable of testing a sensor approximately eight times whereas, the permeation sources described herein can test a sensor any number of times during the normal field life of a sensor.

The permeation source 800 can be an immersion tube style permeation source, having a base 801 that is designed with an inner chamber 811, which is able to substantially, simultaneously house the desired permeation liquid and a predetermined length of permeation tubing 805. The tubing 805 can be manufactured out of HDPE. Said base 801 and surface of the chamber 811 may be made of the same or different materials. For example, in one embodiment the chamber portion of 811 may have a coating such as: a vapor deposition of anhydrous aluminum oxide, an anodized aluminum surface, a vapor deposition of gold, a vapor deposition of stainless steel, a coating of FEP or PTFE, or any suitable material that is compatible with the permeation liquid of choice. In some embodiments, the permeation liquid used in the source 800 is compatible with aluminum.

In such an embodiment, the base 801 and the surface of the chamber 811 can both be manufactured out of aluminum. The tubing 805 can measure ⅛-inch in outer diameter, and 1/16-inch in inner diameter. Any length of tubing may be used in the source 800, however in some preferred embodiments, the tubing may have a length between one and five feet long, where the length is chosen based on a vapor pressure of the permeation liquid housed within the chamber 811.

In some instances, tubing 805 can be wound in a helical stacked fashion within the chamber 811, as shown in FIG. 8. In other embodiments, the chamber 811 may be large enough to simultaneously support the helical stack of tubing 805 while also being large enough in volume to support 10 to 50 milliliters of a desired permeation liquid.

In one embodiment, the lower portion of base 801 can have a cylindrical hole bored into it on one side to support a temperature sensor 807 that can be in communication with the permeation liquid housed within the chamber 811. The temperature sensor 807 can be a thermistor sensor disposed within a thermowell that screws into the base 801 and can provide a liquid tight seal to prevent the permeation liquid from escaping the chamber 811. The thermistor 807 can be electrically connected through wires to the heater and control electronics 717 such that said electronics 717 can use a temperature measurement from the temperature sensor 807 as feedback in a control loop used to control the temperature of the permeation liquid within the chamber 811. A heater element 808 can be used as a heat source by the heater and control electronics 717 as a part of the control of the temperature of the permeation liquid within the chamber 811. In some embodiments, the heater element 808 can be a cartridge heater. A cylindrical hole can be bored into the base 801, and a cartridge heater 808 can be inserted in the base 801 and captivated by a setscrew 809. The heater 808 may be electrically connected to electronics 717 via wires. The heater can be, in some instances, a nickel-chromium alloy wire, Kapton flex heaters, power resisters, polyimide heaters, silicone rubber heaters, lamps, or any other compatible heating sources.

Tubing 805 can be inserted through fitting 803 and a length of tubing 805 can be preferably coiled within the chamber 811. The length of the tubing 805 travels through the coil within 811 and exits through fitting 804 in such a way that tubing 805 can be substantially one piece of tubing as it passes through the fittings 803, 804 and the chamber 811. In one embodiment, fittings 803 and 804 can be barbed-style fittings. In one embodiment, fittings 803 and 804 can be compression style fittings which provide the function of a tight seal which prevents the liquid contents within the chamber 811 from escaping, while also enabling the tubing to penetrate through a fitting 803 and into the chamber 811 and out of the chamber 811 through the fitting 804. In some embodiments, there are many suitable types of compression fittings known to those experienced in the art of tubing or pipe fittings. For example, a suitable compression fitting includes one that incorporates one or more ferrules that the fitting compresses against tubing 805, such as but not limited to Yor-Lok style fittings, flared fittings, or other suitable compression style fittings.

Fittings 803 and 804 can be seated into shroud 802, and the fitting 803 acts as a tightly sealing cover for the assembly 800. For some embodiments of the permeation source 800, the shroud 802 is tightly sealed to bottom 801 using an O-ring 812 and fasteners 810. The shroud 802 may be made of any practical material if said material is compatible with the permeation liquid to be held by chamber 811. This need for compatibility of 802 with the permeation liquid is because the permeation liquid in 811 and its vapors are in constant communication with the inner surface of shroud 802. As a preferred embodiment, shroud 802 is made from HDPE, both because it's inexpensive and because HDPE has favorable insulative properties which help to prevent heat from escaping the inner chamber 811.

The permeation source 800 features a convenient fill plug 806 which screws into a cylindrical hole at the top of shroud 802. The purpose for fill plug 806 is that it enables the permeation source chamber 811 to be filled with permeation fluid without a need for removing shroud 802, and this saves time when servicing 800, but it also makes the process of filling less messy and less subject to liquid spills. Further, plug 806 provides a convenient way of checking the permeation liquid level to see if the unit 800 must be serviced.

In one embodiment, provided is a permeation source that poses little handling or exposure risk to the field technicians who, with ordinary training, can support its field implementation. Also, the permeation source may be periodically removed from the field and shipped to a factory for service. In some instances, the methods and systems described herein permit the permeation source to be shipped via air freight, with substantially no Department of Transportation (DOT) restrictions. Also, while at the factory undergoing service, the permeation source can pose little exposure or handling risk to the factory trained technicians who provide said service.

In one embodiment, the permeation source 800 and subsystem 700 is used to at least test a PID sensor having a 10.6 eV lamp that is part of shared sensors. In this embodiment, permeation source 800 can be used to generate a VOC species. In one embodiment, the VOC species that is generated by the permeation source 800 can be ethanol and therefore the permeation liquid that is installed in chamber 811 is pure ethanol. With a 10.6 eV lamp, the PID's response factor to ethanol can be approximately 10. Therefore, to produce a concentration of ethanol that would be read by the PID as 1 ppm as isobutylene, the permeation source must generate 10 ppm of ethanol. In another embodiment, the VOC species that is generated by permeation source 800 can be acetone and therefore the permeation liquid that is installed in chamber 811 is pure acetone. With a 10.6 eV lamp, the PID's response factor to acetone can be approximately 1.2. Therefore, to produce a concentration of acetone that could be read by the PID as 1 ppm as isobutylene, the permeation source must generate 1.2 ppm of acetone. As a preferred embodiment, the VOC species that is generated by permeation source 800 is isopropanol and therefore the permeation liquid that is installed in chamber 811 is pure isopropanol. With a 10.6 eV lamp, the PID's response factor to isopropanol is approximately 5.6. Therefore, to produce a concentration of isopropanol that is read by the PID as 1 ppm as isobutylene, the permeation source must generate 5.6 ppm of isopropanol. There are a wide range of other VOC species which may be used in source 800. There is also an advantage to utilizing compounds which are readily recognized by the layperson, such as the aforementioned compounds, because it is less likely that such compounds would be perceived by a layperson as being dangerous which aids in the acceptance and approval of its implementation. Isopropanol has a slight advantage over other VOC species in that it is less adsorptive than ethanol and acetone and a PID's response to isopropanol is better than that of ethanol and acetone.

In another embodiment, the permeation source 800 and subsystem 700 is used to at least test a PID sensor having a 10.6 eV lamp using a non-VOC species. In one embodiment the non-VOC species is ammonia. Ammonia, when in gas form is one of the most toxic compounds however, when it is in solution with water (what's known in the art as ammonium hydroxide) it is quite safe and manageable as it can be easily diluted due to its miscibility properties with water. Ammonia is also compatible with HDPE. With a 10.6 eV lamp, the PID's response factor to ammonia is approximately 9.4. Therefore, to produce a concentration of ammonia that is read by the PID as 1 ppm as isobutylene, the permeation source must generate 9.4 ppm of ammonia. Ammonium hydroxide is a common household cleaner. When ammonium hydroxide is used as the permeation liquid in permeation source 800, trace quantities of ammonia may permeate through tubing 805, to provide a reliable test source for the PID sensor.

One of the issues with a permeation source, such as an immersion tube permeation source, is that if the carrier gas (such as the air flowing through tube 805) is at a very different temperature than the permeation liquid, even though the permeation liquid can be held at a constant average temperature, the actual permeation rate of the species in chamber 811 may be altered. The reason for this is that a temperature gradient becomes established at the interface between the surface of the tubing 805 and the permeation liquid. This may cause the permeation rate to be altered by a significant amount, for example 50-100% or more, depending on the temperature difference. In the prior art, this has not been an issue with, for example a permeation source held within a permeation oven because the oven is so large that it may automatically preheat the air or carrier gas before it enters the permeation source. As has been described, the permeation source can operate at a temperature of about 100 degrees Fahrenheit, which is close to the maximum ambient temperature conditions for the mechanical space or penthouse in which the multipoint air sampling system is applied. However, during the colder seasons (depending on geographic locations) ambient temperatures in mechanical spaces can reach 45 degrees Fahrenheit or lower. Therefore, as such cool air enters and travels through tubing 805, it may impart a potentially serious cooling effect on the permeation liquid. Based on temperature alone, the environment that a multipoint air sampling system is installed in is very different than the controlled environment of a laboratory or metrology lab because the air temperature of said laboratories or metrology labs is intentionally well regulated.

Figure 9:
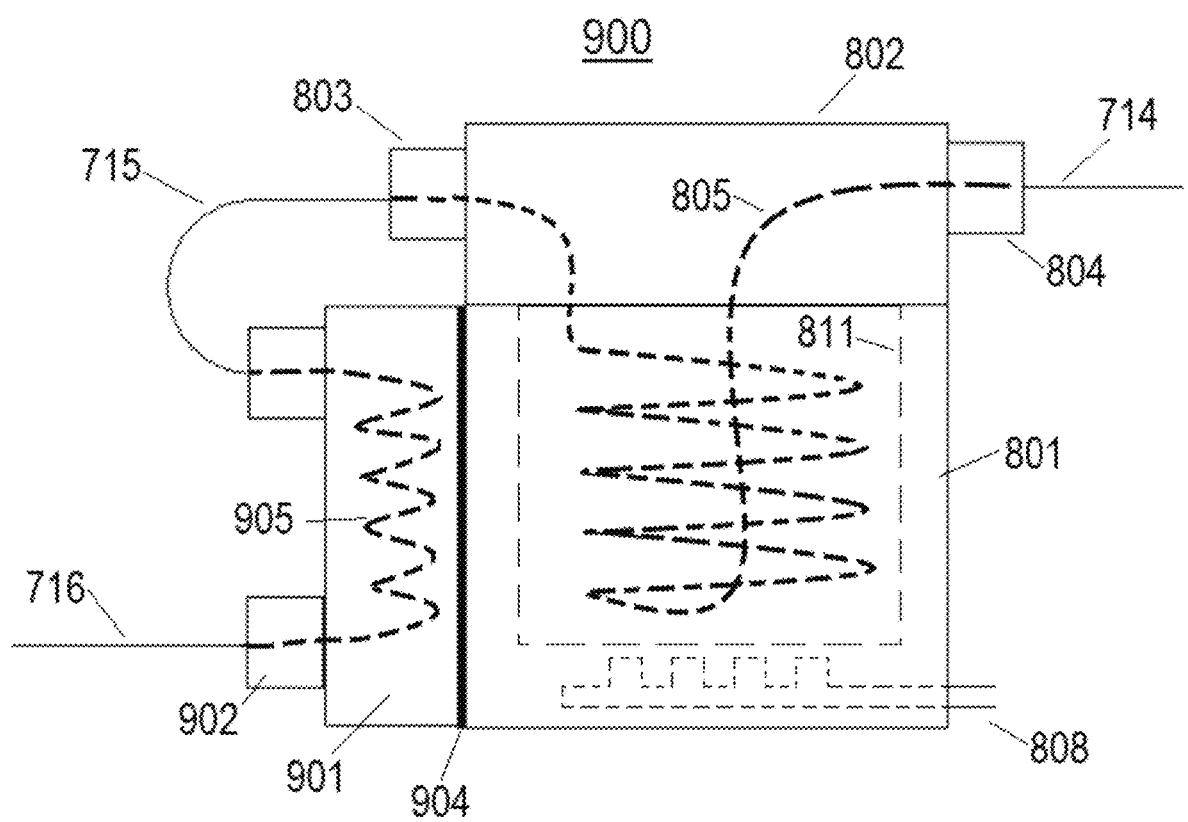
FIG. 9 illustrates an example of a passive heat exchanger in accordance with the teachings of this invention.

In some instances, a heat exchanger 709 can be used to preheat the ambient air 711 which travels through tubing 805 to minimize variations in the permeation rate of 705 due to temperature variations in ambient air 711. In this embodiment, the preheat action of the heat exchanger 709 ensures that only minimal heat exchange occur between the air in tubing 805 and the permeation liquid, which means that air source 711 may not influence the permeation liquid temperature. In one approach, the heat exchanger 709 heats ambient air 711 to within two degrees Fahrenheit of the permeation liquid temperature as measured by temperature sensor 807. In another embodiment, heat exchanger 709 is a passive heat exchanger. In a further embodiment, said passive heat exchanger is in thermal communication with the controlled permeation source 705. In this embodiment, which is further illustrated in FIG. 9, the heat exchanger 901 can be made of a thermally conductive material that can absorb and store heat energy. As embodiments, heat exchanger 901 can be made from any thermally conductive material. In one embodiment the heat exchanger 901 can be made from aluminum, while in another embodiment, the heat exchanger 901 can be made from brass. In some instances, heat exchanger 901 can be in thermal communication with base 801 via a thermal interface 904 that may include any number of methods of ensuring good thermal conductivity. In other instances, the thermal interface 904 can simply be the surface of the heat exchanger 901 in contact with the surface of base 801, while in still other instances, the thermal interface 904 comprises thermal grease.

The heat exchanger 901 can include a circuitous path 905 through which the ambient air 711 flows. The circuitous path 905 may be of the same material that the heat exchanger 901 is made from or it may be a tubing material that is wrapped within the heat exchanger 901 and that is in thermal communication with the heat exchanger 901. In one embodiment, circuitous path 905 is milled out of the material of the heat exchanger 901. The ambient air 711 flows into the circuitous path 905 from tubing 716, which is connected to fitting 902. As the air from 711 flows through circuitous path 905, it is warmed to approximately the temperature at which the permeation source 705, 800 is controlled to, since heat exchanger 901 is in thermal communication with base 801 in a highly thermally conductive manner. Therefore, as the temperature of base 801 is increased by heater 808, so may the temperature of 901, until the two temperatures of the heat exchanger 901 and the base 801 are substantially the same. Likewise, as the ambient air 711 flows into circuitous path 905, the lower temperature of the ambient air 711 in relation to the heat exchanger material 901 may cause heat to flow across the interface 904. However, any gradual lowering of temperature within the chamber of 811 may be sensed by temperature sensor 807 which, through electronics 717 may be compensated for through heater 808.

Figure 11:
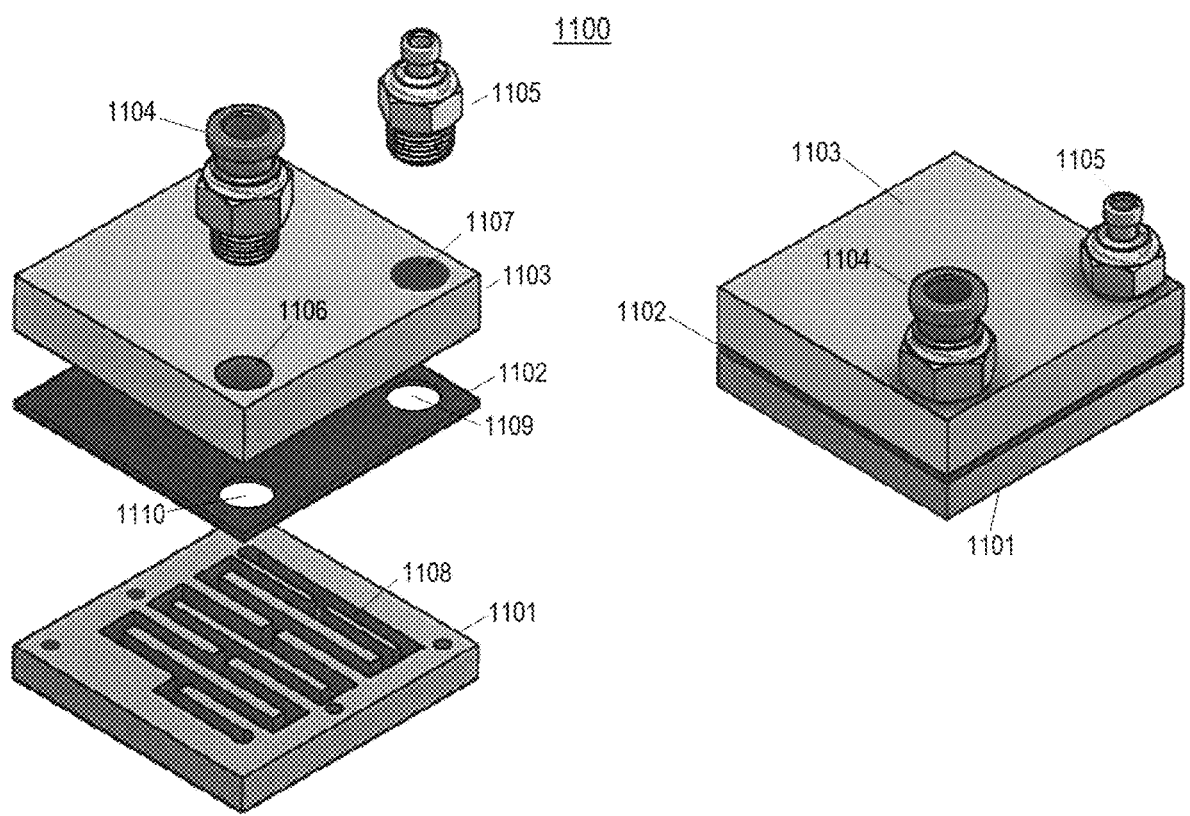
FIG. 11 illustrates an example of a heat exchanger with multiple layers, according to the teachings of this invention.

An exemplary embodiment of passive heat exchanger 901 is illustrated in FIG. 11 as heat exchanger 1100. As shown in FIG. 11, the heat exchanger 1100 can comprise three layers; a first material 1101 with a circuitous airflow path 1108 routed or milled into it, a second gasket material 1102 which seals 1101, and a third shroud material 1103 which serves as a medium to connect fittings 1104 and 1105, and 1103 serves as the structural top of 1100. FIG. 11 shows both an exploded view and an assembled view of heat exchanger 1100. In embodiments of 1100, shroud 1103 may be made of any material including but not limited to plastics or metal. In an exemplary embodiment, shroud 1103 is made from HDPE, given that the material is inexpensive, has good insulative properties, and is easy to machine. Shroud 1103 can be secured to base 1101 using any practical method however, as a preferred embodiment, shroud 1103 is secured to base 1101 using machine screws which are threaded into base 1101. The airflow inlet to 1100 is through fitting 1104 which screws into threaded hole 1106. Fitting 1104, for example would interface to tubing 716, which tubing 716 can be any size tubing. As a preferred embodiment, tubing 716 is a flexible polymer tubing. In an exemplary embodiment, tubing 716 is flexible polyvinyl chloride (PVC) having an outer diameter of ¼ inch and an inner diameter of ⅛ inch. Such an exemplary embodiment of tubing 716, requires that fitting 1104 support ¼ tubing as an exemplary embodiment. As an embodiment, fitting 1104 is a luer lock fitting. As an exemplary embodiment, fitting 1104 is what's known in the art of pipe and tubing fitting technology as a push-to-connect fitting. Push-to-connect fittings are very popular and provide a simple method of connecting or disconnecting tubing.

Referring again to FIG. 11, gasket 1102 provides a gas tight seal between the underside of shroud 1103 and the side of base 1101 on which circuitous path 1108 exists. Holes 1110 and 1109 permit the flow of air into fitting 1104 through path 1108 and out through fitting 1105, respectively.

Air flowing through tubing 716 into fitting 1104, down through hole 1106 into one end of circuitous path 1108, exiting the opposite end of 1108 and then exits through hole 1107 and then through fitting 1105 through tubing 715 which connects to the input of the permeation source. As an exemplary embodiment tubing 715 is ⅛-inch outer diameter HDPE tubing. Therefore, as an exemplary embodiment, fitting 1105 can support ⅛-inch outer diameter tubing. As an embodiment, fitting 1105 can be a luer lock fitting. As an exemplary embodiment, fitting 1105 can be a push-to-connect fitting.

As an exemplary embodiment of a passive heat exchanger, base 1101 can be made from brass and provides a circuitous path 1108 milled into it. Until recent years, such a circuitous path would have been extremely expensive to manufacture because of the labor involved with such a process. However, it is now possible to accomplish such an intricate machining operation using a low-cost CNC router, for example, or other subtractive manufacturing process. This makes it highly cost effective to incorporate such a feature as a circuitous path 1108. As air 711 flows into path 1108 from fitting 1104 and tubing 716, it is rapidly warmed to the temperature of the thermally conductive surface of 1101, which is in thermal communication with the conductive surface of base 801, therefore warming air 711 to the approximate temperature of base 801 and therefore the approximate temperature of the permeation liquid held within chamber 811.

In one embodiment, heat exchanger 901 can be incorporated within base 801. In this embodiment, the fabrication of base 801 also incorporates the fabrication of circuitous path 905 into the side of 801. This eliminates interface 904, which improves thermal conductivity between 901 and 801. As an example, in one embodiment, the permeation source base 801 is made from aluminum into the side of which circuitous path 905 is incorporated. As a preferred embodiment of where circuitous path 905 is made from aluminum said aluminum is anodized. The anodization of aluminum is important because it enables the purity of air flow through 716 to be maintained. Non-anodized aluminum, over time may oxidize which can add contaminants to the output 714 that are not desirable, as such contaminants can foul sensors.

Figure 10:
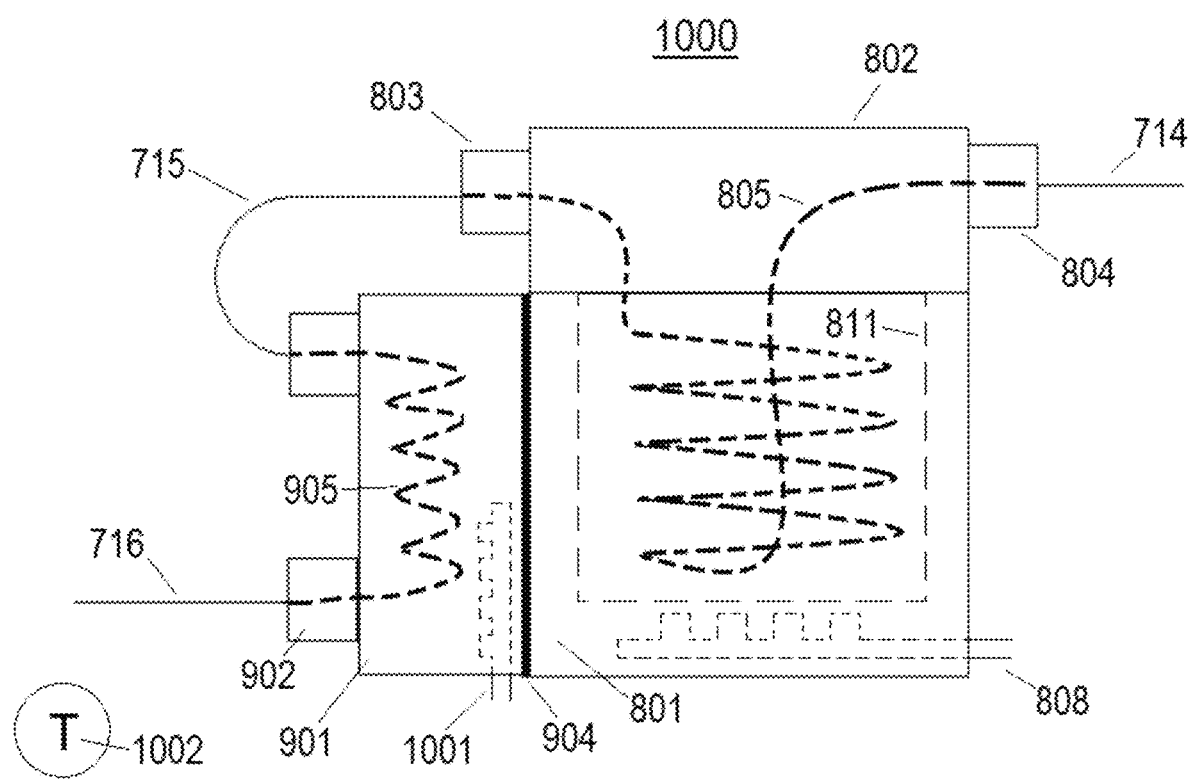
FIG. 10 illustrates an example of a heat exchanger that uses a controlled method of preheating the ambient air, according to the teachings of this invention.

In another embodiment, illustrated by FIG. 10, the heat exchanger 709 can incorporate a controlled method of preheating the ambient air 711 to a desired temperature. This active heat exchanger method incorporates heater element 1101, which supplements the heat transferred between base 801 across interface 904 to the heat exchanger 901. The purpose for an active heat exchanger approach 1000 is to address applications where the ambient air 711 is at a substantially different temperature than the desired temperature setpoint of the electronics 717 in which passive heat exchanger 901 cannot provide an adequate amount of heat transfer to sufficiently preheat the air flowing through tubing 805 to ensure that the permeation rate of 705 may not be affected. Those familiar with power electronics may recognize that there are a wide range of devices which are commercially available for use as a suitable heater 1001, including but not limited to: nickel-chromium alloy wire, Kapton flex heaters, power resisters, polyimide heaters, silicone rubber heaters, lamps, and a wide variety of other heating sources. In one embodiment, heater 1001 can be a cartridge heater that is captivated within a cylindrical hole within the thermally conductive portion of the heat exchanger 901. For example, said cartridge heater could be inserted within the base 1101 which contains the circuitous path 1108. Heater element 1001 may be controlled by electronics 717 which, as an embodiment, would include a second control circuit within electronics 717 for the purpose of applying and controlling power to heater 1001.

FIG. 10 also illustrates the use of an optional element of a temperature sensor 1002. The heater control function of heater 1001, in some instances, can be enabled when the temperature as measured by temperature sensor 1002 of ambient air 711 has dropped below a predetermined value. This embodiment addresses a control loop instability or resolution issue that may arise as the two different control functions to separately control heating element 1001 and heating element 808, may interfere with each other in conditions where very little heat may be transferred across interface 904 to adequately preheat ambient air 711. This instability for example may occur during warmer seasons where the temperature of ambient air 711 is close to that of the temperature setpoint applied to electronics 711. The temperature sensor 1002 may include any practical temperature sensor technology, and in some instances, can be a thermistor. In one embodiment, temperature sensor 1002 can be monitored by CPU 701 to activate the control loop which uses heater element 1001 to actively preheat the ambient air 711 when say monitored ambient temperature is below a predetermined value. In one embodiment, the predetermined value at which the active heat exchanger method is activated can be any value of ambient air 711 below 45 degrees Fahrenheit.

As has been described, it is beneficial that aspects of the field reference subsystem 700 be portable to facilitate the service of these components. In one embodiment, controlled permeation source 705 and heater and control electronics 717 along with CPU 701 are packaged together in such a way that they can easily be shipped together back to a factory for service. For example, such a service would include the replacement of the permeation liquid held within the source 705 and a routine evaluation of the heater electronics to verify that these critical components continue to function properly. In another embodiment permeation source 705 additionally includes a heat exchanger 709 and said heat exchanger can be packaged with permeation source 705 along with electronics 717 and CPU 701.

In some embodiments, the CPU 701 can include an interface 702 to the multipoint air sampling system's CPU, along with one or more embedded features. In these embodiments, said interface 702 is a modular cable that supports an electrical connection between the multipoint air sampling system's CPU and CPU 701. This electrical connection supports digital communications and power to the CPU 701 and electronics 717. The communications between multipoint air sampling system's CPU and CPU 701 may be any form of digital or analog communications between multipoint air sampling system's CPU and CPU 701 that includes but is not limited to an SPI bus, $I^2C$ communications, RS232 communications, RS485 communications, or even a simple binary interface such as one or more binary inputs and outputs used to provide enabling and communications functions between the two CPU's. In an embodiment, as an embedded feature of CPU 701, the status of the permeation source 705 and electronics 717 are conveyed through interface 702. For example, an error condition may be signified to the multipoint air sampling system's CPU from CPU 701 if there are problems with the temperature control of 705. In another embodiment of an embedded feature of CPU 701, interface 702 is used to enable or disable the permeation source heater 808 or the active heat exchanger heater 1001. Such an embodiment that allows multipoint air sampling system's CPU to enable or disable the one or more heaters of the permeation source 705 would be valuable for example in applications where a test gas from the permeation source 705 is only needed on an infrequent basis, and in this case, it would not be necessary to nor energy efficient to continuously operate the heater 808, 1001. Another important embodiment of interface 702 is that it can enable permeation source 705 configuration information to be communicated to multipoint air sampling system's CPU. Such configuration includes but is not limited to: the species of test gas, the permeation rate or ppm output, the calibration flow rate, when it was configured, and temperature settings.

In applications such as those described herein, it is important that the purity of the test gas that is generated by the controlled permeation source 705 can be maintained in such a way that as the test gas is applied to sensors within the multipoint air sampling system, other interfering gases are not present, because these other interfering gases would augment the response of the sensors. In many cases for example, compounds may be present within ambient air 711 which would add to the sensor's response because these compounds in ambient air 711 comingle with the test gas generated by the source 705. To maintain the purity of the test gas generated by source 705, a scrubber 710 can be incorporated within subsystem 700. In one embodiment, the scrubber 710 can incorporate activated carbon, which can remove most interfering compounds which may be present in ambient air 711. Depending on the level of contaminants within the ambient air 711, such a scrubber 710 may not function to remove all contaminants indefinitely as the activated carbon may eventually become depleted. Therefore, as one embodiment, the scrubber 710 shall be replaceable. The replacement of such a scrubber 710 may, for example coincide with the regular maintenance schedule of sensors when a field technician is expected to be present to provide such maintenance.

As prior art, a permeation source can be calibrated by operating the permeation source at a constant elevated temperature for several days or weeks and then measuring the mass difference of the permeation fluid between the start and the end of the calibration process. The mass difference between the start and the end of this calibration process divided by the duration of the process determines the permeation rate of the permeation source at the specified temperature. This is a very painstaking and expensive process which provides what is known as an absolute calibration or primary standard because the output of the permeation source (its mass permeation rate) is related to only a physical property; in this case the temperature of the permeating liquid.

In one embodiment, the multipoint air sampling system can incorporate a field reference subsystem having a permeation source 705 that may be calibrated as a primary standard. In one embodiment, the calibration value 1306 derived from the method described in the description of FIG. 13, can be stored in CPU 701. As a primary standard, the permeation source 705 provides an absolute level of accuracy with the least amount of uncertainty. Such a primary standard may not be subject to the tolerance stacking that can result as the measurement calibration from one device is transferred to another. In the art of sensor metrology or calibration, a primary standard can give substantial credibility to the calibration process and can be less apt to be disputed as calibration questions arise. Having the ability to install a permeation source 705 that is calibrated as a primary standard brings substantial credibility to the verification processes described herein.

Figure 12:
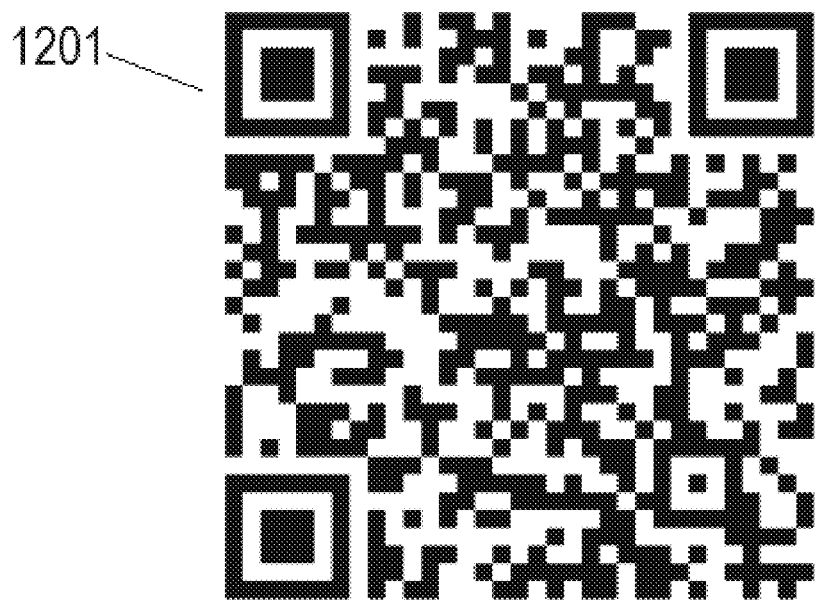
FIG. 12 illustrates an example of a two-dimensional barcode embodiment.

To support the calibration of permeation source 705, as embodiments of an embedded feature of CPU 701, calibration related data associated with 705 can be electronically stored within CPU 701, which is packaged with permeation source 705. As embodiments, the calibration related data associated with 705 may be electronically stored within any type of memory device including but not limited to Flash memory, USB Flash memory, EEPROM, SRAM, and read only memory. As embodiments, the calibration related data associated with 705 that is electronically stored within CPU 701 may include but is not limited to: permeation source serial number, calibration date, calibration due date, permeation source operating temperature, calibration species, permeation mass flow rate, calibration air flow rate, and calibration ppm output at the calibration temperature and air flow rate. As may be discussed, the calibration ppm output at the calibration temperature and airflow rate is the calibration value 1306. Once the calibrated permeation source 705 has been installed in the field, questions may arise which pertain to the source 705's calibration or viability. As an embodiment of the methods and systems described herein, the calibrated permeation source 705 can incorporate a label with a matrix bar code (also known in the art as a two-dimensional bar code) from which field personnel may readily obtain calibration records on the source 705 that is in question. FIG. 12 illustrates a two-dimensional barcode 1201 according to this embodiment. Bar code 1201 can electronically provide a website link that can be scanned using a mobile device, such as a mobile phone. Once scanned, the link provided by 1201 yields access to the calibration information associated with the source 705 on which the barcode 1201 is placed. This offers a convenient way to quickly deliver information on the setup or calibration of source 1201.

In another embodiment, the multipoint air sampling system can incorporate a field reference subsystem having a permeation source 705 that is calibrated as a transfer standard. As is known in the art of sensor metrology, a transfer standard involves a method of transferring the known calibration of a first entity to a second entity, following which the second entity can then be used as a source of calibration. For example, isobutylene is often used as a transfer standard for calibrating sensors, such as PID sensors. The concentration of the isobutylene gas can be determined using one standard (mass measurement for example) and that knowledge of gas concentration can then be transferred to the PID sensor as the PID is exposed to the gas and a recording of the PID's response is made. In this example, the isobutylene has been calibrated as a transfer standard. As is the case for any calibration source the quality of the transfer standard is a function of the uncertainty in the reliability of the standard. In one embodiment, the permeation source 705 is calibrated as transfer standard by exposing the sensor to the test gas produced by the source 705 and using the response as a calibration value of the source 705. As an example, permeation source 705 may be configured to produce roughly 7 ppm of isopropanol test gas when the air flow rate through tubing 718 is 2 liters per minute and the source 705 is held to the desired operating temperature (100 degrees Fahrenheit for example). Continuing with this example, a PID sensor with a 10.6 eV lamp which has been calibrated to isobutylene is then exposed to the isopropanol test gas which, as an example, yields a reading of 1.4 ppm as isobutylene as a response to the test gas. Therefore, the 1.4 ppm isobutylene response to source 705 would be recorded as the equivalent isobutylene calibration value for 705 when used as a transfer standard with the PID sensor that was used in the calibration. Also, note that for isopropanol the PID sensor with a 10.6 eV lamp may have a response factor of about 5.6 and therefore a calibrated value of (5.6*1.4 ppm as isobutylene) 7.84 ppm as isopropanol would be recorded for this permeation source 705. As an embodiment of the one or more embedded features held within CPU 701, said features include the calibration data for controlled permeation source 705 as a transfer standard. The uncertainty associated with using the permeation source 705 as a transfer standard in this example is influenced by the isobutylene calibration of the PID sensor and by how much the PID sensor has drifted since it was calibrated on isobutylene. To minimize the uncertainty that may result once source 705 has been calibrated as a transfer standard to a specific PID, the source 705 can be paired to the PID sensor that was used to calibrate source 705 as a transfer standard.

In some embodiments, the permeation source 705 can be paired to the one or more sensors. When a sensor of has been initially deployed in the field it is theoretically at its highest level of accuracy because it was just calibrated at the factory before being sent to the field. Once the sensor is installed in the field, it then may be expected to drift over time. To test the sensor with a specific concentration of test gas is of less importance if one at least knows the sensor's response to the test gas when it was initially calibrated, or when the sensor is initially deployed in the field. In one embodiment, the sensor within the multipoint air sampling system can be paired to the permeation source 705 when the sensor(s) is initially calibrated in order to calibrate the source 705 as a transfer standard. In another embodiment, the pairing of the source 705 to the sensor can be performed at the factory once the sensor has been calibrated. As an alternate embodiment, source 705 can be paired to the sensor when the sensor is installed in the field. The pairing process can involve recording the sensor's response when exposed to the test gas provided by the permeation source 705. The pairing process is one way to eliminate the need for an extensive mass-based calibration process of the permeation source 705. In one embodiment, the pairing process between sensor and the permeation source involves a method of reading the response of sensor to source 705 and storing this response as data in the memory associated with CPU 701. The memory associated with CPU 701 to which the sensor response is stored as data could be EEPROM based memory within the CPU 701. In another embodiment, the memory associated with CPU 701 to which the sensor response is stored as data can be any type of RAM based memory. In yet another embodiment, the memory associated with CPU 701 to which the sensor response is stored as data can be any type of Flash based memory.

The pairing of permeation source 705 and its attached CPU 701 to sensors can be accomplished via a user driven method of initiation. Said user driven method of initiation may include any method of prompting the CPU of the multipoint air sampling system to initiate the pairing process such as but not limited to any kind of switch or contact closure such as but not limited to a push button, relay contact, or jumper on any of CPU electronics, or sensor. Other user driven methods of initiating the pairing function includes but is not limited to a personal computer or hand-held computer serial connection such as a USB connection or RS232 connection. Other user driven methods of initiating the pairing function includes but is not limited to a wireless method of electronically communicating between a mobile device, such as a mobile phone using a mobile application which is connected to multipoint air sampling system's CPU using any form of wireless communications including but not limited to Bluetooth®, WiFi™, or other wireless methods that communicates or sets a software flag that would in turn be used by any of the CPU 606 CPU 701, or sensor to initiate the pairing function. Another user driven method of initiating the pairing function includes but is not limited to a web-based method where the user would initiate the pairing function by setting a software flag on a web page which may either be hosted by the multipoint air sampling system's CPU or it may be a web page that is hosted by an external website communicating either wirelessly to CPU or through a connection between the multipoint air sampling system and the field subsystem which is an internet connection. Another user driven method of initiating the pairing function includes but is not limited to a software flag or command initiated through BAS. A further method of initiating the pairing function includes but is not limited to a software flag or command sent from Information Management Server 220 to CPU 606.

Figure 13:
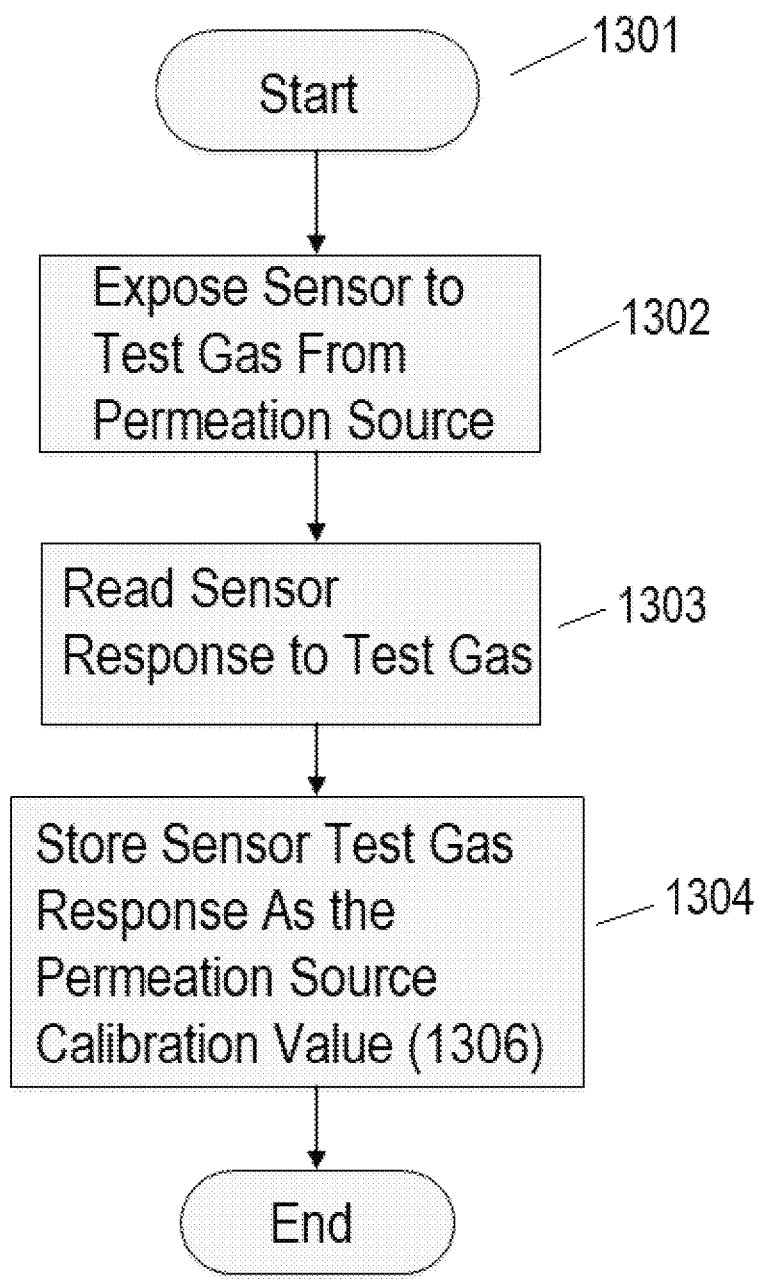
FIG. 13 illustrates an embodiment of a sequence executed by a CPU to pair a source to a CPU and sensors.

FIG. 13 illustrates an embodiment of a sequence which is administered by a CPU in order to pair source 705 and its attached CPU 701 to sensors. In one instance, the sequence 1300 is administered by the multipoint air sampling system's CPU 606. In other embodiments, the pairing function may be implemented by a CPU other than one associated with a multiplexed air sampling system. For example, in one embodiment the CPU source 705 and its attached CPU 701 can be paired with sensors at the manufacturer's factory using a CPU that is dedicated for the factory operation. As a further example and embodiment, specialized calibration and configuration electronics may be developed for a factory operation which can include the pairing of a permeation source with the sensor that said permeation source may operate with once the sensor and source have been installed in the field. The start 1301 of the sequence 1300 may be a user driven method of initiating the pairing function. Alternatively, the start 1301 of the sequence 1300 may be initiated by a non-user driven initiating function, as may be discussed further. Once the sequence 1300 has been initiated, in step 1302 the sensor can be exposed to the test gas provided by the permeation source 705. Step 1302 involves commanding valve 706 to open so that the test gas from permeation source 705 may flow from tubing 714 to tubing 712, where said test gas can then be drawn through the one or more sensors and exit through tubing 113, 213 to flow into flow control 114, 214 and then eventually to the vacuum source. In step 1303, readings can be taken from the one or more sensors which have been designated to pair with permeation source 705. Within step 1303 the one or more designated sensors are given the requisite time to respond to the test gas from source 705 before taking a reading. In step 1304, the response or sensor reading of sensor to the test gas is recorded and saved to memory, such as memory within multipoint air sampling system's CPU, memory within CPU 701 or memory within one or more sensors. The value or sensor reading captured in step 1303 is stored in step 1304 and this stored value in 1304 becomes the permeation source 705 calibration value 1306 as a transfer standard. For example, if the sensor is a PID sensor, the value stored in step 1304 is the response of the PID sensor to the test gas produced by 705. As a further example, if the response of the PID in step 1303 is 1.4 ppm as isobutylene, the value 1.4 ppm is the calibration value 1306 stored in step 1304. As an alternate embodiment, the value 1306 stored in step 1304 is the sensor reading as it is converted to the actual concentration of the gas species presented by the source 705. Based on a PID response factor of 5.6 to isopropanol, the sensed value of 1.4 ppm as isobutylene translates to 7.84 ppm as isopropanol which in this embodiment is the value stored in step 1304.

In one embodiment multiple sensors can be paired with the permeation source 705 and therefore readings from multiple sensors are taken in step 1303. For example, in one embodiment the sensors may include a PID sensor and an MOS sensor and the test gas from source 705 is a suitable VOC such as, for example isopropanol. Both the PID and MOS sensors have a different response to isopropanol and the response of each sensor can be captured in step 1303 and then a separate calibration value 1306 may be saved in step 1304 for each sensor.

As prior art, CPU/Valve Logic 106, 206 is responsible for reading sensed values from shared sensors 112, 212. Also, as prior art, CPU 106, 206 may read from 112, 212 attributes associated with sensors 112, 212 such as a unique identifier (serial number for example) from each sensor 112, 212 and calibration information. In an embodiment of this invention the multipoint air sampling system CPU can read attributes from its sensors and attributes from CPU 701 to determine and manage the pairing status of the permeation source 705 and the one or more shared sensors 112, 212. This embodiment is an example where the pairing function 1301 may be initiated by a non-user driven initiating function. One reason why such pairing management can be necessary is to ensure the permeation source 705 and CPU 701 are properly paired to the sensors should a first sensor be replaced with a second sensor due to a sensor failure or required service. Such pairing management may ensure that a replacement sensor may automatically be paired to the source 705 before the calibration of 705 is applied to the sensor.

Once the permeation source 705 has been calibrated, either as a primary standard or as a transfer standard using a pairing method embodiment, it may then be utilized to validate the accuracy of one or more shared sensors over the field life of said sensors. As one or more sensors is exposed to the source 705 test gas, the response to the test gas by sensor may be compared to the source 705 calibration value 1306 to determine the amount by which sensor has drifted.

Embodiments of the methods and systems described herein include a multipoint air sampling system which can incorporate a field reference subsystem 700 to generate one or more test gasses or species to at least test or validate one or more sensors associated with the multipoint air sampling system. In related embodiments, once the sensors have been tested using subsystem 700, one or more actions may be performed by systems such as 600A, 600B in response to said test. In one embodiment, the one or more actions that may be performed by system 600A, 600B in response to said test includes one or more reporting actions. In another embodiment, the one or more actions that may be performed by system 600A, 600B in response to said test includes one or more corrective actions.

One of the many unique aspects of the methods and systems described herein is that they provide a test gas source 705 that can be used continuously over a period of one to several years, depending on the amount of permeation liquid and species that is held within the permeation source's inner chamber (such as 811). For example, in the preferred embodiment of 800, if one were to apply only 20 milliliters of isopropanol to chamber 811, the permeation source 800 would be capable of continuously delivering a 5.6 ppm test gas of isopropanol with a carrier gas flowing at two liters per minute for no less than about two years. 5.6 ppm of isopropanol would be read by a calibrated PID sensor as roughly 1 ppm as isobutylene. By comparison, a gas cylinder holding 17 liters of 1 ppm isobutylene while discharging at two liters per minute, would be depleted in 8.5 minutes.

Figure 14:
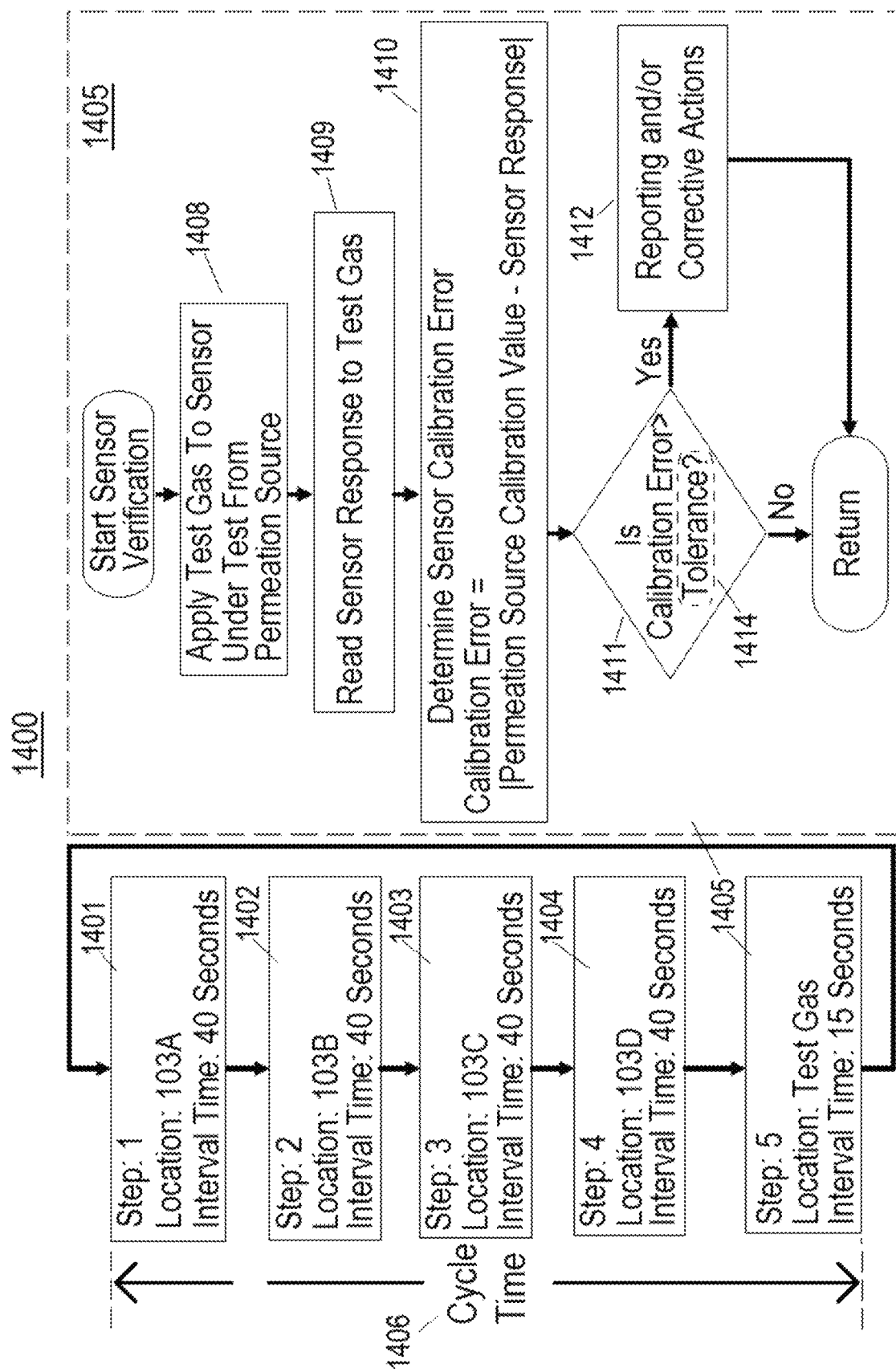
FIG. 14 illustrates an example of a sampling sequence which includes an inventive recurrent verification step.

Several inventive aspects leverage the significant gas capacity of the permeation source 705 to provide significant improvements to the service, reliability, and validation of a multipoint air sampling system, and this is especially valuable to higher risk applications involving the air sampling of harsh environments, such as lab exhaust environments for example. Because the permeation source 705 can continuously emit a test gas over long periods, as one embodiment, the field reference subsystem 700 is used to provide recurrent verification of the calibration or accuracy (herein recurrent verification) of the one or more sensors which are incorporated within the multipoint air sampling system. FIG. 14 illustrates an air sampling sequence 1400 for a multipoint air sampling system which includes a recurrent verification step 1405. The sequence 1400 shown in FIG. 14 pertains to a system that can be connected to four locations 103A, 103B, 103C, 103D. In application, the system may be expanded to support any number of locations however, the number of locations supported may in part be limited by the overall maximum cycle time 1406 that is permitted by the application. For example, in applications of exhaust demand control, it is desirable to limit the overall cycle time 1406 of the multipoint air sampling system to a maximum of about two to three minutes to ensure that contaminants May be detected rapidly enough by the system to prevent fumes from air streams 322A, 322B, 322C, 322D from being released by exhaust fan 326A, 326B, 326C at an exit velocity that is not sufficient for adequate dispersion of contaminants. As shown in FIG. 14, each step 1401, 1402, 1403, 1404 in the air sampling sequence may take 40 seconds. In practice the sampling time for each step 1401, 1402, 1403, 1404 can vary due to varying setup parameters for each monitored location. However, in the sequence of 1400 it can be assumed that each air sampling sequence takes approximately 40 seconds. The time required for each air sample is broken down into a first "purge" higher air flow rate during which the air sample is transported in a tubing 102 from the sample location 103 to the sensor, followed by second "sampling" lower air flow rate, over which time the sensor is exposed to the air sample for a sufficient duration to ensure the sensor can fully respond to any contaminants within the air sample. Typically, for example the sensor response time of a PID sensor used as sensor is about 15 seconds. Therefore, in the example of FIG. 14 the sequence duration for steps 1, 2, 3 and 4 would take about 160 seconds in this example.

The verification step 1405 shown in 1400 at least includes the sub steps of 1408 applying a test gas from permeation source 705 to one or more sensors, following which the one or more sensors' response to said test gas is recorded 1409 and compared to the calibration value 1306 of the permeation source 705 in order to determine the magnitude of the calibration error 1410. The verification step 1405 next includes in step 1411 evaluating if the calibration error in 1410 exceeds the allowed tolerance. The allowed tolerance in 1411 may be the manufacturer's specified tolerance of the sensor or it may be an application specific value. If the error determined in 1410 does exceed the tolerance, then in step 1412 the system 600A, 600B may provide the necessary reporting and/or corrective actions.

The sampling sequence can include a recurrent verification step 1405 to test the sensor 112, 212 during each sampling cycle of system 600A, 600B. In this embodiment the accuracy of sensor 112, 212 is intentionally tested using field reference subsystem 700 during virtually every sampling cycle 1400 to provide continuous verification of sensors 112, 212. Following the verification step 1405, should accuracy or sensor 112, 212 failure anomalies be detected, one or more corrective or reporting actions or both may be taken to ensure environmental safety is maintained. Embodiments of reporting actions should accuracy or sensor failure anomalies be detected following verification step 1405 include but are not limited to one or more calibration alarm events, such as a text message, email or other reporting which may be communicated through internet connection 604. Such a text message or email embodiment is valuable for the manufacturer's representative or other entity that is responsible for providing service to the system in order to ensure a quick response and in maintaining the up time of the system. In another embodiment of a reporting action should accuracy or sensor failure anomalies be detected following verification step 1405 a general alarm may be conveyed to the BAS via network 602 or to Information Management Server 220 through network connection 219. In another embodiment of a reporting action should accuracy or sensor 112, 212 failure anomalies be detected following verification step 1405, the system 600A, 600B conveys the alarm condition to an analog output incorporated within the system such as but not limited to a voltage output or a relay contact which may be used to signify a general alarm condition to other system, such as the BAS. Such a degree of verification of sensors provided by sequence 1400 is justified in critical applications such as exhaust demand control applications, where it is desirable to provide a maximum level of fault tolerance. It should be pointed out that those who are skilled in the art of ventilation controls would interpret the step 1405 as providing "continuous" verification, even though the inherent operation of the system is time multiplexed and therefore has discrete time elements. Previous systems have not been able to provide any level of recurring verification such as shown in 1400. The lack of such verification 1405, has deterred some practitioners from implementing exhaust demand control given the uncertainties associated with failed or drifted sensors.

As an embodiment, following the verification step 1405 a reporting action to an evidence log is provided whether accuracy or sensor failure anomalies are detected or not. A calibration certificate may be created by the manufacturer of the multipoint air sampling system for each sensor as they are calibrated at the factory. As has been described, such sensors can be deployed to the field for a period of 6 months, after which they are swapped for other newly calibrated sensors. Any time during the 6-month field life of these sensors a failure or calibration drift may occur which could be detrimental to the safety of more critical applications involving the monitoring of harsh environments, such as lab exhaust monitoring applications. In other systems, the only evidence that the sensor is calibrated may be the once per 6-month calibration certificate, which says nothing about the status of the sensors as they are operating in the field. In a reporting action embodiment, the multipoint air sampling system records the result of each verification step 1405 within an evidence log. FIG. 15 illustrates an embodiment showing the record content within an evidence log 1500. FIG. 15 shows only a few record entries for illustrative purposes. Each entry into this evidence log 1500, can include a date 1501 and time stamp 1502. As an embodiment, each record or row in the evidence log can include information on the permeation source 705, such as the permeation source 705 unique identifier or serial number 1503, the species that source 705 is generating 1504, and the calibration value 1505 of the source 705. This calibration value is the calibration value 1306 that is stored in CPU 701. The evidence log 1500 may also include information about the one or more sensors being tested, including but not limited to the sensor's serial number 1507 and the expected operating tolerance 1510 which can serve as one of the criteria for the test. Each record within the evidence log 1500 may include a recording of the sensor reading 1508 while under test, the calculated difference 1509 between the test concentration 1505 and the sensed concentration 1508, and a Pass/Fail assessment 1511. In some embodiments, the evidence log may also include information on a corrective action 1512 or a reporting action 1513 that may be taken as a result of the assessment 1511, or a Sensor Quality Index 1514 for each log entree that indicates the health of the sensor. The calibration evidence log 1500 may be implemented in any number of ways. For example, the calibration evidence log may be stored as a table within the memory of the multipoint air sampling system's CPU, it may reside in a database that is accessed by the multipoint air sampling system's CPU, or a database held within Information Management Server, or a database held within the BAS. In one embodiment, calibration evidence log 1500 can be stored as a file within a thumb drive or USB drive that is part of the multipoint air sampling system's CPU. The calibration evidence log can be part of a database that is part of a remote data center 605. In this embodiment, the calibration evidence records or rows in log 1500 are written periodically to said database by way of communications between the multipoint air sampling system and the remote data center. The remote data center may support any type of database including but not limited to a SQL database, Oracle database, MySQL, SQL Server or any other database. Users can have access to the remote data center where excerpts of the calibration evidence log may be searched by date and time and which data center enables user to download a report of the evidence log 1500 in a usable format, such as an Excel file or .csv file or .pdf file or any other usable format.

The evidence log can act as a live or active calibration certificate, which tracks the calibration of the sensor in a continuous or semi-continuous fashion. Such an evidence log can serve as important documentation to address behavioral aspects of lab occupants and facility and health and safety managers in the event of a large chemical spill leading to perceived malfunctions with the multipoint air sampling, by providing positive verification that the one or more sensors of the multipoint air sampling system were functioning correctly during the time of the incident. This verification would lead to a further examination of whether the occupants were following quantity limitation protocols.

In an embodiment, the recurrent verification step 1405 can be a multiple of cycle time 1406. In this embodiment verification step 1405 may not be performed during every sampling cycle of the multipoint air sampling system in order to allow the cycle time 1406 to be reduced, in order to ensure better speed of response of the sampling system. One reason why this embodiment can be important is that in some multipoint air sampling systems, the sensor response time may be considerably longer than the example time shown in 1405 so adding another step 1405 to the sequence 1400 during every cycle can hamper average system performance. Instead for example, one may decide to configure the system so that it implements verification step 1405 once every 10 cycles or even once every 50 cycles. At some point however there is a limit to this embodiment's practical usage when it comes to providing sensor verification to critical applications, such as applications where the multipoint air sampling system is monitoring lab exhaust. Generally, it is best to perform a verification step at least once a day, depending on the type of sensor and how it is being used.

In another embodiment, the verification step 1405 is scheduled based on any number of calendar dates and times. For example, the verification step 1405 could be scheduled to operate at a specific time of day every day. In this embodiment for example, one could schedule a verification step such as 1405 to take place at midnight every day. Having the flexibility of performing a calibration test on sensors during a time where a building in not normally occupied has the benefit of enabling the multipoint air sampling system to operate at a slightly faster sampling rate when the verification step 1405 is not included with the sampling sequence, such as the sequence described in FIG. 14.

The methods and systems described herein include several valuable corrective action embodiments which are implemented by the multipoint air sampling system once the sensor verification step 1405 has identified an accuracy issue with a sensor. In one embodiment, as part of a corrective action performed by system within step 1412, the sensor is automatically recalibrated to reduce the calibration error determined in step 1410. In one embodiment, system of this invention recalibrates the sensor by calculating a field calibration coefficient held in nonvolatile memory within system. Said field calibration coefficient can be applied to each sensor reading as a multiplicative function used to correct the factory calibration of the sensor.

Equation 1 illustrates the use of the field calibration coefficient to compute a corrected sensor reading. Initially, when a calibrated sensor is deployed in the field the calibration coefficient held within nonvolatile memory of the multipoint air sampling system may be set to one and the corrected sensor reading may equate to the sensor factory reading. As the sensor drifts up or down in its calibration and a calibration corrective action is performed as a function of step 1412 the calibration coefficient of Equation 1 may be adjusted by the system, such as system 600A, 600B. If the one or more sensors includes a plurality of sensors, then a field calibration coefficient may be applied to each sensor.

$$\text{Corrected Sensor Reading} = \text{Field Calibration Coefficient} * \text{Sensor Factory Reading} \quad \text{(Eq 1)}$$

Because the field calibration coefficient of Equation 1 should be initially set to a value of one, a suitable method of initializing the field calibration coefficient to a value of 1 as the sensor is first installed may be applied. As a preferred embodiment, the field calibration coefficient of Equation 1 is stored in nonvolatile memory on the sensor at the time the sensor is factory calibrated. In this embodiment, the system 600A, 600B can also have access to said nonvolatile memory on the shared sensors 112, 212 so that the system may both utilize the field calibration coefficient when calculating corrected sensor reading of Equation 1, and the system 600A, 600B is able to calculate a new value of the field calibration coefficient of Equation 1 as a calibration corrective action is required as a part of step 1412.

The field calibration coefficient of Equation 1 is intended for addressing what's referred to in the art of sensor metrology as sensor "span" drift. Many sensors with a linear response have a calibration that includes a slope and an intercept calibration value. In the art, the slope calibration value is often referred to as the span calibration, gain calibration or span, and the intercept calibration is often referred to as the zero calibration or zero. Aa PID sensor is normally calibrated with both a span and a zero calibration, however, PID's tend to drift more in their span calibration than they do in their zero calibration, so the corrected sensor reading of Equation 1 works well with a PID. With some sensors, including for example MOS sensors, substantial calibration drift can occur with the sensor's span and zero calibration values. As an embodiment, the corrected sensor reading incorporates both a field calibration coefficient and a field calibration offset value as illustrated in Equation 2. As a further embodiment to support the field calibration offset value of Equation 2, field reference subsystem 700 incorporates two-way valve 708 to selectively bypass the controlled permeation source in order to provide a zero-gas source for testing sensor in step 1405. In this embodiment, system 600A, 600B effectively tests the zero calibration of the sensor by closing the valve 708 and allowing air to flow from ambient 711 through scrubber 710 and then through valve 708 where it flows through path 712 and is applied to shared sensors 112, 212. In this embodiment, the path 712 side of valve 706 is isolated from controlled permeation source 705. As air flows from ambient 711 through scrubber 710, scrubber 710 removes all airborne compounds to create air with zero contaminants through 712. As this zero-air is routed through sensor 112, 212 a reading of sensor 112, 212 is established as step 1409 and said reading is established to determine a field calibration offset value (Equation 2) for the sensor. For example, if while performing said zero-air calibration test, the sensor responds with a reading of 4 ppm, then the field calibration offset value for the sensor may be −0.4 ppm to effectively zero the sensor with such a reading.

In this embodiment, the field calibration offset value is stored within nonvolatile memory within the system 600A, 600B. As a preferred embodiment, the field calibration offset value of Equation 2 is stored within nonvolatile memory within sensor 112, 212 that is accessible by system 600A, 600B.

$$\text{Corrected Sensor Reading} = \text{(Field Calibration Coefficient} * \text{Sensor Factory Reading)} + \text{Field Calibration Offset} \quad \text{(Eq 2)}$$

The methods described herein incorporate a corrected sensor reading as described in Equations 1 and 2 above in combination with recurrent verification step 1405, which provides a significant improvement to the accuracy and reliability of a multipoint air sampling system thereby significantly lowering the risks associated with applying such a system to monitor and or provide active control to critical lab exhaust applications. Because of the recurring aspects of the automatic field calibration function that has been described, the system 600A, 600B can correct sensor anomalies quickly while minimizing the down time of monitoring or monitoring with active control application. In the preferred embodiment where verification step 1405 can be provided during each sampling cycle of system 600A, 600B a sensor anomaly, such as a large calibration error in sensor 112, 212, may be corrected within one sampling cycle of the system 600A, 600B. With the automatic calibration embodiment, a multipoint air sampling system which would have had to otherwise be disabled when large calibration errors are detected, can be fixed in an automated way. Such a corrective action can be possible as long as the sensor has not failed to the point where it can no longer be calibrated. The corrective action of automatic calibration reduces maintenance costs associated with deploying a field technician to repair the problem and, for active sensing applications such as exhaust demand control applications, automatic calibration can substantially reduce any lost energy savings that would result if the exhaust demand control application had to be disabled due to a faulty sensor.

In applications where one or more sensors from a multipoint air sampling system are exposed to a harsh environment, such as contaminated lab exhaust air in duct work, the one or more sensors may drift in calibration over time due to sensor fouling as well as various physical degradation affects that may occur with the sensor technology over time. For example, PID sensors incorporate both a UV lamp 402 and electrode 409 and both may become fouled over time which may affect sensor calibration. In addition, however, UV lamp 402 may undergo a physical degradation such as lamp cracking or crazing which can result in a slow acting leak where the gas in the lamp, such as Krypton for example, may begin to leak out of the lamp 402. Krypton for example is often used as a gas for a 10.6 eV PID lamp. This gas is the PID's ionization source so, as the gas leaks out of the PID lamp, the PID's sensitivity and calibration may reduce. Such a leakage condition may often result in the PID's sensitivity dropping significantly over a short period of time and may often become noticeable over the course of a few days and may eventually lead to a non-recoverable failure in the lamp and the usability of the PID. When such a non-recoverable failure occurs, the PID can no longer be recalibrated or provide a usable signal. When a PID sensor for a multipoint air sampling system is calibrated at the manufacture's factory, the PID sensor may undergo what is known as a burn-in period whereby the PID sensor can be calibrated and then after several days its calibration may be verified to determine if a lamp leakage condition exists.

In one reporting action embodiment 1412, the method which incorporates a corrective action involving a recalibration step to sensors in combination with recurrent verification step 1405 also incorporates a step of reporting said recalibration step within evidence log 1500. As was discussed above, the sensors of a multipoint air sampling system may drift in calibration over time due to sensor fouling as well as various physical degradation affects that may occur with the sensor technology over time. When the sensor has succumbed to physical degradation effects, the sensor may no longer hold a stable calibration for very long (often only days) and often at this point the sensor may not be able to function for much longer and it may be at the end of its useful field life. One of the symptoms of the sensor being at the end of its useful field life is that it may drift at a higher rate than was previously observed.

Sensor drift, especially with sensors that are exposed to harsh lab exhaust, may occur during normal operation of the sensors due to contaminant related fouling. Therefore, in application the recurring verification step 1405 could expectedly result in instances where it is determined by 1405 that the sensor has drifted to the point where it must be recalibrated, and this may happen several times over the normal field life (6 months for example) of sensors. Therefore, based just on the knowledge that a sensor has undergone the field recalibration function, one likely cannot determine if the sensor is likely to soon fail in a non-recoverable manner. The rate at which sensors drift can vary significantly from one installation to the next, as some lab facilities may have relatively clean lab exhaust and others, such as those with many active fume hoods, can have lab exhaust that is heavily contaminated on a repeated basis. Therefore, the average rate at which a sensor drifts is in part determined by the environment that the sensors are exposed to. One of the objectives of the methods and systems described herein is to ease the service requirements associated with maintaining a multipoint air sampling system that is applied to monitor harsh environments, such as lab exhaust environments. What is needed to achieve this is a method of determining the overall health of the one or more sensors in the multipoint air sampling system and a method to anticipate when service is required for these sensors. The corrective action involving a recalibration step to sensors of the multipoint air sampling system in combination with recurrent verification step 1405 can also incorporate a step of ranking the integrity of the sensor via a Sensor Quality Index. The said Sensor Quality Index 1514 may also be reported within evidence log 1500. The Sensor Quality Index (SQI) is generated by an analysis module which ranks a sensor's integrity using a function that is weighted by the combination of the sensor drift rate and an environmental limit value. As embodiments, the SQI module may be performed by any device or system that is part of the multipoint air sampling system including but not limited to the multipoint air sampling system's CPU, an Information Management Server 220, or remote data center 605. As an alternate embodiment, the SQI module may be performed by the BAS. The SQI provides a measurement of sensor integrity as a method of predicting the likelihood of a sensor failing in a non-recoverable manner. For example, the SQI module can be used to predict if a PID sensor is likely to soon fail in a non-recoverable manner where a sensor recalibration step would not remedy the problem. Sensor integrity can generally refer to any aspect of the sensor's accuracy performance gaged against the expected tolerance of the device for the application in which it is used. Sensor integrity may be referred to as "good" if the sensor is operating within its accuracy specifications and "bad" if it is working outside of its operating specifications. Therefore, sensor integrity is a term that is often used in a qualitive manner. However, the SQI rating can provide a highly quantitative way of determining sensor integrity.

FIG. 16A illustrates an embodiment of logic used to generate SQI values for one or more sensors within the multipoint air sampling system. In one embodiment, the logic 1600A can be run each time verification step 1405 results in a corrective action step 1412 that is a recalibration of a sensor. In one embodiment, a sensor's SQI value ranges ideally from a value of one which indicates normal sensor integrity to a value approaching zero which indicates a complete sensor failure. As a corrective action step 1412, SQI logic 1600A can be started 1601, following which it calculates the current sensor drift rate 1602 and average sensor drift rate 1603. In one embodiment, the drift rates 1602 and 1603 are based on the tolerance 1414 and the amount of time between a corrective action step 1412 that is a recalibration of the sensor. For example, if the sensor is a PID sensor and the tolerance 1414 for that sensor is 0.4 ppm as isobutylene and said sensor has taken 10 days to drift by 0.4 ppm, then the current sensor drift rate 1602 for the PID would be 0.04 ppm per day. The average sensor drift rate 1603 may, in one embodiment be a simple average of all recorded drift rates 1602 while the sensor has been installed. In an alternate embodiment, the average sensor drift rate 1603 may be a time weighted average of all recorded drift rates 1602. One objective of SQI logic 1600A is to discern the degree to which a sensor recalibration rate is abnormal. When a sensor begins to fail, the rate at which the sensor drifts 1602 may increase significantly in relation to the average drift rate 1603. Initially, as 30 calculated in step 1607, the SQI value is proportional to the average drift rate 1603 divided by the current drift rate 1602. Therefore, initially, when the sensor begins to fail and therefore its drift rate 1602 increases significantly, this may be registered as a sudden reduction in the SQI value. However, assuming the sensor continues to require recalibration at an ever-increasing rate, over time the average drift rate 1603 may begin to increase which may affect the SQI value and its ability to identify the sensor failure. For this reason, the SQI logic 1600A incorporates a limit drift rate value 1604 which may be adjusted based on the harshness of the environment that is monitored by the multipoint air sampling system. The limit drift rate parameter 1604 is representative of the typical drift rate for the sensor given the intensity of the contaminant levels being monitored. For example, assuming the sensor is a PID sensor that is exposed to intense concentrations of exhaust contaminants, then the sensor may normally drift by as much as 0.2 ppm per day. Therefore, in an application such as this with intense exhaust contaminant levels a limit drift rate 1604 of 0.2 ppm per day may be applied. In other embodiments, different limit drift rate settings can be applied based on knowledge of typical sensor performance for different types of environments. For example, step 1604 may support values for any number of different environments. Each time SQI logic 1600A is run, the average sensor drift rate 1603 can be inspected by step 1605 to determine if the average drift rate 1603 is in excess of the limit 1604 and, if so, then the SQI may be calculated as the ratio of limit drift rate 1604 to current drift rate 1602 within block 1606. FIG. 16B illustrates an embodiment with an example of 15 intervals of SQI calculations for an example PID sensor which is applied as a sensor within a multipoint air sampling system. FIG. 16B shows 15 recalibration events 1609 and a row of data for each event. Column 1610 represents the total number of days that the example PID sensor has been in operation with the multipoint air sampling system. Column 1611 is the calculated number of days between calibration events 1609. Column 1630 is the sensor drift rate calculation 1602 for the example drift scenario. Column 1631 is the calculation of average sensor drift 1603 which utilizes the simple average embodiment. Column 1614 is the average drift rate 1603 limited or clamped by the limit drift rate 1604. Column 1615 is the SQI that is calculated for each interval of 1609 based on the SQI logic of 1600A. In this example 1600B, it is assumed that the PID sensor is exposed to a severe exhaust environment and a suitable limit drift rate 1604 is chosen based on this assumption. It should be understood that this method can include any value chosen for limit value 1604 and that the value chosen in this example 1600B is one of any range of values 1604 that might be chosen. As shown in FIG. 16B, this example illustrates a scenario where a sensor which happens to be a PID sensor, is initially installed and after 6.2 days it is determined by logic 1405 that the sensor has drifted by its allowed tolerance 1617 of 0.4 ppm. Therefore, by the first recalibration event the sensor has drifted by 0.4 ppm over 6.2 days; and the drift rate at that point is 0.065 ppm per day. At that point the SQI is determined to be a value of 1, which indicates that the sensor integrity is normal. FIG. 16B further illustrates that in this scenario, with each recalibration event 1609 the days between each event 1611 gradually decrease, and therefore the current drift rate (ppm/day) 1602 gradually increases. The trend continues for the first eight calibration events, during which the SQI is calculated using the equation 1607 of 1600A. By event 9 of this example 1616, the average drift rate 1603 can exceed the limit drift rate 1604 of 0.2 ppm and, therefore, logic module 1600A then switches to calculating the SQI based on equation 1606. As calibration events 1609 continue beyond event 9 the SQI value falls precipitously, thus indicating the poor integrity of the sensor at that point.

Rating a sensor's integrity with the SQI can provide a novel and effective way to anticipate the need for sensor maintenance by a field technician. Once the SQI has been calculated following a sensor recalibration event 1609, logic can be applied to determine if a notification or reporting action for service must be sent based on the value of the SQI and rules which have been configured within a notification system used to provide a reporting action that is associated with the multipoint air sampling system. A reporting action for service enables those responsible for servicing the multipoint air sampling system to be informed of a condition, such as a sensor condition which needs attention. Such a reporting action for service based on a deteriorating SQI value, as an embodiment, provides a proactive method of ensuring excellent service. Reporting actions include any kind of practical method to communicate to a remote party, including but not limited to a text message, email, tweet or other notification which may be communicated through internet connection 604, information management server 220, BAS 603, or data center 605. In embodiments, notification reporting actions may be performed by any device or system that is part of the multipoint air sampling system including but not limited to the multipoint air sampling system's CPU, the Information Management Server 220, or remote data center. As an alternate embodiment, notifications or other reporting actions based on SQI values may be performed by the BAS. FIG. 16C illustrates embodiments of rules logic which may be applied to determine three different reporting levels based on the SQI value determined by 1600A.

FIG. 16C illustrates an embodiment where the SQI is translated into one of three possible reporting categories including Normal Operation 1618, Maintenance Warning 1620, and Maintenance Required 1622. In one embodiment of 1600C the reporting action system can provide a notification regardless of the sensor SQI value. As an alternate embodiment, the notification system can be flexibly configured to enable or disable notifications for each reporting level. In this embodiment, therefore, the user could choose to have a notification sent only if the SQI translates to a Maintenance Warning 1620 or a Maintenance Required notification 1622. In another embodiment of 1600C, the thresholds 1621 and 1619 which correlate with each notification type are user adjustable. The user configured threshold 1621 for example is used to send a Maintenance Required message or notification 1622 when the SQI is a value of 25 or less. Again, threshold 1621 may be adjusted by the user in order to provide more or less sensitivity. For example, if the threshold 1621 is lowered from the value of 0.25 the notification system may become less sensitive to the drift rate of the sensor. Similarly, threshold 1619 may be adjusted in order to increase or lower the notification system's sensitivity to send a Maintenance Warning message or notification 1620.

The teachings of this invention provide significant improvements to the service, reliability, and validation of a multipoint air sampling system, especially in applications involving the air sampling of harsh lab environments, such as lab exhaust environments. The combination of ranking a sensor with an SQI and the notification logic of 1600C enables a manufacturer's representative or other field technicians to better anticipate and plan the service schedule for systems. Although the validation, calibration and notification aspects of the methods and systems discussed thus far are tremendous advances, there are some applications where sensor maintenance of the multipoint air sampling systems may still be very challenging due to a combination of severe sensor fouling due to environmental conditions as well as the implications of issues with sensor infant mortality or sensor quality issues that may lead to reduced meantime to failure MTTF. For example, in some cases the manufacturer's representative who provides service to maintain a multipoint air sampling system may service clients over a very large geographic location from a singular office that may be hundreds of miles away from a given client's site where a system is installed. Even though infant mortality rates with sensors may be relatively low, when a sensor failure does occur in between scheduled maintenance visits to a site, it can be very expensive for the representative to travel to the site to address the failure issue. This problem is further exacerbated when the remote site involves an exhaust sensing application where, due to exceptionally high exhaust contaminant levels, the sensor fouls quickly. Also as has been discussed, in some applications involving highly adsorptive compounds, such as ammonia, sensors may foul rapidly and to the point where they cannot be recalibrated without some form of conditioning. What's needed is a method of further safeguarding such systems so that when unexpected failures occur, they can be more easily managed by those responsible for service without incurring a loss in safety or energy savings. For example, as a described herein, when a failure in one or more sensors is detected as a part of the recurrent validation 1405, a general alarm may be set in the system. For exhaust demand control applications, as has been described, the system described in U.S. application Ser. No. 16/141,109 correctly responds to a general alarm condition by taking the exhaust fan system out of setback to ensure safety. In such a condition where for example the failure of one or more sensors can be detected by 1405, this may result in a general alarm which may result in the exhaust fan system being correctly taken out of setback. When the exhaust fan system is taken out of setback for this reason, the exhaust demand control application may not save energy until the sensor is fixed.

The shared sensors 112, 212 within a multiplexed air sampling system may comprise a wide range of different sensor types depending on the application. General IEQ monitoring sensors may include sensor types for the detection of airborne particulate matter, carbon dioxide ($CO_2$), carbon monoxide (CO), humidity levels, some acids and non-organic compounds, and a broad range of volatile organic compounds including but not limited to PID and MOS sensors. In more specialized applications, the shared sensors may include photoacoustic infrared sensing, non-dispersive infrared sensing, flame ionization spectroscopy, and electrochemical sensor technology. U.S. Pat. No. 5,394,092, which is incorporated herein by reference, describes what's known in the art as a pulse discharge detector or PDD. PDD's are mostly used in controlled lab environments where they can provide improved performance over a PID sensor when it comes to detecting high ionization potential compounds, such as some acids for example, which a PID cannot detect. A PPD sensor can be adapted for use as a sensor within a multipoint air sampling system that would benefit from the teachings of this invention. It should be understood that any sensor type that can be used within a multipoint air sampling system may be compatible with the methods and systems described herein.

Figure 17A:
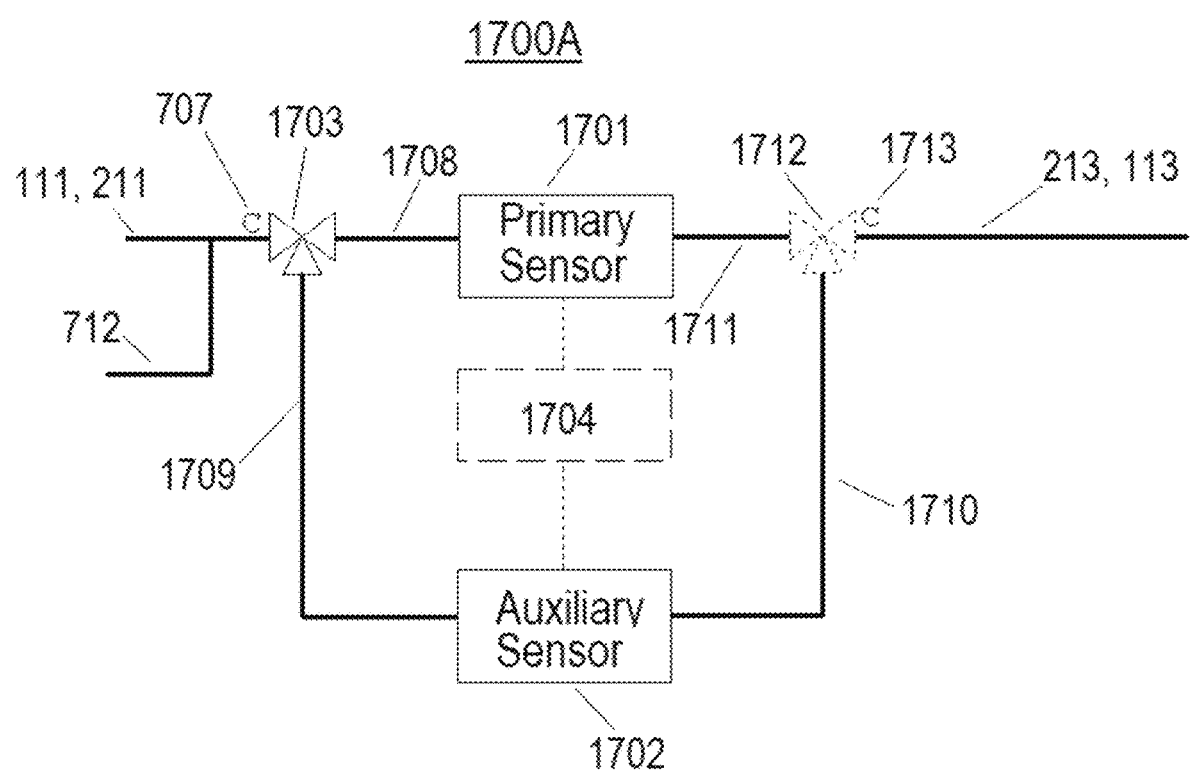
FIG. 17A illustrates embodiments which incorporate primary and auxiliary sensor configuration.

The shared sensors which may be applied to the star-configured embodiment 600A as well as the distributed configured embodiment 600B of a multipoint air sampling system incorporating field reference subsystem 700 may include one or multiple sensor types. In an embodiment, one or more of each sensor type within the shared sensors of the multipoint air sampling system individually comprise a primary sensor and one or more auxiliary sensors of the same type and said one or more auxiliary sensors may be used as either a temporary or permanent replacement for the said primary sensor. FIG. 17A illustrates the primary and auxiliary sensor configuration 1700A of this embodiment. Although only one auxiliary sensor 1702 is shown in FIG. 17A, it should be understood that embodiments can include any number of auxiliary sensors 1702. Configuration 1700A includes a primary sensor 1701 of a given sensor type and one or more auxiliary sensors 1702 of the same type as the primary sensor 1701. Therefore, in one embodiment, if the primary sensor 1701 is a PID sensor, then the one or more auxiliary sensors 1702 may also be a PID sensor. Embodiments of the systems described herein can incorporate a 3-way solenoid valve 1703 which can be used to direct air samples flowing from sampled locations into the shared sensors or the test gas flowing through 712 to either the primary sensor 1701 or the auxiliary sensor 1702. The primary sensor 1701 and the one or more auxiliary sensors 1702 may either be packaged together within the same enclosure or they may be packaged separately. When the sensors 1701 and 1702 are packaged together, sensors 1701 and 1702 can be installed on a common circuit board. In one embodiment, the primary and auxiliary sensors 1701 and 1702 are PID sensors. In yet another embodiment, a primary PID sensor 1701 and an auxiliary PID sensor 1702 are both installed on a common printed circuit board which also contains valve 1703. Configuration 1700A also includes an optional 3-way valve 1712 and optional conditioning element 1704.

Figure 18A:
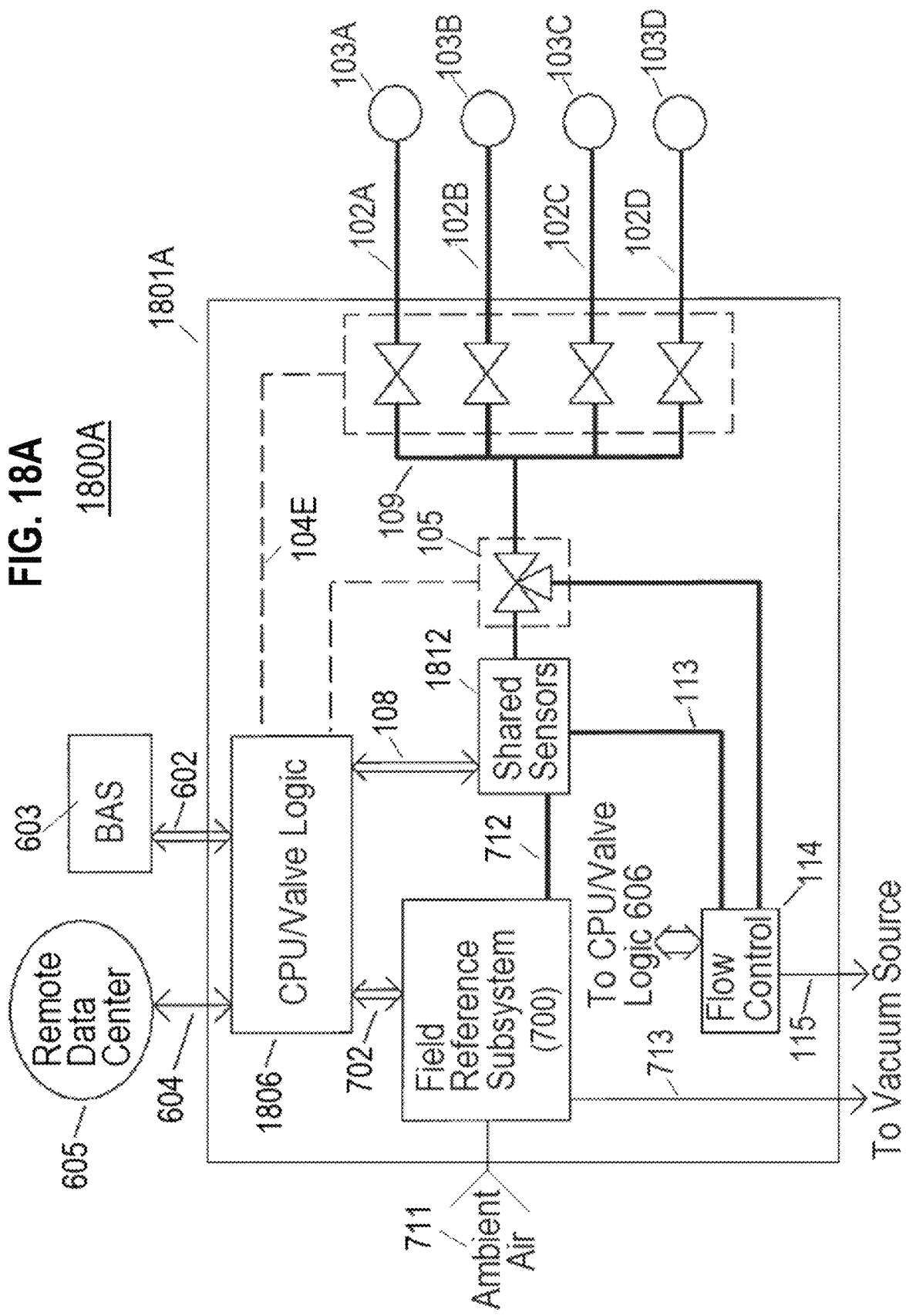
FIG. 18A illustrates an embodiment of a star-configured multipoint air sampling system incorporating one or a plurality of auxiliary sensors.
Figure 18B:
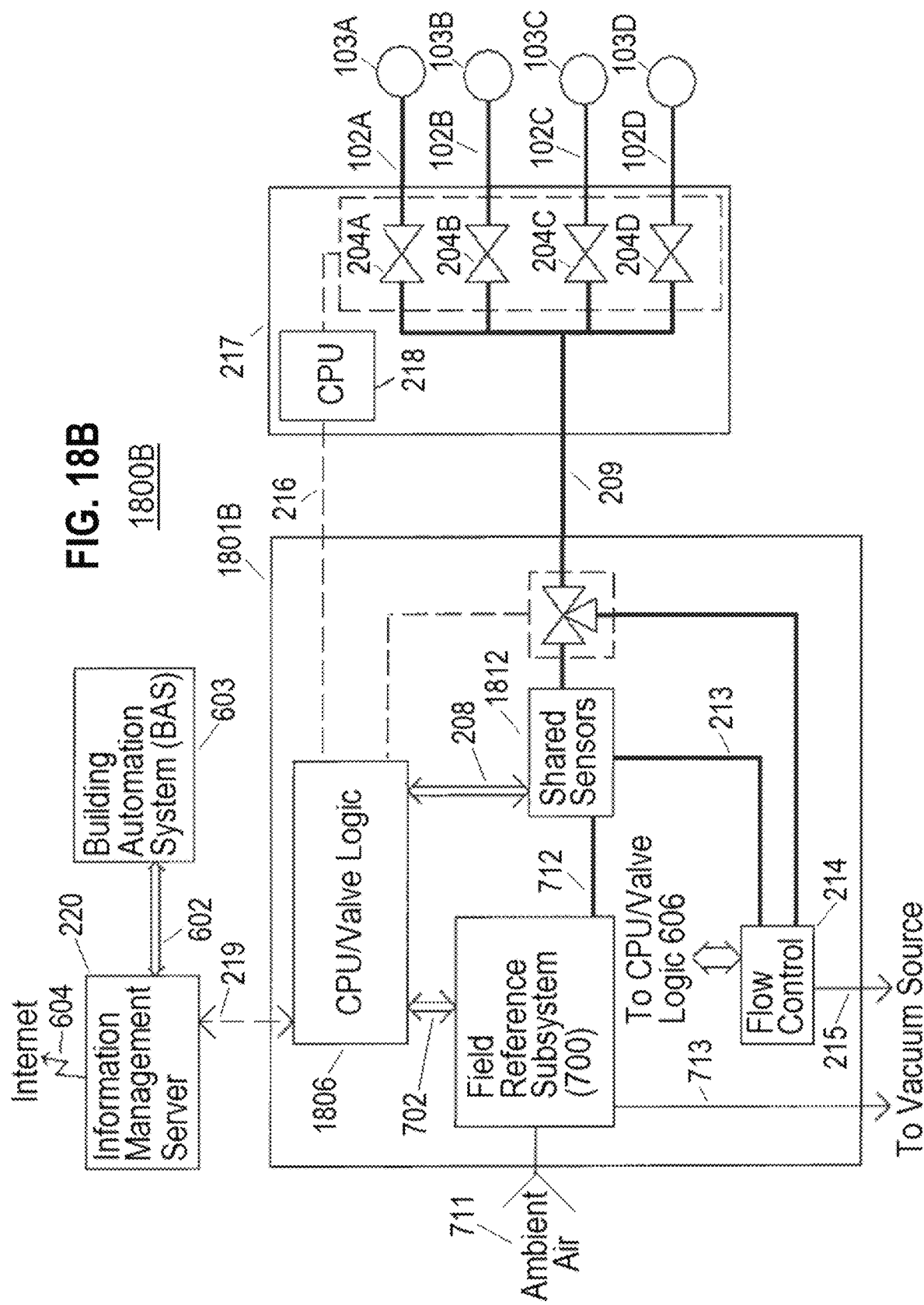
FIG. 18B illustrates an embodiment of a distributed multipoint air sampling system incorporating one or a plurality of auxiliary sensors.

As an embodiment, FIGS. 18A and 18B show a modification of the system 600A and 600B which includes a shared sensor assembly 1812 that is composed at least in part of the sensor configuration of 1700A. FIGS. 18A and 18B illustrate the implementation of a shared sensor 1812 in which at least one sensor type incorporates not only a primary sensor 1701 but also one or a plurality of auxiliary sensors 1702. In one embodiment, the 3-way valve 1703 can be controlled via CPU/Valve Logic 1806 which has been adapted from logic executed in the multipoint air sampling system's CPU to control the valve 1703 via interface 108, 208.

The methods and systems described herein can test the one or more sensors associated with the multipoint air sampling system, and also provide corrective actions such as sensor recalibration. In one embodiment, involving the configuration of system 1800A, 1800B a test gas from field reference subsystem 700 is applied to connection 712 to expose sensors 1812 as a calibration corrective action, following which the resulting SQI value calculated for primary sensor 1701 is used to determine if auxiliary sensor 1702 should be enabled and primary sensor 1701 disabled. In this embodiment the inventive SQI value is being further utilized to determine if the integrity of primary sensor 1701 is adequate so that it may be continued to be used and if not, valve 1703 may be directed to open the path between common flow path 1707 and path 1709 so that, while auxiliary sensor 1702 is enabled, air samples can be routed through sensor 1702. An SQI value which causes the auxiliary sensor 1702 to be enabled may be referred to herein as the "failover SQI value". Once the system 1800A, 1800B has switched to the auxiliary sensor 1702, then the integrity of auxiliary sensor 1702 can be tracked by computing SQI values for that sensor 1702 and applying the SQI values to determine reporting actions based on settings 1619 and 1621. The auxiliary sensors further safeguard the system 1800A, 1800B so that when unexpected failures occur, they can more easily be managed by those responsible for service. For example, the system 1800A, 1800B may switch to auxiliary sensor 1702 due to infant mortality issues with primary sensor 1701, or severe fouling issues with 1701 which would otherwise require immediate travel by the field technician to the site in which the multipoint air sampling system is installed. With the auxiliary sensor 1702 switched into the system 1800A, 1800B under these conditions the application supported by multipoint air sampling system 1800A, 1800B is not interrupted and may continue to operate safely and in energy savings applications such as exhaust demand control applications, may continue to provide energy savings.

In a further embodiment involving auxiliary sensor 1702, system 1700A can be applied to multipoint air sampling system 1800A, 1800B to provide a sensor reconditioning function to renew sensor performance of either the primary sensor 1701 or the auxiliary sensor 1702. In an embodiment of 1700A described above, once the auxiliary sensor 1702 is applied, the primary sensor 1701 can be permanently taken out of service until it is returned to the manufacturer for recalibration and service. In a further embodiment, once the primary sensor 1701 is taken out of service it is reconditioned by system 1704 so that it may be placed back in service at some point. In embodiments, once a failover SQI value has been realized with the primary sensor 1701, the auxiliary sensor 1702 may be enabled and 1702 is used while sensor 1701 is reconditioned. Further, once a failover SQI value has been realized for auxiliary sensor 1702, primary sensor 1701 may be re-enabled and auxiliary sensor 1702 disabled and reconditioned. This process may then continue indefinitely, or until one of the sensors 1701, 1702 can no longer be reconditioned. This embodiment is especially valuable for lab exhaust applications where the exhaust contaminants include highly adsorptive compounds such as ammonia for example. As has been described, high concentrations of ammonia may be present in lab exhaust from vivarium or animal holding spaces. Ammonia can quickly foul a sensor 1701, 1702 however, the effects are often reversible.

Embodiments of system 1704 include any number of methods for reconditioning sensors 1701 and 1702, including but not limited to thermal desorption, vacuum desorption, a combination of thermal and vacuum desorption, and other methods used to desorb contaminants from a sensor 1701, 1702. As is known to those experienced in the art of analytical chemistry, thermal desorption is the process where heat is applied to increase the vapor pressure or volatility of contaminants so that they become liberated from the surface of the material to which they are adhered. With the thermal desorption embodiment of 1704, 1704 includes a heat source that is applied to the sensor 1701, 1702 that is being conditioned in order to liberate the contaminants adsorbed to the sensor 1701, 1702. In one embodiment, the heat source may be a heater element that is built into the sensor 1701, 1702 that is controlled by elements of system 1704. In one embodiment, thermal desorption is provided by the system 1704 to sensors 1701 and 1702, which are PID sensors. One aspect of PID sensors is that the field life of a PID's lamp 402 can be shortened when the lamp 402 is activated while exposed to elevated ambient temperatures. Typically, the maximum desirable ambient operating temperature of a PID lamp 402 is 100 degrees Fahrenheit, yet an optimal temperature for the thermal desorption embodiment of 1704 is 130 degrees Fahrenheit. As a preferred embodiment of the thermal desorption embodiment of 1704 the PID 1701 or 1702 that is undergoing a thermal desorption conditioning process is turned off during the conditioning process. FIG. 17B illustrates the thermal desorption sequence for either primary sensor 1701, or auxiliary sensor 1702. The start of the thermal desorption process 1715 occurs when a failover SQI value is reached for either sensor 1701 or 1702, whichever is active or enabled at the time. Logic step 1716 then determines which sensor 1701, 1702 is to be conditioned and, for the thermal desorption embodiment 1700B, that sensor 1701, 1702 is isolated via step 1720, for the primary sensor, and step 1717 for the auxiliary sensor. The step of isolating sensor 1701 or 1702 involves valves 1703 and 1712. For example, to isolate the primary sensor 1701, the flow path from common port 1707 is connected to path 1709 of the auxiliary sensor and the common port 1713 of valve 1712 is connected to path 1710 which connects to the other side of the auxiliary sensor 1702. Before the heater element is turned on the sensor being conditioned 1701 or 1702 is turned off by logic 1721 or 1718, respectively. The heater is then turned on for the sensor being conditioned 1701 or 1702 by logic 1722, 1719, respectively. Next, a timer is set 1723 which determines how long the thermal desorption process 1700B may take place. In embodiments, the thermal desorption process 1700B may take any amount of time depending on the severity of the sensor fouling determined by knowledge of the level of contamination present in the lab exhaust monitored by system 1800A, 1800B. As a preferred embodiment, timer 1723 is set to one hour. Once the timer 1723 has counted down to zero via logic 1724, the thermal desorption process for the sensor being conditioned 1701, 1702 may terminate and, as one embodiment, that sensor which has just been reconditioned may be held on standby until a failover SQI value is reached for the currently active sensor.

Vacuum desorption is the process by which the environmental total pressure is reduced (placed under a vacuum) in order to counter the molecular bonding forces of contaminants so that the contaminants can be liberated from a surface. As an embodiment of 1700A, vacuum desorption can be used to recondition the sensor 1701 or 1702 by using the vacuum connections 115, 215 connected to flow control 114, 214, which in turn is connected to flow path 113, 213 of multipoint air sampling system 1800A, 1800B. In some embodiments, the vacuum which may be developed when applied to a sensor 1701 or 1702 as a reconditioning step can be at least 60% of atmospheric pressure (8 to 9 psia) or less. A vacuum desorption sequence can be used in conjunction with 1700A for either primary sensor 1701, or auxiliary sensor 1702. The start of the vacuum desorption process occurs when a failover SQI value is reached for either sensor 1701 or 1702, whichever is active or enabled at the time. A first logic step determines which sensor 1701 or 1702 is undergoing reconditioning, which involves drawing and holding a vacuum on the primary sensor 1701 or auxiliary sensor 1702, whichever is undergoing the reconditioning process. Both valves 1703 and 1712 can be involved with the process of drawing and holding a vacuum on the sensor being conditioned. The process of drawing a vacuum is a relatively quick activity, as it involves evacuating the relatively small volume which surrounds the sensor 1701, 1702. This relatively small volume around the sensor 1701, 1702 can be related to the way in which sensors are typically packaged for multipoint air sampling systems, which usually involves a simple air tight shroud which sits over the sensor 1701, 1702 so that tubing can easily be connected to the sensor to enable the sensor to be exposed to air samples that may be routed through 1701, 1702 from common point 1707. Typically, the volume within the shroud that surrounds each sensor is on the order of one to several cubic inches. To draw a vacuum on sensor 1701 or 1702 requires that valve 1703 be closed to the sensor being conditioned and that valve 1712 be opened to the sensor being conditioned. Therefore, for example, in the configuration of 1700A, to draw a vacuum on the primary sensor 1701 requires that the port connecting to path 1708 of valve 1703 be closed and that the port 1711 of valve 1712 be opened to port 1713. In doing so, the vacuum connected to 113, 213 may evacuate the primary sensor 1701, and this evacuation may occur usually within a few seconds. Once the primary sensor of this example is evacuated, the valve 1712 may then be opened to the port connecting to path 1710, thus trapping the vacuum in the primary sensor for conditioning purposes and enabling the auxiliary sensor to be utilized. Next, a timer is set which determines how long the vacuum desorption process may take place. In embodiments, the vacuum desorption process may take any amount of time depending on the severity of the sensor fouling determined by knowledge of the level of contamination present in the lab exhaust monitored by system 1800A, 1800B. As a preferred embodiment, a timer is set to one hour. Once the timer has counted down to zero via logic, the vacuum desorption process for the sensor being conditioned may terminate and, as one embodiment, that sensor which has just been reconditioned may be held on standby until a failover SQI value is reached for the currently active sensor. However, any possible method of sequencing or activating a sensor 1701, 1702 once it has been reconditioned can be used.

In a further embodiment, the thermal desorption process of 1700B can be combined with a vacuum desorption process to enhance the amount of desorption of contaminants from sensor 1701 or 1702, which can improve the quality of the sensor conditioning process. One of the affects that can take place for example when just applying a method of thermal desorption for conditioning a sensor 1701 or 1702 is that, at the conclusion of the process 1725, compounds that were liberated from the condition sensor may re-adsorb to the sensor over time. The method 1700B of thermally desorbing contaminants from sensor 1701 or 1702 can be immediately followed by the method of providing vacuum desorption. In this embodiment, the contaminants which are liberated from the sensor 1701 or 1702 during the thermal desorption process 1700B are then carried away from the sensor 1701 or 1702 by the vacuum.

It is quite common for a PID to become fouled when overexposed to ammonia and other highly adsorptive compounds and usually this results in the PID's reading being enhanced when in the presence of moisture. This means that the PID's reading may be higher than expected for a given exposure level to contaminants. However, this effect is generally a reversible one, and as an embodiment, the PID sensor can be field reconditioned. As an example, a PID sensor can be fouled in this manner in lab exhaust application involving exhaust air coming from animal rooms or vivarium spaces. The PID sensor can be used as a shared sensor and can be tested for fouling by highly adsorptive compounds using the test gas produced by field reference subsystem 700 that is applied to said PID as a verification step 1405 and determining if the response to said test gas is an enhanced reading from the PID. As a further embodiment involving the testing for fouling embodiment, once it has been determined that the PID has been fouled due to highly adsorptive compounds the PID can be reconditioned using thermal desorption method 1700B, vacuum desorption, or a combination of thermal desorption and vacuum desorption.

In lab exhaust monitoring applications involving a multipoint air sampling system, it is common to incorporate a volatile organic compound (VOC) sensor to provide added sensing capabilities in addition to the PID sensor normally used. For example, a Metal Oxide Semiconductor sensor (MOS) may be used because it can detect certain compounds such as methanol and acetonitrile, that a PID sensor cannot detect. MOS sensors, however, tend to drift in calibration very quickly and they can be especially problematic to use in lab exhaust monitoring applications for this reason. Additionally, other sensors may be included in the multipoint air sampling system. In one embodiment, the field reference subsystem 700 can provide a test gas for one or a plurality of sensors by incorporating multiple permeation liquids within chamber 811 of the permeation source 705. For example, to support the recurring validation of a PID and MOS sensor as, the permeation source 705 may contain both isopropanol and methanol to create a test gas that is a blend of isopropanol and methanol.

The exhaust demand control system 300 can incorporates a PID sensor because of its broad detection capabilities, including the detection of a wide range of high dilution compounds which may require the full dilution capability of the fans 326A, 326B, 326C when a spill occurs but it also includes a wide range of low dilution compounds which may be equivalently detected by PID 112, 212 but which do not require much dilution from 326A, 326B, 326C because the low dilution compounds are not very odiferous or toxic. Such interfering low dilution compounds can, with elevated concentrations, result in energy waste by the exhaust demand control system 300 because the PID reading may be elevated by the interfering compounds and the elevated reading due to the low dilution compounds cannot be distinguished from elevated reading due to high dilution compounds. One of the more common interfering low dilution compounds which can affect exhaust demand control performance is ammonia from animal spaces or vivariums which can be present in high enough concentrations that it may prevent the exhaust demand control system 300 from properly setting back fans 326A, 326B, 326C which can result in significant energy waste.

Figure 19:
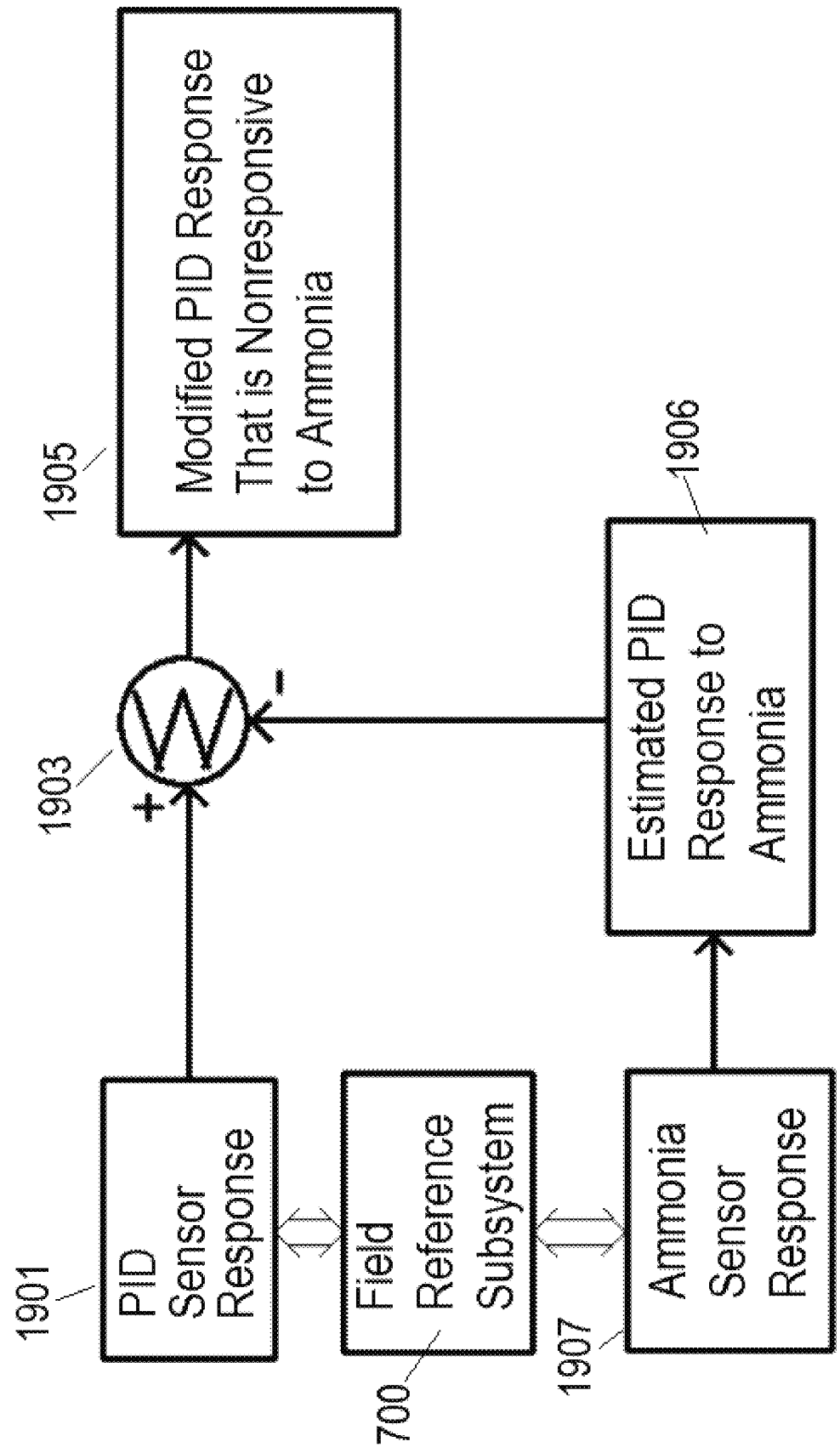
FIG. 19 illustrates an embodiment of a method for creating a PID response where the low dilution compound is ammonia.

In another aspect, a multipoint air sampling system uses a field reference subsystem 700 to provide a modified PID signal that can be substantially nonresponsive to a specific interfering low dilution compound. Ammonia is a low dilution compound that the said modified PID signal can be substantially nonresponsive to. In a further embodiment, the modified PID signal which can be substantially nonresponsive to ammonia can be used as an exhaust contaminant concentration signal in an exhaust demand control application. In these modified PID signal embodiments, the PID signal can be altered using a method which incorporates the field reference subsystem 700 and a speciating low dilution compound sensor that is included as one of the shared sensors. The said speciating low dilution compound sensor can be responsive primarily to the specific low dilution compound. The subsystem 700 can be used to generate a precise concentration of the low dilution compound to be omitted from the modified PID response. The test gas from the subsystem 700 can be used to establish the exact relationship between the PID's response and that of the speciating low dilution compound sensor to the specific low dilution compound, in order to create a transfer function which enables an estimation of the PID's response to the specific low dilution compound to be made from the response of the speciating sensor; said estimated response is then subtracted from the PID's actual response in order to establish a signal that is substantially nonresponsive to the specific low dilution compound. FIG. 19 details a method for the application where the low dilution compound is ammonia, however, aspects of 1900 may be applied to methods of creating a PID response that omits other compounds as well. In 1900, the field reference subsystem 700 has its controlled permeation source 705 configured to emit ammonia as the test gas. In one embodiment of 1900, the permeation source 705 uses ammonium hydroxide as the permeation liquid in order to provide an ammonia test gas. In the embodiment of 1900, the speciating sensor's response 1907 is that of an ammonia sensor and, in a preferred embodiment, sensor response 1907 is that of an electrochemical ammonia sensor. A method described herein provides a modified PID response 1905 that is nonresponsive to ammonia which may be applied to any PID sensor. The method of 1900 uses the test gas from subsystem 700 to establish the exact relationship between the PID response 1901 to the ammonia test gas provided by 700 and the response 1907 of the ammonia sensor to the test gas provided by 700, and this relationship is stored within function block 1906. Function 1906 is the calculated transfer function which maps the ammonia sensor's response 1907 to ammonia to the PID sensor's response 1901 to ammonia. As a general embodiment, function 1906 is a logic module or a lookup table held within any CPU in the multipoint air sampling system 1800A, 1800B, 600A, 600B. As embodiments, function 1906 can be a logic module or a lookup table held within CPU 606 or CPU 1806. As an embodiment, the function 1906 is an equation or lookup table that translates the ammonia ppm response 1907 of the ammonia sensor to the ppm as isobutylene PID response 1901 as the PID is exposed to the same level of ammonia. It should be noted that in the implementation of 1900 within the systems described herein, the PID sensor associated with 1901 and ammonia sensor associated with 1907 are exposed to the same air sample with each air sample taken introduced to the shared sensors and therefore the sensors associated with responses 1901 and 1907 may be exposed to substantially the same amount of ammonia with each air sample. The estimated PID response to ammonia 1906 is introduced to summing block 1903 and this value from 1906 is subtracted from the total PID response of the PID associated with response 1901 to establish output 1905, which is the modified PID response that is omissive of ammonia.

The invention claimed is:

1. A multipoint air sampling system, the system comprising:
  a field reference subsystem carrying out a recurrent verification of one or more sensors associated with the multipoint air sampling system;
  a permeation source within the field reference subsystem which source is calibrated as a transfer standard, wherein the permeation source generates one or more test gasses used to evaluate an integrity of the one or more sensors;
  a processor configured for executing a logic module for rating the integrity of the one or more sensors, wherein the processor executes the logic module in response to the recurrent verification of the one or more sensors; and
  a report generator configured for generating a reporting action in response to the recurrent verification of the one or more sensors.

2. The system of claim 1, wherein the permeation source comprises an immersion tube source.

3. The system of claim 2, wherein the immersion tube source comprises a tubing manufactured from high density polyethylene.

4. The system of claim 1, wherein the one or more sensors comprises a PID sensor.

5. The system of claim 1, wherein the one or more test gases comprises isopropanol.

6. The system of claim 1, wherein the permeation source further comprises a permeation source paired to the one or more sensors.

7. The system of claim 1, wherein the permeation source comprises a permeation source calibrated as a primary standard.

8. The system of claim 1, wherein the reporting action comprises an alarm.

9. The system of claim 1, wherein the reporting action comprises an evidence log.

10. The system of claim 1, wherein the processor executes the logic module to generate a sensor quality index.

11. The system of claim 10, wherein the processor executes the logic module to generate a sensor corrective action recommendation based on the value of the said sensor quality index.

12. The system of claim 11, wherein the sensor corrective action comprises a sensor recalibration.

13. The system of claim 11, wherein the sensor corrective action comprises a sensor reconditioning function.

14. The system of claim 10, wherein the report generator generates a reporting action for service based on the sensor quality index.

15. The system of claim 1 wherein the permeation source comprises one or more embedded features.

16. The system of claim 1, wherein the one or more sensors comprise a photoionization detector (PID) PID sensor and a speciating low dilution compound sensor and the permeation source is configured to generate a test gas having an interfering low dilution compound, and further including:
  a logic module configured to perform a test mode to determine a relationship of a response of the PID sensor and a response of the speciating low dilution compound sensor to the test gas for generating estimated responses of the PID sensor to varying concentrations of the interfering low dilution compound, wherein the logic module is further configured to perform an operational mode to subtract from a response of the PID sensor the interfering low dilution compound based on a response of the speciating low dilution compound sensor to provide a modified PID signal as an exhaust contaminant concentration signal.

17. The system of claim 16, wherein the speciating low dilution compound sensor comprises an ammonia sensor and the interfering low dilution compound comprises ammonia.

* * * * *